US008394770B2

(12) United States Patent
Possani-Postay et al.

(10) Patent No.: US 8,394,770 B2
(45) Date of Patent: Mar. 12, 2013

(54) VM23 AND VM24, TWO SCORPION PEPTIDES THAT BLOCK HUMAN T-LYMPHOCYTE POTASSIUM CHANNELS (SUB-TYPE KV1.3) WITH HIGH SELECTIVITY AND DECREASE THE IN VIVO DTH-RESPONSES IN RATS

(75) Inventors: Lourival Domingos Possani-Postay, Morelos (MX); Georgina Gurrola-Briones, Morelos (MX); Saida Patricia Salas-Castillo, Veracruz (MX); César Vicente Ferreira Batista, Morelos (MX); Zoltán S. Varga, Debrecen (HU); György Panyi, Debrecen (HU); Rezső Gáspár, Debrecen (HU)

(73) Assignee: Universidad Nacional Autonoma de Mexico, Mexico City (MX)

( * ) Notice: Subject to any disclaimer, the term of this patent is extended or adjusted under 35 U.S.C. 154(b) by 221 days.

(21) Appl. No.: 12/599,978

(22) PCT Filed: May 14, 2007

(86) PCT No.: PCT/IB2007/001544
§ 371 (c)(1),
(2), (4) Date: Sep. 7, 2010

(87) PCT Pub. No.: WO2008/139243
PCT Pub. Date: Nov. 20, 2008

(65) Prior Publication Data
US 2011/0059064 A1    Mar. 10, 2011

(51) Int. Cl.
*A61K 38/16* (2006.01)
*C07K 14/435* (2006.01)
(52) U.S. Cl. .................. 514/17.4; 514/18.3; 514/21.3; 530/300
(58) Field of Classification Search .................. None
See application file for complete search history.

(56) References Cited

FOREIGN PATENT DOCUMENTS
EP           0916681 A1    5/1999
WO     WO 2006/116156 A2    11/2006

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era, Trends in Biotech. 18(1):34-39.*

Two novel toxins from the Amazonian scorpion *Tityus cambridgei* that block Kv1.3 and Shaker B K+-channels with distinctly different affinities; Cesar V.F. Batista, Froylan Gomez-Lagunasa, Ricardo C. Rodriguez de la Vega, Peter Hajduc, Gyorgy Panyic, Rezso Gaspac, Lourival D. Possania,; Received May 21, 2002; received in revised form Sep. 18, 2002; accepted Sep. 19, 2002.
Molecular basis of a-KTx specificity; Kathleen M. Giangiacomo, Yamille Ceralde, Theodore J. Mullmann; Department of Biochemistry, Temple University School of Medicine, 3420 N. Broad Street, Philadelphia, PA 19140, USA; Received Oct. 2, 2003; accepted Nov. 5, 2003 Available online May 25, 2004.
Novel a-KTx peptides from the venom of the scorpion *Centruroides elegans* selectively blockade Kv1.3 over IKCa1 K+ channels of T cells; Timoteo Olamendi-Portugal, Sandor Somodi, Juan Antonio Fernandez, Fernando Z. Zamudio, Baltazar Becerril, Zoltan Varga, Gyorgy Panyi, Rerso Gaspar, Lourival D. Possania, Received Feb. 22, 2005; revised May 31, 2005; accepted Jun. 1, 2005 Available online Jul. 18, 2005.
Review—Ion channels and lymphocyte activation; György Panyi , Zoltán Varga, Rezso Gáspár; Received Nov. 14, 2003; accepted Nov. 28, 2003.
*Current Pharmaceutical Design*, 2006, 12, 2199-2220; K+ Channel Blockers: Novel Tools to Inhibit T Cell Activation Leading to Specific Immunosuppression; G. Panyi, L. D. Possani, R.C. Rodriguez de la Vega, R. Gáspár and Z. Varga.
Mini-review; Current views on scorpion toxins specific for $K^b$-channels; Ricardo C. Rodriguez de la Vega, Lourival D. Possani; Department of Molecular Medicine and Bioprocesses, Institute of Biotechnology, National Autonomous University of Mexico, Avenida Universidad, 2001, Apartado Postal 510-3, Cuernavaca 62210, Mexico; Available online May 18, 2004.
Viewpoint: A unified nomenclature for short-chain peptides isolated from scorpion venoms: a-KTx molecular Subfamilies; Jan Tytgat, K. George Chandy, Maria L. Garcia, George A. Gutman, Marie-France Martin-Eauclaire, Jurg J. van der Walt and Lourival D. Possani; Nov. 1999 (vol. 20).

(Continued)

*Primary Examiner* — Christine J Saoud
*Assistant Examiner* — Jon M Lockard
(74) *Attorney, Agent, or Firm* — Fay Sharpe LLP; Brian E. Turung

(57) ABSTRACT

Potassium channels Kv1.3 are known to be implicated in immunological diseases and graft rejections. Disclosed are peptides capable of blocking with high affinity and specificity potassium channels Kv1.3, their pharmaceutical compositions, and methods for their use to block Kv1.3 potassium channels, to treat various immunological conditions and to diagnostic applications. Methods for their chemical synthesis and correct folding are also disclosed. Exemplary peptides correspond to protein components (Vm23 and Vm24) isolated from the venom of the Mexican scorpion *Vaejovis mexicanus smithi*. Vm23 and Vm24 bind to hKv1.3 channels in an almost irreversible manner, showing a Kd value in the order of 3 picomolar range, when applied to human lymphocytes cultures in vitro. Vm24 was chemically synthesized and used in in vivo experiments to successfully treat sensitized rats (on the DTH-response). Neither Vm24 nor synthetic Vm24 is toxic to mice when injected at relatively high concentrations (assayed up to 10,000 micrograms per kilogram mouse body weight). These peptides (Vm24 and Vm23) and their functional equivalent analogs with at least 83% of sequence identity are lead compounds, candidates for the treatment of various immunological conditions and diagnostic applications.

24 Claims, 24 Drawing Sheets

OTHER PUBLICATIONS

Figure 1:
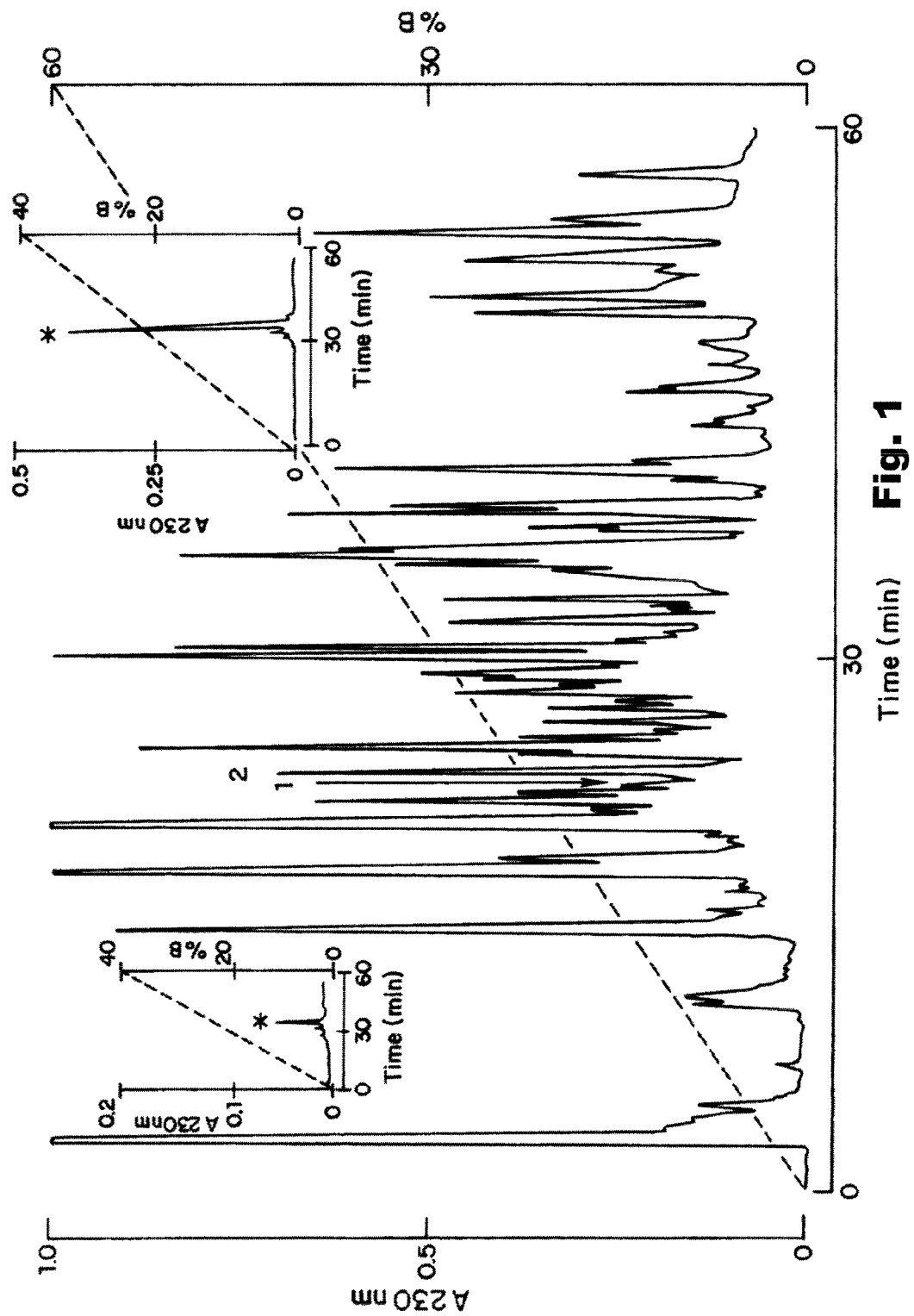

*Current Pharmaceutical Design*, 2007, 13, 2456-2468; © 2007 Bentham Science Publishers Ltd. Involvement of Membrane Channels in Autoimmune Disorders; Zoltán Varga, Péter Hajdu, György Panyi, Rerso Gáspár and Zoltán Krasznai.

Mass Spectrometry in Proteomics; Ruedi Aebersold and David R. Goodlett; The institute for Systems Biology, 4225 Roosevelt Way NE; Washington 98105; 2001 American Chemical Society.

Modulation of hte Cardiac Sodium Channel Nav1.5 by Fyn, a Src Family Tyrosine Kinase; Christopher A. Ahern, Ji-Fang Zhang, Marilyn J. Wookalis, Richard Horn; Cellular Biology, May 13, 2005.

Topology of the Pore-Region of a K+ Channel Revealed by the NMR-Derived Structures of Scorpion Toxins; Aiyar, et al. Neuron, vol. 15, 1169-1181, Nov. 1995 Copyright.

Mapping the Functional Anatomy of BgK on Kv1.1, Kv1.2, and Kv1.3; Allessandri-Haber, et al. downloaded from www.jbc.org at UNAM.Direccion de Bibliotecas. Departamento de Suscripciones; Nov. 6, 2009.

Basic Local Alignment Search Tool by Stephen F. Altschul, et al. 1990 Academic Press Limited.

A potassium channel toxin from the secretion of the sea anemone Bunodosoma granulifera. Isolation, amino acid sequence and biological activity by Abel Aneiros, et al. 1993 Elsevier Science Publishers B.V. All rights reserved.

Leiurotoxin I (Scyllatoxin), a Peptide LIgand for CA2+-activated K+ Channels by Patrick August et al.; vol. 265, No. 8, Issue of Mar. 15, 1990, pp. 4753-4759, The Journal of Biological Chemistry.

Stimulatory Action of Internal Protons on Slo1 BK Channels, by Vladimir Avdonin, et al., 2003 by the Biophysical Journal, vol. 84, May 2003, 2969-2980.

Anuroctoxin, a new Scorpion Toxin of the a-KTx 6 Subfamily, is Highly Selective for Kv1.3 over IKCa1 Ion channels of Human T Lymphocytes by Mikos Bagdany et al., Molecular Pharmacology 2005.

Proteomic analysis of the venom from the scorpion *Tityus stigmurus*: Biochemical and physiological comparison with other *Tityus* species by C.V.F. Batista et al. 2007 Published by Elsevier, Inc.

Selective blockade of T lymphocyte K+ channels ameliorates experimental autoimmune encephalomyelitis, a model for multiple sclerosis by Christine Beeton et al., Nov. 20, 2001, vol. 98, No. 24.

The Neuroscientist, Potassium Channels, Memory T cells, and Multiple Sclerosis by Christine Beeton and K. George Chandy, Neuroscientist 2005.

Targeting Effector memory T cells with a selective peptide inhibitor of Kv1.3 channels for therapy of autoimmune diseases, by Christine Beeton, et al. 2005 The American Society for Pharmacology and Experimental Therapeutics; vol. 67, No. 4.

Kv1.3 Channels are a therapeutic target for T cell-mediated autoimmune diseases by Christine Beeton et al., Nov. 14, 2006, vol. 103, No. 46.

Selective Blockage of voltage-dependent K+ channels by a novel scorpion toxin by Emilio Carbone et al., Reprinted from Nature, vol. 296, No. 5852; Mar. 4, 1982.

Characterization of a potassium channel toxin from the Caribbean Sea anemone *Stichodactyla helianthus* by Olga Cataneda, et al., Toxicon, vol. 33, No. 5, 1995 Elsevier Science Ltd.

Toxins in the Characterization of Potassium Channels by N. A. Castle et al.; TINS, vol. 12, No. 2, 1989 Elsevier Science Publishers.

$K^1$ channels as targets for specific immunomodulation by K. George Chandy et al.; 2004 Elsevier Ltd.

The pathogenesis of immune thrombocytopaenic purpura by Nichola Cooper and James Bussel Department of Pediatrics, Weill Medical College of Cornell University, New York, NY, USA 2006 Blackwell Publishing.

A unified nomenclature for short-chain peptides isolated from scorpion venoms: a-KTx molecular Subfamilies by Jan Tytgat, et al.; TiPS Nov. 1999 vol. 20 1999 Elsevier Science.

Recapitulation of B cell differentiation in the central nervous system of patients with multiple sclerosis by Anna Corcione, et al.; Jul. 27, 2004; vol. 101 No. 30; PNAS Org.

Kaliotoxin, a Novel Peptidyl Inhibitor of Neuronal Bk-Type $Ca^{2+}$-activated K+ Channels characterized from *Androctonus mauretanicus mauretanicus* Venom by Marcel Crest, et al; The Journal of Biological Chemistry 1992 The American Society for Biochemistry and Molecular Biology, Inc.

Voltage-Gated Potassium Conductance in Human T Lymphocytes Stimulated with Phorbol Ester by C. Deutsch, et al.; Dept. of Physiology, Univ. of PA G4, 1986.

Wide Phylogenetic distribution of Scorpine and long-chain B-KTx-like peptides in scorpion venoms: identification of "orphan" components by Elia Diego-Garcia, et al.; 2006 Elsevier.

The structure of the potassium channel: molecular basis of $K^+$ conduction and selectivity by Declan A. Doyle, et al.; Apr. 3, 1998; 280, 5360; ProQuest Medical Library.

Chemical Synthesis, structural and functional characterization of noxiustoxin, a powerful blocker of lypmphocyte voltage-dependent K+ channels by E. Drakapoulou, et al.; 8/24/995 by Academic Press.

Calcium-activated potassium channels sustain calcium signaling in T lymphocytes; Selective blockers and manipulated channel expression levels, by Fanger, et al.; The Journal of Biological Chemistry 2001; vol. 276, No. 15, Issue of Apr. 13, 2001.

Antisense oligodeoxynucleotides directed against Kv1.5 mRNA specifically inhibit untrarapid delayed rectifier K+ current in cultured adult human atrial myocytes; by Jianlin Feng, et al.; 1997 American Heart Assoc., Inc.

Purification and characterization of a unique, potent, peptidyl probe for the high conductance calcium-activated potassium channel from venom of the scorpion *Buthus tamulus*; by A. Valvez et al.; 1990 the American Society for Biochemistry and Molecular Biology, Inc.

Purification and Characterization of Three Inhibitors of Voltage-Dependent K+ Channels from *Leiurus quinquestriatus* var. *hebraeus* Venom by Maria L. Garcia, et al.; 1994 American Chemical Society.

Potassium channels: from scorpion venoms to high-resolution structure by M.L. Garcia, et al.; 2001 Elsevier Science Ltd.

Purification, Characterization, and Biosynthesis of Margatoxin, a Component of *Centruroides margaritatus* Venom That Selectively Inhibits Voltage-dependent Potassium Channels by M. Garcia-Calvo, et al.; 1993 The American Society for Biochemistry and Molecular Biology, Inc.

Up-regulation of the IKCa1 Potassium Channel during T-cell Activation; Molecular Mechanism and Functional Consequences by S. Ghanshani, et al.; 2000 The American Society for Biochemistry and Molecular Biology, Inc.

Molecular basis of a-KTx specificity by K. Giangiacomo et al.; 2004 Elsevier Ltd.

Mechanism of charybdotoxinblock of a voltage-gated K+ channel by Steve A.N. Goldstein & Christopher Miller; 1993 by the Biophysical Society vol. 65, Oct. 1993.

The charybdotoxin receptor of a shaker K+ channel; peptide and channel residues mediating molecular recognition by S. Goldstein et al.; Neuron, vol. 12, 1377-1388, Jun. 1994 by Cell Press.

Expression and chromosomal localization of a lymphocyte K+ channel gene by Stephan Grissmer et al.; vol. 87, pp. 9411-9415, Dec. 1990 Immunology.

Calcium-activated potassium channels in resting and activated Human T lymphocytes; expression levels, calcium dependence, ion selectivity, and pharmacology by Stepan Grissmer, et al. Oct. 1, 1993.

Pharmacological characterization of five cloned voltage-gated K+ channels, types Kv1.1,1.2,1.3,1.5, and 3.1, stably expressed in mammalian cell lines by S. Grissmer et al.; the American Society for Pharmacology and Experimental Therapeutics 1994.

International union of pharmacology. LII. Nomenclature and molecular relationships of calcium-activated potassium channels by Aguan D. Wei, et al.; 2005 the American Society for Pharmacology and Experimental Therapeutics, vol. 57, No. 4.

Recent studies on Dendrotoxins and potassium ion channels by Alan L. Harvey; 1997 Elsevier Science Inc.

Revealing the architecture of a K+ channel pore through mutant cycles with a peptide inhibitor by Patricia Hidaldo & Roderick Mackinnon; Apr. 14, 1995 ProQuest Medical Library.

MRBayes: Bayesian inference of phylogenetic trees by John P. Huelsenbeck & Fredrik Ronquist Bioinformatics Applications Note vol. 17, No. 8, 2001.

T- and B-Cell Responses to Myelin Oligodendrocyte Glycoprotein in Experimental Autoimmune Encephalomyelitis and Multiple Sclerosis by Antonio Iglesias, et al.; 2001 Wiley-Liss, Inc.
Potassium-dependent Changes in the Conformation of the Kv2.1 Potassium Channel Pore by David Immke, et al.; Jun. 1999 The Rockefeller University Press.
A rationally designed CD4 analogue inhibits experimental allergic encephalomyelitis by Bradford A. Jameson, et al.; Letters to Nature, vol. 368 Apr. 21, 1994.
Signaling through immune system receptors by Janeway, 2001.
Toxin determinants required for interaction with voltage-gated $K^p$ channels by Besma Jouirou, et al.; 2004 Elsevier Ltd.
Potassium channel blockers in multiple sclerosis: Neuronal Kv channels and effects of symptomatic treatment by Susan I.V. Judge, et al.; 2006 Elsevier Inc.; Pharmacology and Therapeutics.
Synthetic Melittin, Its Enantio, Retro, and Retroenantio Isomers, and Selected Chimeric Analogs: Their Antibacterial, Hemolytic, and Lipid Bilayer Action by Padmaja Juvvadi, et al.; Journal of the American Chemical Society Sep. 25, 1996; vol. 118, No. 38.
ShK-Dap$^{22}$, a Potent Kv1.3-specific Immunosuppressive Polypeptide by Katalin Kalman, et al.; Journal of Biological Chemistry 1998.
Complex Subunit Assembly of Neuronal Voltage-Gated K1 Channels Basis for High-Affinity Toxin Interactions and Pharmacology; 1997 The American Society for Biochemistry and Molecular Biology, Inc.
Blockade of the voltage-gated potassium channel Kv1.3 inhibits immune responses in vivo b GC Koo, et al.; The Journal of Immunology; 1997.
Solution structure of the potassium channel inhibitor agitoxin 2: Caliper for probing channel geometry; by Andrzej M. Krezel, et al.; Protein Science 1995.
$NH_2$-terminal inactivation peptide binding to a C-type-inactivated Kv channels; Harley T. Kurata, et al. The Journal of General Physiology Apr. 12, 2004.
A four-disulphide-bridged toxin, with high affinity towards voltage-gate K+ channels, isolated from *Heterometrus spinnifer* (Scorpionidae) venom; Bruno Lebrun, et al. Journal of Biochemistry 1997.
Structure of the KvAP voltage-dependent K+ channel and its dependence on the lipid membrane; Seok-Yong Lee, et al.; PNAS,Oct. 25, 2005; vol. 102, No. 43.
CCR4 versus CCR10 in human cutaneous $T_H$ lymphocyte trafficking; Dulce Soler, et al.; Blood, Mar. 1, 2003, vol. 101, No. 5.
Intimations of K+ channel structure from a complete functional map of the molecular surface of charybdotoxin; Per Stampe, et al.; 1994 American Chemical Society.
Potassium channel toxins, P.N. Strong 1990 Pergamon Press.
Synthesis and Structural Characterization of Charybdotoxin, a Potent Peptidyl Inhibitor of the High Conductance Ca2+-activated K+ Channel, Elizabeth E. Suggs et al.; The Journal of Biological Chemistry 1990.
The CLUSTAL_X windows interface: flexible strategies for multiple sequence alignment aided by quality analysis tools; Julie D. Thompson, et al.; Nucleic Acids Research, 1997, vol. 25, No. 24.
Gene Family Evolution and Homology: Genomics Meets Phylogenetics, Joseph W. Thornton and Rob DeSalle; Copyright 2000 by Annual Reviews.
A unified nomenclature for short-chain peptides isolated from scorpion venoms: a-KTx molecular Subfamilies; Jan Tytgat, et al.; TiPS—Nov. 1999, vol. 20.
Structure-guided Transformation of Charybdotoxin Yields an Analog That Selectively Targets Ca21-activated over Voltage-gated K1 Channels; Heiko Rauro et al.;2000 The Journal of Biological Chemistry.
Novel interactions between K1 channels and scorpion toxins; Ricardo C. Rodriguez de la Vega, Enrique Merino, Baltazar Becerril and Lourival D. Possani; Trends in Pharmacological Sciences vol. 24, No. 5, May 2003.
Scorpion toxins specific for $Na^+$-channels; Lourival D. Possani, Baltazar Becerril, Muriel Delepierre and Jan Tytga; Eur. J. Biochem. 264, 287-300 (1999) FEBS 1999.

Current views on scorpion toxins specific for $K^+$-channels; Ricardo C. Rodriguez de la Vega, Lourival D. Possani; May 18, 2004.
Molecular cloning of a putative tetrodotoxin-resistant rat heart $Na^+$ channel isoform ([$^3$H]saxitoxin receptors/multigene family/denervated skeletal muscle); R.B. Bogart, et al.; Proc. Natl. Acad. Sci. USA; vol. 86, pp. 8170-8174, Oct. 1989.
MrBayes 3: Bayesian phylogenetic inference under mixed models; Fredrik Ronquist and John P. Huelsenbeck; Bioinformatics; Aug. 12, 2003; 19, 12, ProQuest Medical Library.
Two subsets of memory T lymphocytes with distinct homing potentials and effector functions Federica Sallusto, Danielle Lenig, Reinhold Forster, Martin Lipp & Antonio Lanzavecchia; 1999 Macmillan Magazines Ltd.
Central Memory and Effector Memory T Cell Subsets: Function, Generation, and Maintenance; Federica Sallusto, et al.; Copyright 2004 by Annual Reviews.
hERG potassium channels and cardiac arrhythmia; Michael C. Sanguinetti & Martin Tristani-Firouzi; 2006 Nature Publishing Group.
Mapping Function to Structure in a Channel-Blocking Peptide: Electrostatic Mutants of Charybdotoxin; Chul-Seung Park and Christopher Miller; Biochemistry 1992; American Chemical Society 1992.
Transient outward potassium current, '/to', phenotypes in the mammalian left ventricle: underlying molecular, cellular and biophysical mechanisms; Sangita P. Patel and Donald L. Campbell. The Physiological Society 2005.
Improved tools for biological sequence comparison (amino acid/nucleic acid/databse searches/local similarity) Proc. Natl. Acad. Sci. USA; vol. 85, pp 2444-2448, Apr. 1988 Biochemistry.
Chemical synthesis and characterization of ShK toxin: a potent potassium channel inhibitor from a sea anemone. Pennington, et al.; vol. 46, Issue 5, International Journal of Peptide & Protein Research 1995.
Effects of Toxins Pi2 and Pi3 on Human T Lymphocyte Kv1.3 Channels: The Role of Glu7 and Lys24; M. Peter Jr., et al.; The Journal of Membrane Biology 2001.
Tolerance and Contact Sensitivity to DFNB in Mice; I. In vivo detection by ear swelling and correlation with in vitro cell stimulation. Praphan Phanuphak, et al.; The Journal of Immunology 1974.
Scorpion Venom Peptides. Lourival D. Possani and Ricardo C. Rodriguez de la Vega. Handbook of Biologically Active Peptides—Copyright 2006 Elsevier.
Scorpion toxins from *Centruroides noxius* and *Tityus serrulatus* Primary structures and sequence comparison by metric analysis. Lourival D. Possani, et al.; Biochem. J. 1985.
Calcium signaling mechanisms in T lymphocytes. Richard S. Lewis; Annual Reviews 2001.
Crystal structure of a mammalian voltage-dependent shaker family K+ channel. Stephen B. Long, et al.; Science 309, 897 2005.
K channels in T lymphocytes: a patch clamp study using monoclonal antibody adhesion. D.R. Matteson & C. Deutsch; 1984 Macmillan Journals Ltd.
Solid-Phase Peptide Synthesis, 111. An Improved Synthesis of Bradykinin. R. B. Merrifield From the Rockefeller Institute, New York City, 1964.
Charybdotoxin, a protein inhibitor of single $Ca^2$-activated K+ channels from mammalian skeletal muscle. Christopher Miller, et al.; Nature vol. 313, Jan. 24, 1985.
Chemical basis for alkali cation selectivity in potassium-channel proteins. Edward Moczydlowski; Chemistry & Biology; Nov. 1998.
Diversity of folds in animal toxins acting on ion channels. Stephanie Mouhat, et al.; Biochem. J. 2004 378, 717-726 (printed in Great Britain).
The neuroimmunology of multiple sclerosis; possible roles of T and B lymphocytes in immunopathogenesis. Kevin C. O'Conner, et al.; Journal of Clinical Immunology; Mar. 2001.
A molecular link between activation and inactivation of sodium channels. Michael E. O'Leary, et al.; Oct. 1, 1995, The Rockefeller University Press.
Autoimmune lymphoproliferative syndrome: report of two cases and review of the literature. Hale Oren, et al.; Springer-Verlag 2002.

Protein Families and Their Evolution—A Structural Perspective. Christine Orengo & Janet M. Thornton. Copyright 2005 by Annual Reviews.

Ion channels and lymphocyte activation. György Panyi, Zoltán Varga, Rezso Gáspár. Elsevier Immunology Letters 2004.

K+ Channel Blockers: Novel Tools to Inhibit T Cell Activation Leading to Specific Immunosuppression. G. Panyi, L. D. Possani, R.C. Rodriguez de la Vega, R. Gáspár and Z. Varga. Current Pharmaceutical Design, 2006.

Potassium and calcium channels in lymphocytes. Richard S. Lewis; Copyright 1995 by Annual Reviews, Inc.

Ras *CAAX* Peptidomimetic FTI-277 Selectively Blocks Oncogenic Ras Signaling by Inducing Cytoplasmic Accumulation of Inactive Ras-Raf Complexes. Edwina C. Lerner, et al.; The Journal of Biological Chemistry 1995.

International Union of Pharmacology. LIII. Nomenclature and Molecular Relationships of Voltage-Gated Potassium Channels. George A. Gutman, et al.; 2005 The American Society for Pharmacology and Experimental Therapeutics.

Kv1.3 channels are a therapeutic target for T cell-mediated autoimmune diseases. Christine Beeton et al.; PNAS Nov. 14, 2006, vol. 103, No. 46.

Severe chronic graft-versus-host disease is characterized by a preponderance of CD4+ effector memory cells relative to central memory cells. Kouhei Yamashita, et al.; Blood Journal,copyright 2007 by The American Society of Hematology.

Amino acid sequence and immunological characterization with monoclonal antibodies of two toxins from the venom of the scorpion *Centruroides noxius* Hoffmann. Fernando Zamudio et al.; Eur. J. Biochem. 204, 281-292 (1992).

The Mechanism of Inhibition of Ryanodine Receptor Channels by Imperatoxin I, a Heterodimeric Protein from the Scorpion*Pandinus imperator*. Fernando Z. Zamudio, et al.; The Journal of Biological Chemistry 1997.

Evolutionary Trace Analysis of Scorpion Toxins Specific for K-Channels. Shunyi Zhu, et al.; 2003 Wiley-Liss, Inc.

Mitogen-regulated $Ca^{2+}$ current of T lymphocytes is activated by depletion of intracellular $Ca^{2+}$ stores (thapsigargin/patch damp/ inositol trisphosphate receptor/calcium signaling/T-cell activation). Adam Zweifach and Richard S. Lewis. *Proc. Natl. Acad. Sci. USA*, vol. 90, pp. 6295-6299 1993.

GAD65-reactive T cells are activated in patients with autoimmune type 1a diabetes. Vissia Viglietta, et al.; The Journal of Clinical Investigation Apr. 2002.

Mapping of Maurotoxin Binding Sites on hKv1.2, hKv1.3, and hIKCa1 Channels. Violeta Visan, et al.; Molecular Pharmacology 2004.

Delineation of the Clotrimazole/TRAM-34 Binding Site on the Intermediate Conductance Calcium-activated Potassium Channel, IKCa1. Heike Wulf, George A. Gutman, Michael D. Cahalan, George Chandy. The Journal of Biological Chemistry 2001.

The voltage-gated Kv1.3 K+ channel in effector memory T cells as new target for MS. Heike Wulff, et al.; The Journal of Clinical Investigation, Jun. 2003, vol. 111, No. 11.

K+ channel expression during B cell differentiation: Implications for Autoimmunity Immunomodulation and autoimmunity. Heike Wulff, et al.; The Journal of Immunology 2009.

Phaiodactylipin, a glycosylated heterodimeric phospholipase $A_2$ from the venom of the scorpion *Anuroctonus phaiodactylus*. Norma A. Valdez-Cruz, et al.; Eur. J. Biechem. 271, 1453-1464 (2004).

Selective Blockade of Voltage-Gated Potassium Channels Reduces Inflammatory Bone Resorption in Experimental Periodontal Disease. Paloma ValVerde, et al.; Journal of Bone and Mineral Research, vol. 19, No. 1, 2004.

Kv1.3-Blocking 5-Phenylalkoxypsoralens: A New Class of Immunomodulators. Julia Vennekamp, et al.; Copyright 2004 the American Societ for Pharmacology and Experimental Therapeutics.

Quantitative Monitoring of Solid-Phase Peptide Synthesis by the Ninhydrin Reaction. Virender K. Sarin, et al.; Analytical Biochemistry 117, 147-157 (1981).

* cited by examiner

Multiple sequence alignment (CLUSTAL_X)

| Name | Aligned sequences | %I |
|---|---|---|
| Vm24 | AAAISCVGSPECPPKCRAQG -CKNGKCMNRKCKCYYC --- | 100 |
| Vm23 | AAAISCVGS KECLPKCKAQG-CKSGKCMN KKCKCY-C--- | 83 |
| 6.1\|Pi1\|Q10726 | ---VKCRGTSDCGRPCQQQTGCPNSKCINRMCKCYGC --- | 43 |
| 6.2\|Maurotoxin\|P80719 | ---VSCTGSKDCYAPCRKQTGCPNA KCINKSCKCYGC --- | 49 |
| 6.3\|HsTx1\|P59867 | ---ASCRTPKDCADPCRKETGCPYGKCMNRKCKCNRC --- | 46 |
| 6.4\|Pi4\|P58498 | IEAIRCGGSRDCYRPCQKRTGCPNAKCINKTCKCYGCS -- | 45 |
| 6.5\|Pi7\|P58490 | DEAIRCTGTKDCYIPCRYITGCFNSRCINKSCKCYGCT -- | 42 |
| 6.6\|OcKTx1\|AAP73817 | AEVIKCRTPKDCAGPCRKQTGCPHGKCMNRTCRCNRC --- | 46 |
| 6.7\|OcKTx2\|AAP73818 | AEVIKCRTPKDCADPCRKQTGCPHGKCMNRTCRCNRC --- | 46 |
| 6.8\|OcKTx3\|AAP73819 | AEVIKCRTPKDCAGPCRKQTGCPHAKCMNKTCRCHRC --- | 41 |
| 6.9\|OcKTx4\|AAP73820 | AEIIRCSGTRECYAPCQKLTGCLNAKCMNKACKCYGCV -- | 47 |
| 6.10\|OcKTx5\|AAP73821 | AEVIRCSGSKQCYGPCKQQTGCTNSKCMN --CKCYGC--- | 51 |
| 6.12\|Anuroctoxin\|P0C166 | --QKECTGPQHCTNFCRKN -KCTHGKCMNRKCKCFNCK -- | 46 |
| 6.13\|spinoxin\|1v56 | ---IRCSGSRDCYSPCMKQTGCPNAKCINKSCKCYGC --- | 46 |
| 6.14\|HgeTx1 | -TGTSCISPKQCTEPCRAKG -CKHGKCMNRKCHCMLCL -- | 51 |

Phylogenetic tree (MrBayes 3.0b4)

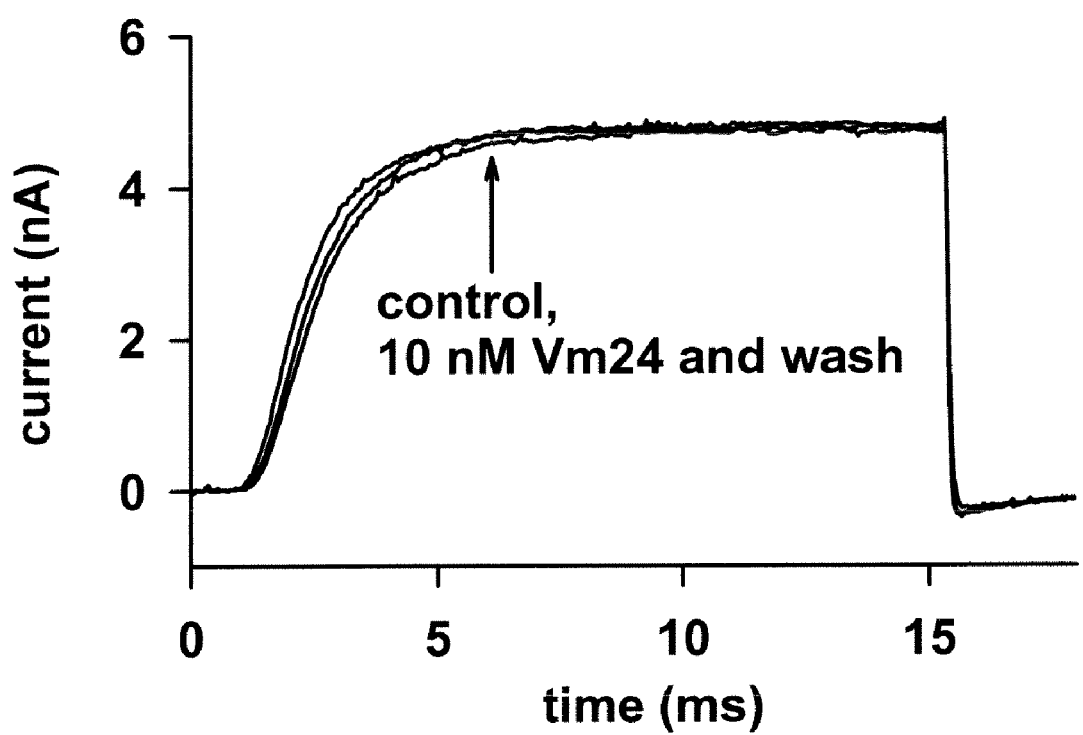

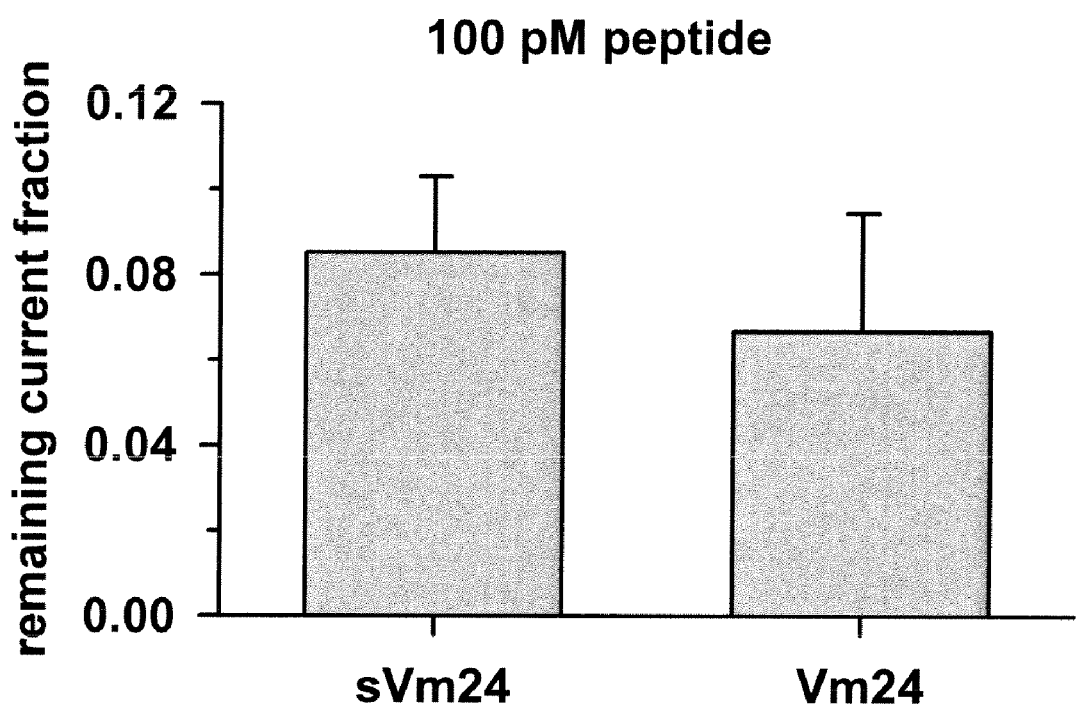

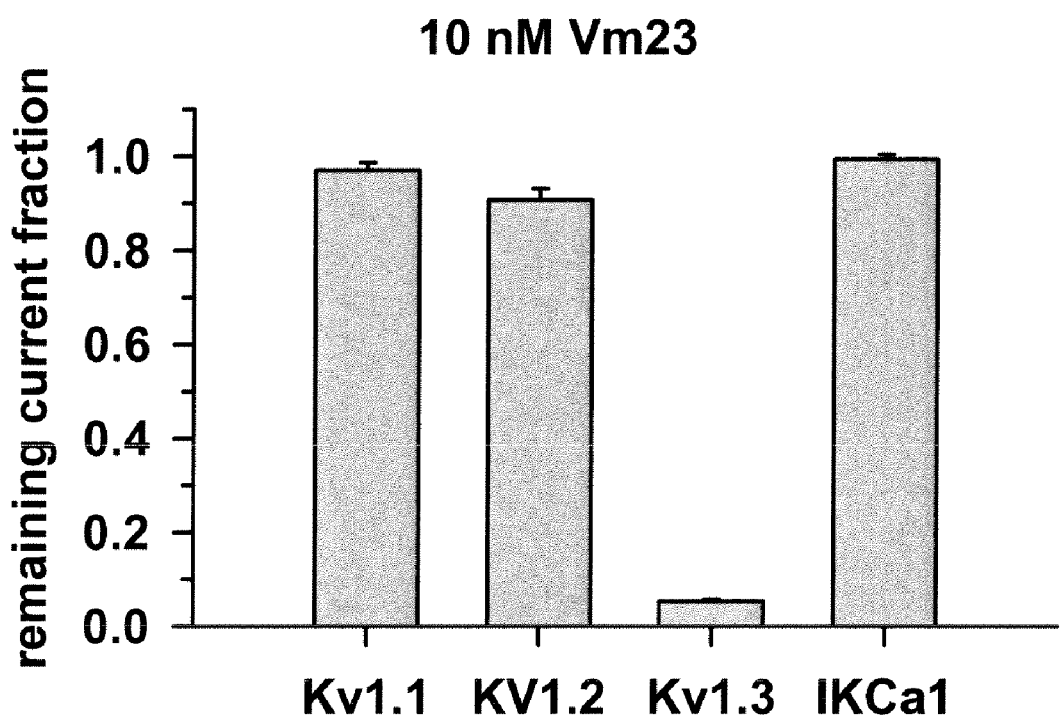

SEQUENCE LISTING

```
<160> NUMBER OF SEQ ID NOS: 17

<210> SEQ ID NO 1
<211> LENGTH: 35
<212> TYPE: PRT
<213> ORGANISM: Vaejovis mexicanus smithi

<400> SEQUENCE: 1

Ala Ala Ala Ile Ser Cys Val Gly Ser Lys Glu Cys Leu Pro Lys Cys
1               5                   10                  15

Lys Ala Gln Gly Cys Lys Ser Gly Lys Cys Met Asn Lys Lys Cys Lys
            20                  25                  30

Cys Tyr Cys
        35

<210> SEQ ID NO 2
<211> LENGTH: 36
<212> TYPE: PRT
<213> ORGANISM: Vaejovis mexicanus smithi

<400> SEQUENCE: 2

Ala Ala Ala Ile Ser Cys Val Gly Ser Pro Glu Cys Pro Pro Lys Cys
1               5                   10                  15

Arg Ala Gln Gly Cys Lys Asn Gly Lys Cys Met Asn Arg Lys Cys Lys
            20                  25                  30

Cys Tyr Tyr Cys
        35

<210> SEQ ID NO 3
<211> LENGTH: 36
<212> TYPE: PRT
<213> ORGANISM: Artificial Sequence
<220> FEATURE:
<223> OTHER INFORMATION: Can be isolated from Vaejovis mexicanus smithi
      or artificially synthesized
<220> FEATURE:
<221> NAME/KEY: MISC_FEATURE
<222> LOCATION: (10)..(10)
<223> OTHER INFORMATION: Xaa can be any amino acid providing it does not
      disrupt the three dimensional folding of the protein or even
      better Lys or Pro
<220> FEATURE:
<221> NAME/KEY: MISC_FEATURE
<222> LOCATION: (13)..(13)
<223> OTHER INFORMATION: Xaa can be any amino acid providing it does not
      disrupt the three dimensional folding of the protein or even
      better Leu or Pro
<220> FEATURE:
<221> NAME/KEY: MISC_FEATURE
<222> LOCATION: (17)..(17)
<223> OTHER INFORMATION: Xaa can be any amino acid providing it does not
      disrupt the three dimensional folding of the protein or even
      better Lys or Arg
<220> FEATURE:
<221> NAME/KEY: MISC_FEATURE
<222> LOCATION: (23)..(23)
<223> OTHER INFORMATION: Xaa can be any amino acid providing it does not
      disrupt the three dimensional folding of the protein or even
      better Ser or Asn
<220> FEATURE:
```

```
<221> NAME/KEY: MISC_FEATURE
<222> LOCATION: (29)..(29)
<223> OTHER INFORMATION: Xaa can be any amino acid providing it does not
      disrupt the three dimensional folding of the protein or even
      better Lys or Arg
<220> FEATURE:
<221> NAME/KEY: MISC_FEATURE
<222> LOCATION: (35)..(35)
<223> OTHER INFORMATION: Xaa can be any amino acid providing it does not
      disrupt the three dimensional folding of the protein or even
      better Tyr or none at all

<400> SEQUENCE: 3

Ala Ala Ala Ile Ser Cys Val Gly Ser Xaa Glu Cys Xaa Pro Lys Cys
1               5                   10                  15

Xaa Ala Gln Gly Cys Lys Xaa Gly Lys Cys Met Asn Xaa Lys Cys Lys
                20                  25                  30

Cys Tyr Xaa Cys
            35

<210> SEQ ID NO 4
<211> LENGTH: 34
<212> TYPE: PRT
<213> ORGANISM: Pandinus imperator

<400> SEQUENCE: 4

Val Lys Cys Arg Gly Thr Ser Asp Cys Gly Arg Pro Cys Gln Gln Gln
1               5                   10                  15

Thr Gly Cys Pro Asn Ser Lys Cys Ile Asn Arg Met Cys Lys Cys Tyr
                20                  25                  30

Gly Cys

<210> SEQ ID NO 5
<211> LENGTH: 34
<212> TYPE: PRT
<213> ORGANISM: Scorpio maurus palmatus

<400> SEQUENCE: 5

Val Ser Cys Thr Gly Ser Lys Asp Cys Tyr Ala Pro Cys Arg Lys Gln
1               5                   10                  15

Thr Gly Cys Pro Asn Ala Lys Cys Ile Asn Lys Ser Cys Lys Cys Tyr
                20                  25                  30

Gly Cys

<210> SEQ ID NO 6
<211> LENGTH: 34
<212> TYPE: PRT
<213> ORGANISM: Heterometrus spinifer

<400> SEQUENCE: 6

Ala Ser Cys Arg Thr Pro Lys Asp Cys Ala Asp Pro Cys Arg Lys Glu
1               5                   10                  15

Thr Gly Cys Pro Tyr Gly Lys Cys Met Asn Arg Lys Cys Lys Cys Asn
                20                  25                  30

Arg Cys

<210> SEQ ID NO 7
<211> LENGTH: 38
<212> TYPE: PRT
<213> ORGANISM: Pandinus imperator

<400> SEQUENCE: 7

Ile Glu Ala Ile Arg Cys Gly Gly Ser Arg Asp Cys Tyr Arg Pro Cys
```

```
                1               5              10              15
Gln Lys Arg Thr Gly Cys Pro Asn Ala Lys Cys Ile Asn Lys Thr Cys
            20                  25                  30

Lys Cys Tyr Gly Cys Ser
        35

<210> SEQ ID NO 8
<211> LENGTH: 38
<212> TYPE: PRT
<213> ORGANISM: Pandinus imperator

<400> SEQUENCE: 8

Asp Glu Ala Ile Arg Cys Thr Gly Thr Lys Asp Cys Tyr Ile Pro Cys
1               5                   10                  15

Arg Tyr Ile Thr Gly Cys Phe Asn Ser Arg Cys Ile Asn Lys Ser Cys
            20                  25                  30

Lys Cys Tyr Gly Cys Thr
        35

<210> SEQ ID NO 9
<211> LENGTH: 37
<212> TYPE: PRT
<213> ORGANISM: Opistophthalmus carinatus

<400> SEQUENCE: 9

Ala Glu Val Ile Lys Cys Arg Thr Pro Lys Asp Cys Ala Gly Pro Cys
1               5                   10                  15

Arg Lys Gln Thr Gly Cys Pro His Gly Lys Cys Met Asn Arg Thr Cys
            20                  25                  30

Arg Cys Asn Arg Cys
        35

<210> SEQ ID NO 10
<211> LENGTH: 37
<212> TYPE: PRT
<213> ORGANISM: Opistophthalmus carinatus

<400> SEQUENCE: 10

Ala Glu Val Ile Lys Cys Arg Thr Pro Lys Asp Cys Ala Asp Pro Cys
1               5                   10                  15

Arg Lys Gln Thr Gly Cys Pro His Gly Lys Cys Met Asn Arg Thr Cys
            20                  25                  30

Arg Cys Asn Arg Cys
        35

<210> SEQ ID NO 11
<211> LENGTH: 37
<212> TYPE: PRT
<213> ORGANISM: Opistophthalmus carinatus

<400> SEQUENCE: 11

Ala Glu Val Ile Lys Cys Arg Thr Pro Lys Asp Cys Ala Asp Pro Cys
1               5                   10                  15

Arg Lys Gln Thr Gly Cys Pro His Ala Lys Cys Met Asn Lys Thr Cys
            20                  25                  30

Arg Cys His Arg Cys
        35

<210> SEQ ID NO 12
<211> LENGTH: 38
<212> TYPE: PRT
```

<213> ORGANISM: Opistophthalmus carinatus

<400> SEQUENCE: 12

Ala Glu Ile Ile Arg Cys Ser Gly Thr Arg Glu Cys Tyr Ala Pro Cys
1               5                   10                  15

Gln Lys Leu Thr Gly Cys Leu Asn Ala Lys Cys Met Asn Lys Ala Cys
            20                  25                  30

Lys Cys Tyr Gly Cys Val
            35

<210> SEQ ID NO 13
<211> LENGTH: 29
<212> TYPE: PRT
<213> ORGANISM: Opistophthalmus carinatus

<400> SEQUENCE: 13

Ala Glu Val Ile Arg Cys Ser Gly Ser Lys Gln Cys Tyr Gly Pro Cys
1               5                   10                  15

Lys Gln Gln Thr Gly Cys Thr Asn Ser Lys Cys Met Asn
            20                  25

<210> SEQ ID NO 14
<211> LENGTH: 6
<212> TYPE: PRT
<213> ORGANISM: Opistophthalmus carinatus

<400> SEQUENCE: 14

Cys Lys Cys Tyr Gly Cys
1               5

<210> SEQ ID NO 15
<211> LENGTH: 35
<212> TYPE: PRT
<213> ORGANISM: Anuroctonus phaiodactylus

<400> SEQUENCE: 15

Gln Lys Glu Cys Thr Gly Pro Gln His Cys Thr Asn Phe Cys Arg Lys
1               5                   10                  15

Asn Lys Cys Thr His Gly Lys Cys Met Asn Arg Lys Cys Lys Cys Phe
            20                  25                  30

Asn Cys Lys
            35

<210> SEQ ID NO 16
<211> LENGTH: 34
<212> TYPE: PRT
<213> ORGANISM: Heterometrus spinifer

<400> SEQUENCE: 16

Ile Arg Cys Ser Gly Ser Arg Asp Cys Tyr Ser Pro Cys Met Lys Gln
1               5                   10                  15

Thr Gly Cys Pro Asn Ala Lys Cys Ile Asn Lys Ser Cys Lys Cys Tyr
            20                  25                  30

Gly Cys

<210> SEQ ID NO 17
<211> LENGTH: 36
<212> TYPE: PRT
<213> ORGANISM: Hadrurus gertschi

<400> SEQUENCE: 17

Thr Gly Thr Ser Cys Ile Ser Pro Lys Gln Cys Thr Glu Pro Cys Arg

```
                1               5                    10                  15
        Ala Lys Gly Cys Lys His Gly Lys Cys Met Asn Arg Lys Cys His Cys
                                20                  25                  30
        Met Leu Cys Leu
                35
```

VM23 AND VM24, TWO SCORPION PEPTIDES THAT BLOCK HUMAN T-LYMPHOCYTE POTASSIUM CHANNELS (SUB-TYPE KV1.3) WITH HIGH SELECTIVITY AND DECREASE THE IN VIVO DTH-RESPONSES IN RATS

A sequence listing has been submitted in an ASCII text file with the name "Amended Sequence_Listing_ST25.txt", having a date of creation of Nov. 1, 2012, and a size of 8275 bytes. This sequence listing is hereby incorporated by reference.

FIELD OF THE INVENTION

The present invention relates generally to the fields of biochemistry, molecular biology, immunology and electrophysiology. Disclosed are peptides, their pharmaceutical compositions, and methods for their use to block Kv1.3 potassium channels, for the treatment of various immunological conditions and for diagnostic applications, and methods for the chemical synthesis and correct folding procedures for peptides corresponding to two protein components isolated from the venom of the Mexican scorpion *Vaejovis mexicanus smithi* (here abbreviated thereafter: *V. mexicanus*), which constitute a new sub-family of potassium channel specific ligands, capable of blocking with high affinity and specificity a sub-type of potassium channels (hKv1.3) shown to be implicated in immunological diseases and graft rejections. Methods and techniques used for their chemical and functional characterization are disclosed, as well as the results of in vivo experiments on the DTH-response of sensitized rats when treated with Vm24. This peptide (Vm24), its homologous Vm23 and their functional equivalent analogs are lead compounds, candidates for the treatment of various immunological conditions and diagnostic applications.

BACKGROUND OF THE INVENTION

General Considerations

Several aspects should be taken into consideration concerning the subject of the invention reported here, among which are the important advances in the fields of biochemistry, molecular biology, immunology and electrophysiology related to the knowledge generated about:

1) —the presence of integral proteins of biological membranes termed "ion-channels" playing a fundamental role in cellular communication, signal transduction pathways and general homeostasis of tissues and various organ functions;
2) —different levels of expression of these channels in cells of the immune system, mainly in T-lymphocytes, shown to play a clear role in events related to the onset of autoimmune diseases;
3) —the possible control of the channel function, hence possible treatment of disorders, through the addition of various chemicals, natural ligands and synthetically prepared substances, either reproducing the ligand as found in nature or preparing similar derivatives (peptidomimetics).

A multitude of potassium (K) channels have been discovered and reported to exist in the last fifteen years permitting their isolation, individual expression and functional analysis.

They are multimeric proteins implicated in the determination of cell membrane potential, thereby controlling smooth muscle tone, synaptic excitability, neurotransmitter release, and other processes. In this invention we want to emphasize the importance of a K channel species, sub-type Kv1.3, and its role in lymphocyte proliferation and in the control of autoimmune diseases by means of inhibiting this channel. This is a delayed-rectifier channel predominantly expressed in T lymphocytes [Grissmer et al., 1990; Lewis and Cahalan, 1995], different from the sub-types Kv1.1, Kv1.2 widely distributed in brain or Kv1.5 in heart tissue, to mention just a few of the sub-types of K channels.

The mechanisms by which modulation of Kv1.3 channels activity affects lymphocyte proliferation are being investigated in several laboratories and were the object of many recent publications (reviewed in [Beeton and Chandy, 2005; Judge and Bever, 2006, Panyi et al., 2006], including some patents (v.gr. U.S. Pat. No. 5,397,702 by Cahalan et al. 1995 and U.S. Pat. No. 6,077,680 by Kem et al. 2000).

Autoimmune diseases are known for their considerable worldwide morbidity. Among these diseases are: type-1 diabetes mellitus (insulin dependent), multiple sclerosis (MS), rheumatoid arthritis, Sjogren's syndrome, mixed connective tissue disease, systemic lupus erythematosus (SLE), myasthenia gravis, to mention just some of them. A relevant experimental model for autoimmune diseases is the experimental autoimmune encephalomyelitis (EAE). It is generally accepted that these autoimmune diseases result from the response of the immune system destroying specific tissues, either by a direct attack to the cells, or by producing autoantibodies. The over-expression of Kv1.3 channels is a characteristic feature of autoreactive T cells thereby providing an excellent opportunity for the modification of their proliferation by blockers of Kv1.3.

In these lines of research and experimentation, several substances were described and even patented. One such example is the toxin ShK from the sea anemone *Stichodactyla helianthus* and several derivatives of it, claimed to have a protective effect against several autoimmune diseases (v.gr. U.S. Pat. No. 6,077,680 by Kem et al. 2000).

Among other natural ligands that are capable of affecting the function of ion-channels are toxic peptides isolated from scorpion venoms. K channel specific peptides isolated from these venoms are short-chain peptides containing 22 to 42 amino acids compacted by either three or four disulfide bridges. They are blockers of many different sub-types of channels, with a huge variability in selectivity and affinity (reviewed in [Giangiacomo et al., 2004; Rodriguez de la Vega and Possani, 2004]). For example, charybdotoxin is a potent blocker of Kv1.1, Kv1.2 and 1.3 Shaker type delayed rectifier channels but also blocks maxi-type K(Ca) channels [Rauer et al., 2000]. Margatoxin, another scorpion venom peptide, lacks K(Ca) channel blocking activity, but maintains a high affinity block of Kv1.3 channels. [Garcia-Calvo et al., 1993]. Agitoxin, noxiustoxin, kaliotoxin are examples of scorpion toxins that affect different types of K channels with distinct affinities and selectivities, but usually modify more than one sub-types of channels (recent reviewed in [Panyi et al., 2006]). Due to their relatively rigid three-dimensional structure, tightly maintained by disulfide bridges, some of these scorpion peptides have been used as "molecular calipers" for measuring distances between K channel amino acid residues in the outer vestibule of the channels [Krezel et al., 1995; Garcia et al., 2000]. The three dimensional structure of many scorpion toxins specific for K channels was resolved by nuclear magnetic resonance and/or X-ray diffraction methods, and in conjunction with the known structure of some K channels have provided the clue to model the interaction between the receptor (ion-channel) and the ligand (scorpion toxin). Site-directed mutagenesis of amino acid residues in both the ion-channels and the ligands has provided information for the identification of the putative interaction surface among this pair of receptor-ligand proteins [Rodriguez de la Vega et al., 2003]. This information is fundamental for the rational design of possible drugs with potential pharmacological applications. The only problem in using these naturally occurring peptides as potential drugs is the lack of specificity and affinity. At present, there are 20 sub-families of scorpion toxins, comprising over 125 structurally related peptides, classified by their sequence similarities and possible functions [Tytgat et al., 1999; Rodriguez de la Vega and Possani, 2004].

Molecular Basis for Kv1.3 Inhibitor-Based Therapy of Autoimmune Diseases

In this section the inventors present the state of the art knowledge on the control of several immunological diseases by simple application of ligands (peptides or organic compounds) capable of blocking with high affinity and high specificity the Kv1.3 ion-channels of "effector memory T-cells" ($T_{EM}$) of lymphocytes.

It has been shown earlier that the mechanism by which Kv1 3 inhibitors interfere with the activation processes of lymphocytes evoked by physiological antigen stimulation or mitogens is the depolarization of the membrane and the consequent inhibition of the $Ca^{2+}$ signal required for normal progression of the cell cycle to proliferation and production of the T-cell clones specific for a challenging antigen (reviewed in [Cahalan et al., 2001; Panyi et al., 2004; Panyi et al., 2006]). There are two types of K channels being responsible for maintaining a sufficiently hyperpolarized membrane potential (−50, −60 mV) [Verheugen et al., 1995] of T cells, the voltage-gated and depolarization activated channel denoted as Kv1.3 [Decoursey et al., 1984; Matteson and Deutsh, 1984]; and the $Ca^{2+}$-activated K channel of intermediate conductance denoted as IKCa1 (or $K_{Ca}3.1$. according to a recent nomenclature) [Grissmer et al., 1993]. The activity of these channels provides the counterbalancing positive charge efflux required for the maintenance of a negative membrane potential during the influx of $Ca^{2+}$ into the T cells through the $Ca^{2+}$ release activated $Ca^{2+}$ channels [Feske et al., 2006; Yeromin et al., 2006]. The contribution of these two types of K channels to the membrane potential of T cells depends on the activation status of the cells (resting vs. activated) and their functional role in the immune system determined by the degree of terminal differentiation of the T cells, as discussed below [Wulff et al., 2003].

Two types of T cells, the naïve and central memory T cells ($T_{CM}$), require strong antigen stimulation and co-stimulation in peripheral (secondary) lymphoid organs to be activated. The naïve T cells that have not encountered previously an antigen bear $CCR7^+CD45RA^+$ functional marker expression. Central memory T cells ($T_{CM}$, $CCR7^+CD45RA^-$), which cells mediate reactive memory, are probably arrested at intermediate stages of terminal differentiation to become effector memory cells ($T_{EM}$) [Sallusto et al., 2004]. These cells have little or no effector function, but readily proliferate and differentiate to effector cells in response to antigenic stimulation. Protective memory is governed by effector memory $T_{EM}$ cells ($CCR7^-CD45RA^{+/-}$). $T_{EM}$ cells display characteristic sets of chemokine receptors and adhesion molecules that are required for homing to inflamed tissues where they exert immediate effector function. In several autoimmune diseases, including multiple sclerosis (MS) (Wulff et al., 2003), rheumatoid arthritis and type-I diabetes mellitus [Beeton et al., 2006], autoimmune psoriasis, lupus erythematosus, ulcerative colitis, sympathetic ophtalmia and bone resorption periodontal disease, chronically activated $T_{EM}$ cells are responsible for tissue damage, thus selective inhibition of the proliferation and functional activity of these cells is of utmost importance in the management of these diseases (reviewed in [Chandy et al., 2004; Beeton and Chandy, 2005; Panyi et al., 2006].

Resting human naïve, $T_{CM}$ and $T_{EM}$ of either $CD4^+$ (helper) or $CD8^+$ (cytotoxic) phenotype express similar number (200-300) of Kv1.3 and fewer than 30 IKCa1 channels per cell [Wulff et al., 2003]. Transformation of naïve and $T_{CM}$ cells to proliferating blast cells by specific antigen stimulation is accompanied by a modest (~1.5-fold) increase in the number of Kv1.3 channels per cell, whereas the number of IKCa1 channels increase dramatically (500 channel/cell) and thus, they acquire an $IKCa1^{high}Kv1.3^{low}$ ion channel phenotype. In contrast, activation of $T_{EM}$ of either $CD4^+$ or $CD8^+$ phenotype in the peripheral tissues is accompanied by a dramatic increase in the number of Kv1.3 channels to ~1500/cell without any change in the IKCa1 level thereby the channel phenotype of activated $T_{EM}$ becomes $IKCa1^{low}Kv1.3^{high}$.

The causal link between $Kv1.3^{high}$ $T_{EM}$ and autoimmune disorders is substantiated by the following data obtained in human diseases:
1) myelin-reactive T cells from the peripheral blood of MS patients are $Kv1.3^{high}$ [Wulff et al., 2003];
2) myelin-reactive T cells from the peripheral blood of healthy controls are $Kv1.3^{low}$, consistent with a naïve/$T_{CM}$ phenotype;
3) stimulation of MS patient T cells with irrelevant antigens such as insulin peptide, ovalbumin or with conventional mitogens did not induce the generation of $T_{EM}$ with $Kv1.3^{high}IKCa1^{low}$ channel phenotype;
4) $Kv1.3^{high}$ $T_{EM}$ cells were shown in postmortem MS brain inflammatory infiltrates and in the parenchyma of demyelinated MS lesions [Rus et al., 2005];
5) T cells isolated from the synovial fluid of human patients suffering from Rheumatoid Arthritis (RA) express large amounts of Kv1.3 as compared to T cells of the same donor but isolated from peripheral blood. These $Kv1.3^{high}$ T cells were $CCR7^-$ indicating that they are $T_{EM}$ cells [Beeton et al., 2006];
6) Short term antigen specific $CD4^+$ T cell lines (TCLs) generated from peripheral blood lymphocytes of Type 1 Diabetes Mellitus (T1DM) human patients and specific for T1DM-associated autoantigens insulin and GAD65 display the characteristic features of $T_{EM}$ cells including the lack of CCR7 antigen ($CCR7^-$) and $Kv1.3^{high}$ channel phenotype [Beeton et al., 2006].

As the membrane potential control of $T_{EM}$ cells is exclusively governed by the activity of Kv1.3 channels, the proliferation of these cells, their functional activity, and thus the symptoms of the autoimmune disease, should be ameliorated by the use of Kv1.3 inhibitors. The following in vitro and in vivo data in the literature support this scenario:
1) In vitro proliferation of chronically activated human T cell lines bearing the characteristics of $T_{EM}$ ($CCR7^-$, $Kv1.3^{high}$) and specific for myelin antigen [Wulff et al., 2003] or $T_{EM}$ cells isolated from the synovial fluid of RA patients is completely and permanently suppressed by Kv1.3 specific blockers peptide such as ShK [Wulff et al., 2003], ShK(L5) or by the small-molecule Kv1.3 blocker PAP-1 [Beeton et al., 2006];
2) In vivo experiments with Margatoxin, another high affinity Kv1.3 blocker peptide, showed that block of Kv1.3 leads to the inhibition of delayed-type hypersensitivity reactions in miniswine; this reaction is a good measure of the activity of effector memory T cells [Koo et al., 1997];
3) Treatment of MBP-specific rat T cells with ShK or ShK-$Dap^{22}$ during their in vitro stimulation with MBP (sensitization phase) along with repeated application of the peptides into the recipient animals (during the effector phase) prevented the adoptive transfer of Experimental Autoimmune Encephalomyleitis (AT-EAE) into Lewis rats [Beeton et al., 2001]. EAE in rats [Ben Nun and Cohen, 1982], is the best characterized model for the human disease MS characterized by similar pathogenesis and neurological abnormalities, and the disease causing T cell population is the myelin-specific $T_{EM}$ having Kv1.3$^{high}$ channel phenotype. The combined application of Kv1.3 and IKCa1 channel blockers also ameliorated the symptoms of EAE when administered following its onset [Beeton et al., 2001];

4) Pristane-induced MHC class II-restricted chronic arthritis model (PIA) in Dark Agouti rats is a rat model for the human disease Rheumatoid Arthritis. Single daily injections of ShK(L5) significantly reduced the number of joints affected by the disease during the trial period (up to 34 days) [Beeton et al., 2006];

5) The efficacy of a Kv1.3 inhibitor to prevent experimental autoimmune diabetes (EAD, a rat model for T1DM of humans) was studied in MHC class II-restricted DP-BB/W rats [Beeton et al., 2006]. It was shown that repeated daily administration of PAP-1, a high affinity and selectivity small-molecule blocker of Kv1.3 reduced the fraction of rats showing the symptoms of EAD by ~50% (assayed at 110 days of age) as compared to control animals treated with vehicle only. This was accompanied by a decreased intraislet T cell and macrophage infiltration and reduced β cell destruction in the PAP-1-treated group as compared with vehicle-treated control (assayed between 35-70 days of age) [Beeton et al., 2006].

The inhibition of T cell proliferation by Kv1.3-specific inhibitors is specific to $T_{EM}$ cells, which makes these compounds ideal tools for the management or prevention of autoimmune diseases. Although antigen-induced proliferation of resting naïve and $T_{CM}$ cells is partially sensitive to Kv1.3-mediated inhibition, the transcriptional up-regulation of IKCa1 channels overcomes this in pre-activated T cells and renders the proliferation of these cells to be sensitive to IKCa1 inhibitors but not to Kv1.3 inhibitors [Ghanshani et al., 2000]. This restricted action of Kv1.3 and IKCa1 inhibitors on different T cell subsets underlies the importance of the selectivity of a given molecule for Kv1.3 over IKCa1. It was also shown recently that the inhibition of $T_{EM}$ proliferation by Kv1.3 inhibitors can be overcome by excessive antigen stimulation mimicking the activation of $T_{EM}$ cells by pathogens and vaccine antigens during normal protective memory immune reactions [Beeton et al., 2006]. Thus, the application of high affinity and high selectivity Kv1.3 inhibitors ideally targets $T_{EM}$ cells repeatedly activated during autoimmune reactions whereas leave other protective functions of the immune system unaltered.

In addition to human T and B lymphocytes Kv1.3 channels are also expressed in several organs and tissues (including the central nervous system, kidney, liver, skeletal muscle), and the block of Kv1.3 channels in the cells may give rise considerable side effects. Extensive in vitro and acute and chronic in vivo toxicological tests were performed previously for ShK(L5) [Beeton et al., 2005; Beeton et al., 2006] from the peptide blockers group and for PAP-1 [Schmitz et al., 2005; Beeton et al., 2006] from the group of small molecule blockers. These studies showed the lack of clinical symptoms for neurological and cardiac side effects or histopathological changes in tissues where Kv1.3 is expressed. Thus, the beneficial treatment-effects of Kv1.3 blockers listed above combined with minimal or the complete absence of side effects point towards the applicability of selective Kv1.3 blockers in the management of autoimmune diseases.

In summary, data above suggest a critical role of Kv1.3 K channels in the execution of a physiological immune response, and point to the applicability of a therapeutic intervention in autoimmune disease by the inhibition of Kv1.3 channels.

SUMMARY OF THE INVENTION

The present invention concerns the identification and use of novel peptides isolated from the venom of the Mexican scorpion *V. mexicanus*: Vm23, Vm24 and their functional equivalent analogs, which are capable of inhibiting the function of hKv1.3 channels from human lymphocytes with high affinity and specificity, by blocking a specific ion conductance. In other embodiments of the present invention, the inventors disclose pharmaceutical compositions comprising Vm23, Vm24 and their functional equivalent analogs, methods for their use to block Kv1.3 potassium channels, to treat various immunological conditions and to diagnostic applications and methods for their chemical synthesis and correct folding. These peptides were isolated by means of conventional high performance liquid chromatography and have had their primary amino acid sequence determined by Edman degradation and mass spectrometry, showing the primary structure shown in SEQ ID NO:1 and SEQ ID NO:2. Vm24 contains 36 amino acids with a molecular weight of 3863.5 Daltons. It is a compact molecule maintained by four disulfide bridges established by mass spectrometry to be between pairs of cysteines at positions C6 and C26, C12 and C31, C16 and C33, and C21 and C36, where the letter C stands for the abbreviation of cysteine residues and the numbers correspond to their relative positions into the amino acid sequence. The amino acid at the carboxylic end of the peptide is amidated. The full peptide was chemically synthesized using the solid phase method of Merrifield and the correct folding of the synthetic peptide was obtained and confirmed by both chemical and functional analysis. Vm24 is not toxic to mice when injected at relatively high concentration (assayed up to 200 micrograms per mouse of 20 grams body weight, that is: 10,000 microgram/kilogram mouse weight). When applied to human lymphocytes in vitro, it shows an extremely high affinity for hKv1.3 channels assayed by the patch-clamp technique. It binds to these channels in an almost irreversible manner, showing a Kd value in the lower picomolar range (less than 3 picomolar—3 pM). It does not modify the potassium currents of the following ion channels: hKv1.4, hKv1.5, rKv2.1, hBK and hERG-channel, and the currents of the voltage-gated cardiac Na$^+$ channel (hNa$_V$1.5) when assayed at a concentration of 10 nanomolar (10 nM). The current inhibition at 10 nM concentration for channels hIKCa1, mKv1.1 and hKv1.2 is approximately 20 to 50%, as opposed to 100% blockage for hKv1.3 channels. The toxin blocks over 50% of the hKv1.3 current at a concentration as low as 3 pM, thus being approximately 1500-fold more effective on this channel than any of the other channels assayed.

Lethality tests conducted with Vm24 caused no observable symptoms of intoxication using concentrations up to 200 microgram/20 gram mouse weight. Vm24 applied to the rat model for delayed-type hypersensitivity (DTH) protected the experimental animals Skin sensitization of experimental rats with dinitrofluorobenzene (DNFB) causes a considerable immunological response (redness and gross inflammation of ears). Groups of rats subjected to a single injection of 10 micrograms of Vm24 on day six after starting the treatment show a considerable attenuation of the immune response; the inflammation of the treated ears is significantly decreased (at least 60% less inflammation) compared to control rats that received only solvent treatment.

A related peptide named Vm23, was also isolated from the same venom and completely sequenced, as shown in SEQ ID NO:1. This peptide is 83% identical to Vm24, has 35 amino acid residues, packed by four disulfide bridges, and shows a molecular weight of 3665 Daltons. Vm23 displays equivalent function as Vm24: high affinity and specificity for hKv1.3 channels. The blockage of the currents for channels hKv1.3, hIKCa1, mKv1.1 and hKv1.2 at 10 nM concentration of Vm23 were approximately 95%, 1%, 3% and 9%, respectively.

Phylogenetic analysis conducted with both peptides using more than 125 other known scorpion peptides [Bagdany et al., 2005], specific for K channels, showed that Vm23 and Vm24 do not fall within any of the 20 sub-families of already described scorpion toxin structures. They are the first two examples of a new structural sub-family, here proposed to be named: α-KTx 21. Vm24 and Vm23 thus should be named α-KTx 21.1 and α-KTx 21.2, respectively. Among the criteria used to define new sub-families of scorpion toxins specific for K channels, according to an international panel of scientists that set the systematic nomenclature now in use (see [Tytgat et al., 1999]), are the need for the primary structure to be different by at least 50% of the others. In fact, both Vm23 and Vm24 show less than about 50% sequence similarity with the other known toxins.

Based on the state of art knowledge of the field, these properties make Vm23, Vm24 and their functional equivalent analogs, excellent candidates for immune suppression and the diagnosis and treatment of immunological diseases.

BRIEF DESCRIPTION OF THE DRAWINGS

The drawings included in this disclosure form part of the present specification and are included here to further demonstrate certain aspects of the present invention. The full invention may be better understood by complementing one or more of these drawings with the detailed description of specific embodiments presented herein, especially in the section of the examples below.

FIG. 1: HPLC separation of 1 mg of the soluble venom from the scorpion *V. mexicanus*. More than 80 different components were separately obtained by application of the soluble venom into a C18 reverse phase column (catalog number 218TP54 from Vydac, Hisperia, Calif.) equilibrated with solution A (water in 0.10% TFA), using a gradient from 0% to 60% solution B (acetonitrile in 0.12% TFA) over 60 min Numbers 1 and 2 at retention times 23 and 24 min indicates the elution position of Vm23 and Vm24, respectively. An additional separation of each one of these two chromatographic fractions was conducted in the same system, but using a linear gradient from solution A to 40% solution B, during 60 min for both peptides. The results are shown as inset of the figure. The asterisks in the insets indicate position of elution of highly purified peptides.

FIG. 2: Amino acid sequence of Vm23, Vm24 and consensus. The sequences of Vm23 (SEQ ID NO: 1) and Vm24 (SEQ ID NO: 2) were obtained by direct Edman degradation of native peptides and reduced and alkylated samples, in combination with mass spectrometry analysis of peptides obtained by enzymatic cleavage of pure peptide with specific enzymes (endoprotease Arg-C and Lys-C), as indicated below the corresponding sequences. The amino acid sequences of the peptides purified after enzymatic hydrolysis and HPLC separation were identified by mass spectrometry analysis (MS/MS, means mass spectrometry fragmentation by electro-spray ionization). Under each sequence are the indications of the segments identified by the various methods used. Direct means Edman degradation, Arg-C and Lys-C are the fragments purified after enzymatic digestion. MS alone means identification based on molecular mass of the missing amino acid. The consensus sequence (SEQ ID NO: 3) has 30 amino acid residues which are identical to those of Vm23 or Vm24. The positions labeled as "x" could be: $x^1$, any amino acid providing it does not disrupt the three dimensional folding of the protein or even better K or P; $x^2$, any amino acid providing it does not disrupt the three dimensional folding of the protein or even better L or P; $x^3$, any amino acid providing it does not disrupt the three dimensional folding of the protein or even better K or R; $x^4$, any amino acid providing it does not disrupt the three dimensional folding of the protein or even better S or N; $x^5$, any amino acid providing it does not disrupt the three dimensional folding of the protein or even better K or R, and; $x^6$, any amino acid providing it does not disrupt the three dimensional folding of the protein or even better Y or none at all.

FIG. 3: Vm24 possesses an amidated C terminal. Collisional-Induced Dissociation (CID) of the C-terminal $[M+H]^+$ ion at m/z 909.4 a.m.u. (monoisotopic molecular weight) shows 1.0 unit less than the expected theoretical value of [M+H].sup.+ 910.5 a.m.u. The y ion series (italic) corresponding to an amidated C-terminal sequence KCKCYYC (residues 30-36 of SEQ ID NO: 2) is shown in the insert labeled 1). Theoretical y ion series values for free-carboxy-terminal peptide (TV-COOH), theoretical y ion series values for amidated C-terminal (TV-$NH_2$) and experimental y ion series values (EXP.) are compared in the table inserted (insert labeled 2).

FIG. 4: Vm24 heterodimers for disulfide assignment. The numbers 1 and 2 show the molecular weights and schematic structures of the heterodimers produced by simultaneous proteolytic cleavage of Vm24 using trypsin and chymotrypsin at pH 6.5. The [M+H].sup.+ion at m/z 788.0 a.m.u. corresponds to the molecular mass of the heterodimer containing the cystine half-pair C4-C8 (number 1), with AQGCK corresponding to a residues 18-22 of SEQ ID NO: 2 and YC corresponding to residues 35-36 SEQ ID NO: 2, and the $[M+H]^+$ ion at m/z 560.4 a.m.u. to the cystine half-pair C3-C7 (number 2), with CR corresponding to residues 16-17 of SEQ ID NO: 2 and CY corresponding to residues 33-34 of SEQ ID NO: 2.

FIG. 5: Vm24 cystine half-pairs. A) Mass spectrum corresponding to the structure of the complex core containing both cystine half-pairs, C1-C4 and C2-C6 with $[M+2H]^{+2}$ ion at m/z 1099.7 a.m.u. The sequence AAAISCVGSPECPPK corresponds to residues 1-15 of SEQ ID NO: 2. The sequence CMNR corresponds to residues 26-29 of SEQ ID NO: 2. The sequence CK corresponds to residues 31-32 of SEQ ID NO: 2. This was fragmented to produce the MS/MS spectrum shown in FIG. 4B. The b ion series values from 1137 to 1507 a.m.u. unequivocally represent the tag GSPE confirming the assignment of the last two cystine half-pairs. B). Shows the full disulfide bridges arrangement of Vm24(SEQ ID NO: 2), as determined by mass spectrometry analysis described in part A of this figure.

FIG. 6: HPLC purification of synthetic Vm24. Synthetically prepared Vm24 (50 milligram protein) was separated in a C18 reverse phase preparative column. Number 1 indicates the elution position of synthetic and correctly folded Vm24, whereas 2 and 3 indicate incorrectly folded or truncated sequences. An additional separation of this chromatographic fraction was conducted in the same system, but using an analytical column developed with a linear gradient from solution A to 40% solution B, during 60 min. The results are shown as inset of the figure.

Figure 7:
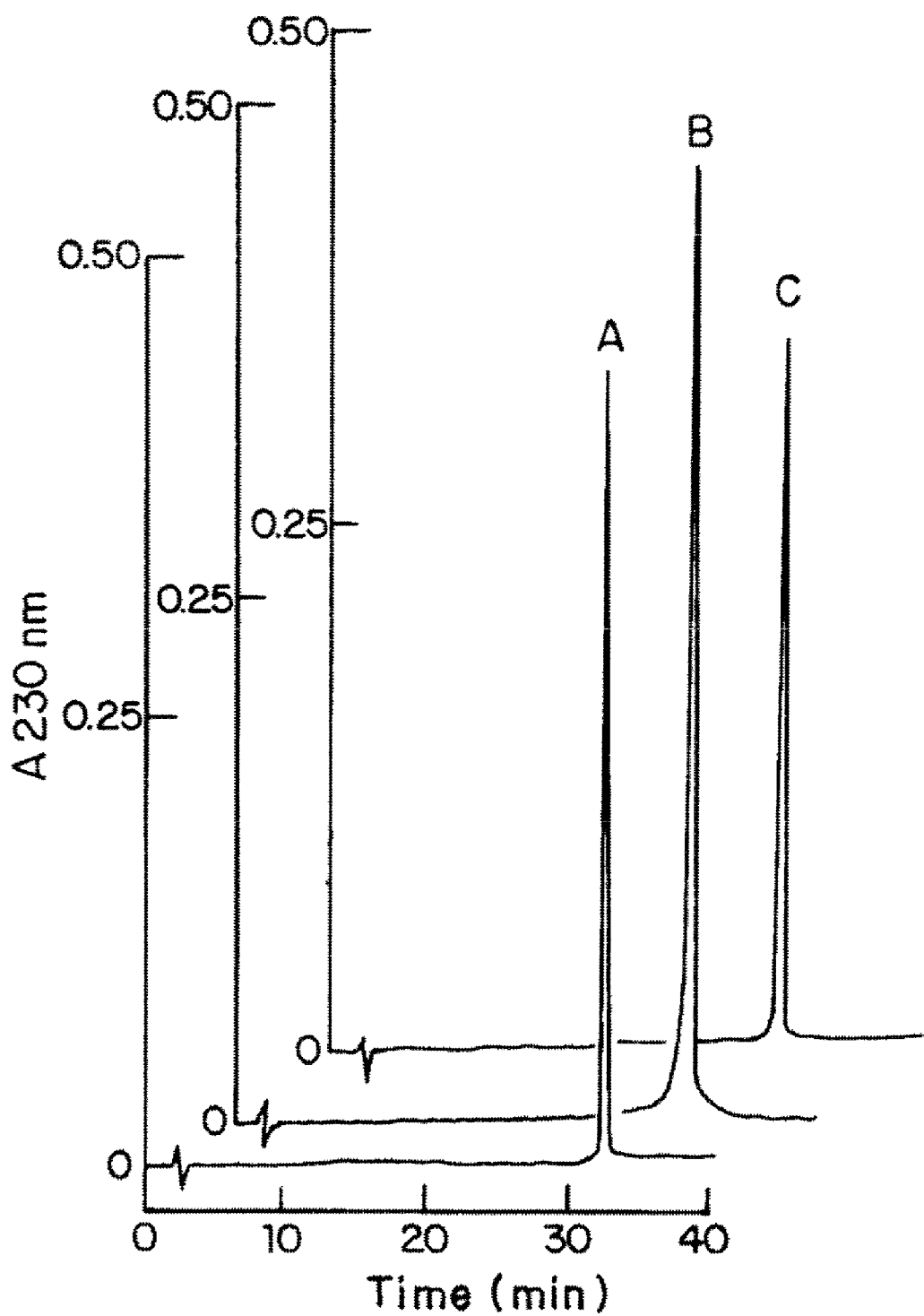

FIG. 7: HPLC comparison of synthetic and natural Vm24 peptide. A) Application of 10 micrograms of native Vm24 into an analytical C18 column (catalog number 218TP54 from Vydac, Hisperia, Calif.) in the system of HPLC described in FIG. 1 shows that the pure peptide elutes at 32.67 min, when developed with a linear gradient from solution A to 40% solution B, during 60 min B) Chromatogram of 15 micrograms of synthetically prepared and folded Vm24 in the same system and conditions. C) Co-injection of a 1:1 mixture of synthetic and natural Vm24 (total 8 micrograms) showing that they co-elute at the same retention time. It is worth mentioning that the X-axis of the graph is shifted to the right for letters B and C, in order that the three graphs could be observed comparatively, but separately, otherwise the elution times of the three independent HPLC runs would fall into the same peak, and become undistinguishable.

Figure 8B:
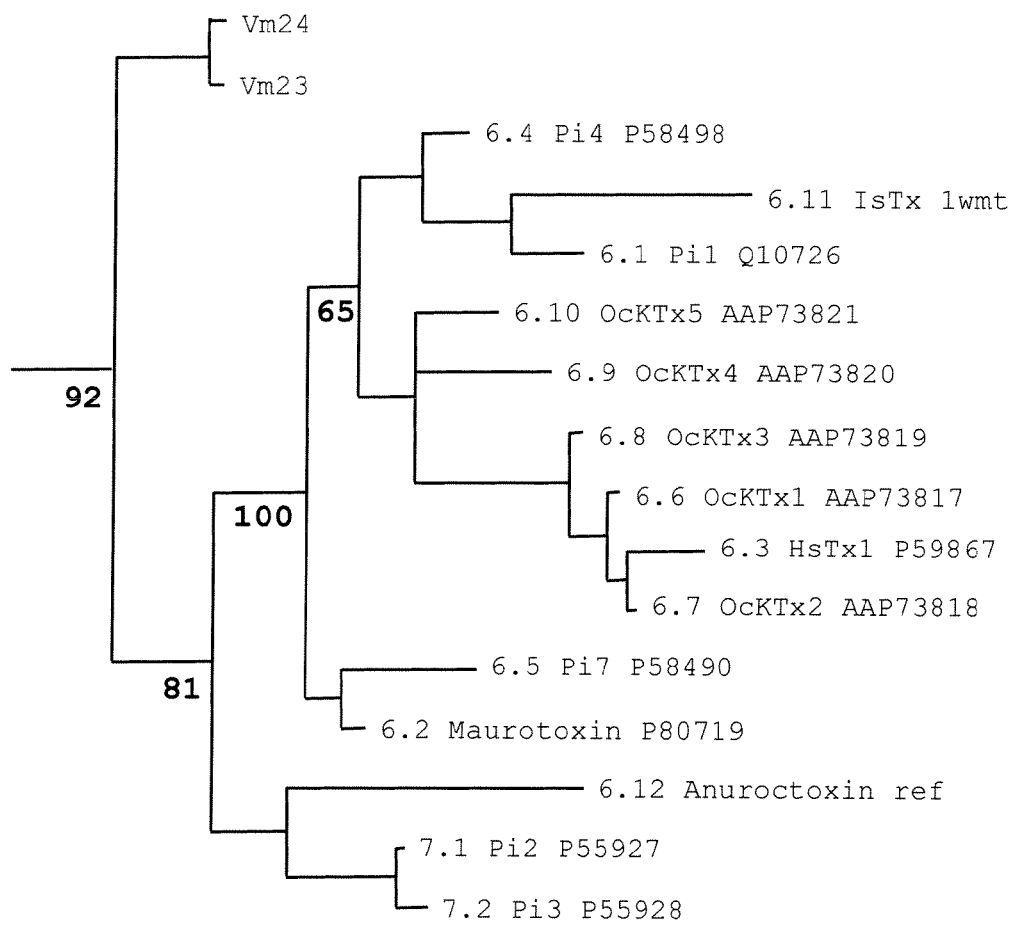

FIG. 8: Sequence and phylogenetic analyses of Vm23 and Vm24. A) Multiple sequence alignment of Vm24 and Vm23 with their most closely related α-KTxs. The alignment was performed with CLUSTAL_X [Thompson et al., 1997] software and the sequence identity with Vm24 (% I, last column) calculated with BioEdit. B) Simplified phylogenetic tree calculated with MrBayes 3.0b4 [Huelsenbeck and Ronquist, 2001; Ronquist and Huelsenbeck, 2003]. Vm23 and Vm24 are clustered together and differ substantially from the members of sub-family α-KTx 6. Vm24 is SEQ ID NO: 2. Vm23 is SEQ ID NO: 1. Pil is SEQ ID NO: 4. Maurotoxin is SEQ ID NO: 5. HsTx1 is SEQ ID NO: 6. Pi4 is SEQ ID NO: 7. Pi7 is SEQ ID NO: 8. OcKTx1 is SEQ ID NO: 9. OcKTx2 is SEQ ID NO: 10. OcKTx3 is SEQ ID NO: 11. OcKTx4 is SEQ ID NO: 12. The first portion of the OcKTx5 sequence is SEQ ID NO: 13. The second portion of the OcKTx5 sequence is SEQ ID NO: 14, and is provided separately due to amino acids being removed between the first portion and the second portion. Anuroctoxin is SEQ ID NO: 15. Spinoxin is SEQ ID NO: 16. HgeTx1 is SEQ ID NO: 17.

FIG. 9: Selective block of lymphocyte ion channels by Vm24. A) Whole-cell potassium currents through hKv1.3 channels were evoked from a human T cell in response to depolarizing pulses to +50 mV from a holding potential of −120 mV every 15 s. Currents in the absence of Vm24 (control, indicated by arrow) are almost completely blocked when 1 nM Vm24 is administered to the cell via the perfusion of the extracellular medium. Arrow indicates the $1^{st}$ pulse in Vm24. B) The normalized peak currents as a function of time are shown following the application of 1 nM (filled circles) or 0.3 nM (empty circles) of Vm24. Arrow indicates the start of the application of the toxin. C) The normalized peak currents of a lymphocyte as a function of time are shown as 3 pM Vm24 is applied to the cell and then removed (wash-out) from the extracellular medium. Perfusion with a toxin-free medium resulted in a very slow partial recovery from block with a time constant of ~3800 s. Pulses were delivered every 30 s. D) The dose-response relationship for Vm24 was obtained by plotting the remaining current fraction (RCF=I/I$_0$) as a function of toxin concentration, where I and I$_0$ are the peak currents measured in the presence and absence of the toxin, respectively, and fitting the data points with the function: RCF=$K_d^n$/($K_d^n$+[Tx]$^n$), where [Tx] indicates the toxin concentration and $K_d$ is the dissociation constant. Error bars indicate SEM (n=3-6). The dose-response function constructed this way yields a $K_d$=2.9 pM and a Hill coefficient n~1. E) Ca$^{2+}$ activated K channels of T lymphocytes (hIKCa1) were expressed in Cos-7 cells and currents were elicited by voltage ramps from −120 to +50 mV from a holding potential of −120 mV every 10 s. Current traces recorded before the application of the toxin (control), following the equilibration of block in the presence of 10 nM Vm24 for 4.5 min and following wash-out (wash) of the toxin for 2.5 min. are shown. F) Remaining fraction of the hIKCa1 current in the presence of 1 nM and 10 nM Vm24 was calculated s/s$_0$ where s and s$_0$ are the slopes of the I-V relationships evoked by voltage ramps in the presence and absence of Vm24, respectively. Error bars indicate SEM (n=3).

FIG. 10: Vm24 is selective for hKv1.3 among Shaker family (Kv1.x) channels. Current traces recorded before the application of the toxin (control), following the equilibration of block by 10 nM Vm24 and following wash-out (wash) of the toxin are shown. A) mKv1.1 channels were expressed by L929 cells and currents were evoked by voltage steps to +50 mV from a holding potential of −120 mV every 30 s. Equilibrium block developed in 6 min., the duration of the wash-out period was 5 min. B) hKv1.2 channels were expressed by Cos-7 cells and currents were evoked by voltage steps to +50 mV from a holding potential of −120 mV every 30 s. Equilibrium block developed in 5.5 min., the duration of the wash-out period was 7 min. C) hKv1.3 channels were expressed endogenously by peripheral blood lymphocytes and currents were evoked by voltage steps to +50 mV from a holding potential of −120 mV every 15 s. Equilibrium block developed in 3.5 min., the duration of the wash-out period was 4.5 min D) Fast inactivation-removed hKv1.4 (Kv1.4ΔN) channels were expressed by Cos-7 cells and currents were evoked by voltage steps to +50 mV from a holding potential of −120 mV every 30 s. The durations of Vm24 application and the wash-out period were 5 min and 4.5 min, respectively. E) hKv1.5 channels were expressed by MEL cells and currents were evoked by voltage steps to +50 mV from a holding potential of −120 mV every 15 s. The durations of Vm24 application and the wash-out period were 6 min and 3.5 min., respectively.

FIG. 11: Vm24 does not block or inhibit a variety of biologically important ion channels. Current traces recorded before the application of the toxin (control), following the equilibration of block by 10 nM Vm24 and following wash-out (wash) of the toxin are shown. A) rKv2.1 channels were expressed by Cos-7 cells and currents were evoked by voltage steps to +50 mV from a holding potential of −120 mV every 30 s. The durations of Vm24 application and the wash-out period were 7 min and 3 min., respectively. B) hERG channels were expressed by HEK cells and currents were evoked by a voltage step to +20 mV followed by a step to −40 mV during which the peak current was measured. The holding potential was −80 mV, pulses were delivered every 30 s. The durations of Vm24 application and the wash-out period were 5 min. and 2.5 min, respectively. C) hBK ($K_{Ca}$1.1) channels were expressed by tsA-201 cells and currents were evoked by a voltage step to +50 mV preceded by a 10-ms hyperpolarization to −120 mV from a holding potential of 0 mV. Pulses were delivered every 5 s. The durations of Vm24 application and the wash-out period were 4 min and 1 min, respectively. D) Na$_V$1.5 channels were expressed by Cos-7 cells and currents were evoked by voltage steps to 0 mV from a holding potential of −120 mV every 15 s. The durations of Vm24 application and the wash-out period were 1 min and again 1 min, respectively.

FIG. 12: Selectivity profile of Vm24. Bars indicate the remaining current fractions at equilibrium block of the indicated channels by Vm24 applied in 1 nM (A) or 10 nM concentration (B). Data is presented as mean±SEM, for n≧3 independent experiments. For the expression systems and the calculation of RCF and other conditions see details in legends to FIGS. 9-11.

FIG. 13: High affinity block of hKv1.3 channels by synthetic Vm24. A) Whole-cell potassium currents through hKv1.3 channels were evoked from a human T cell in response to depolarizing pulses to +50 mV from a holding potential of −120 mV every 30 s. Currents recorded in the absence of the peptide (control, indicated by arrow) are substantially blocked (>90%) when 100 pM synthetic Vm24 (sVm24) is administered to the cell via the perfusion of the extracellular medium. Arrow indicates the $1^{st}$ pulse in sVm24. B) Normalized peak currents as a function of time are shown following the application of 100 pM of sVm24. Arrow indicates the start of the application of the toxin. No significant recovery from block is achieved when the cell was perfused with sVm24-free solution (arrow indicates the start of the wash-out period). C) Bars indicate the remaining current fractions at equilibrium block of hKv1.3 by sVm24 and Vm24 applied in 100 pM concentration. Data is presented as mean±SEM, for n≧3 independent experiments. For the expression system, the calculation of RCF and other conditions see details in legends to FIGS. 9-11.

FIG. 14: Vm23 is selective for hKv1.3. Current traces recorded before the application of the toxin (control), following the equilibration of block by 10 nM Vm23 and following wash-out (wash) of the toxin are shown. Ion channels significantly blocked by Vm24 in 10 nM concentration were selected for pharmacological profiling of Vm23. A) hKv1.3 channels were expressed endogenously by peripheral blood lymphocytes and currents were evoked by voltage steps to +50 mV from a holding potential of −120 mV every 15 s. Equilibrium block developed in 3.5 min, the duration of the wash-out period was 2 min B) $Ca^{2+}$ activated K channels of T lymphocytes (hIKCa1) were expressed in Cos-7 cells and currents were elicited by voltage ramps from −120 to +50 mV from a holding potential of −120 mV every 15 s. The durations of Vm23 application and the wash-out period were 3.5 min and 2 min, respectively. C) mKv1.1 channels were expressed by L929 cells and currents were evoked by voltage steps to +50 mV from a holding potential of −120 mV every 15 s. The durations of Vm23 application and the wash-out period were 3.5 min and 1 min, respectively. D) hKv1.2 channels were expressed by Cos-7 cells and currents were evoked by voltage steps to +50 mV from a holding potential of −120 mV every 15 s. Equilibrium block developed in 3.5 min., the duration of the wash-out period was 2 min FIG. 15: Selectivity profile of Vm23. The bars indicate the remaining current fractions at equilibrium block of the indicated channels by Vm23 applied in 10 nM concentration. Data is presented as mean±SEM, for n≧3 independent experiments. For the expression systems and the calculation of RCF and other conditions see details in legends to FIGS. 9 and 14.

Figure 16:
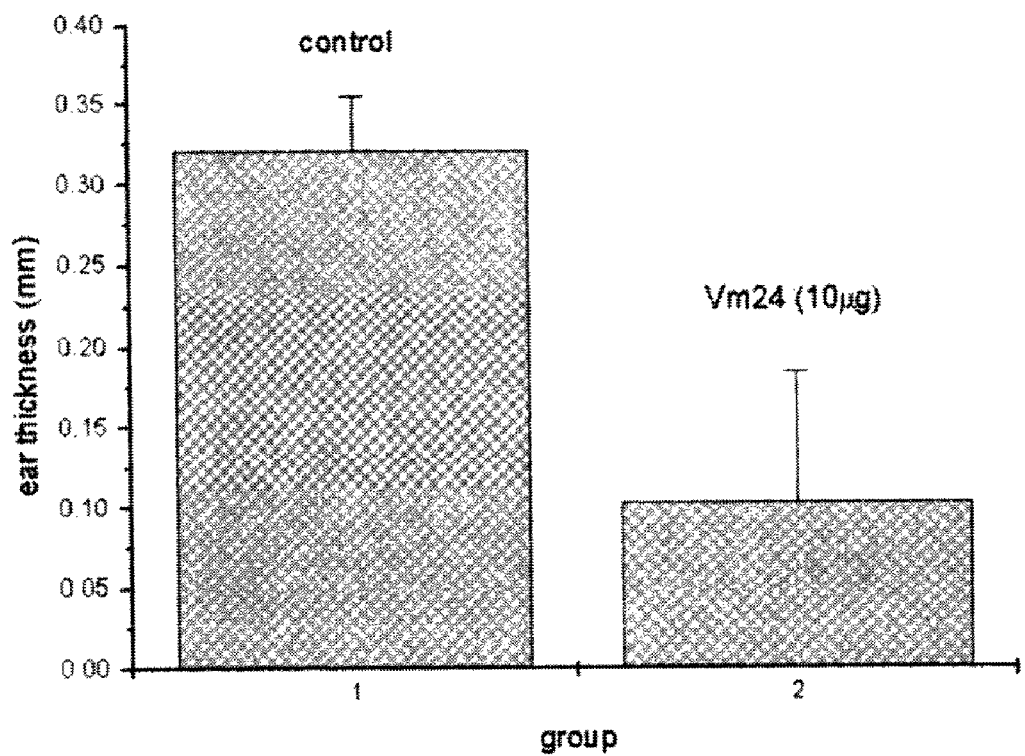

FIG. 16: Delayed-type hypersensitivity (DTH) response in rats. Two groups of 3 rats each were sensitized and challenged by application of DNFB. One group received an injection of PBS alone (control, number 1) and the other received a single injection of 10 micrograms Vm24 (group 2). The ear measurements were taken 24 hours after this treatment. The control bar shows the thickness of the ears after challenging with DNFB for the control rats, whereas the bar corresponding to the treatment group (group 2) shows the thickness of the ears of the rats that were treated with Vm24. Approximately 60% decrement on the inflammation was observed in the rats receiving Vm24, when compared to the control rats.

DETAILED DESCRIPTION OF THE INVENTION

Definitions

Unless defined otherwise, all technical and scientific terms used herein have the same meaning as commonly understood by those of ordinary skill in the art to which this invention belongs. As used herein, the following terms have the meanings ascribed to them unless specified otherwise. Although any methods and materials similar or equivalent to those described herein may be used in the practice or testing of the present invention, the preferred methods and materials are described. For purposes of the present invention, the following terms are defined below.

In the present invention the terms "peptide", "polypeptide" and "protein" are used indistinctly to refer the peptide molecules of the present invention.

The term "Kv1.3 potassium channel blocking activity" generally refers to the actual estimation of the degree of inhibition of the flow of potassium ions through the said Kv1.3 channels, caused by the presence of a Kv1.3 potassium channel inhibitor.

The term "Kv1.3 potassium channel blocker" generally means a substance that inhibits flow of potassium ions through a Kv1.3 channel of the cell membrane that contains said channel, by directly occluding the ion conduction pathway.

The term "analog" generally means any polypeptide chain that shares at least 83% pairwise sequence identity over the 36 aligned positions of SEQ ID NO:1, SEQ ID NO:2 and SEQ ID NO:3 (30 match over 36 positions). It could include, but is not restricted to, up to six amino acid changes, one or more non-natural amino acid residues, chemical derivatization of one or more of the residues, and N-terminal and/or C-terminal extensions either by other amino acid residues or other organic moieties.

The term "pairwise sequence identity percentage" generally means the coefficient between amino acid residue positions that have the same amino acid in two aligned sequences over all positions when the two protein sequences are aligned.

The term "functional equivalent" generally means any molecular structure which displays similar affinity and selectivity towards Kv1.3 as set forth SEQ ID NO:1 or SEQ ID NO:2, providing it shares the same structural determinants of affinity and/or specificity that confers the high affinity and selectivity towards Kv1.3 channels to these sequences. It could be either an analog or peptidomimetic.

The term "structural determinants of affinity and/or specificity" generally means all the functional groups and their three dimensional positions on the polypeptide structure which confers SEQ ID NO:1 and SEQ ID NO:2 with high affinity and specificity towards hKv1.3 channels. These structural determinants of affinity and specificity can be related to the same, partially overlapping or different amino acid residues.

The term "functional group" generally means a given chemical moiety within SEQ ID NO:1, SEQ ID NO:2 or SEQ ID NO:3, either in the main polypeptide chain or in the side chains of its amino acid residues, which makes specific and strong contacts with hKv1.3 channels, hence determining the affinity and selectivity of SEQ ID NO:1, SEQ ID NO:2 towards hKv1.3 channels.

The term "functional equivalent analog" generally means any polypeptide chain that shares at least 83% pairwise sequence identity over the 36 aligned positions of SEQ ID NO:1, SEQ ID NO:2 and SEQ ID NO:3 (30 matches over 36 positions). It could include, but is not restricted to, one or more non-natural amino acid residues, chemical derivatization of one or more of the residues, and N-terminal and/or C-terminal extensions either by other amino acid residues or other organic moieties, which display similar affinity and selectivity towards hKv1.3 as set forth SEQ ID NO:1 or SEQ ID NO:2.

The term "peptidomimetic" generally means any chemical compound that displays the same functional groups at similar three dimensional positions as that of SEQ ID NO:1, SEQ ID NO:2 or SEQ ID NO:3, therefore mimicking the specific contacts of SEQ ID NO:1, SEQ ID NO:2 with hKv1.3 channels.

The term "Peptides of the present invention" generally means peptides having a SEQ ID NO:3, with a tertiary structure maintained by four disulfide bridges established to be between pairs of cysteines at positions C6 and C26, C12 and C31, C16 and C33, and C21 and C36, where the letter C stands for the abbreviation of cysteine residues and the numbers correspond to their relative positions in the aligned amino acid sequence. Exemplary preferred peptides are those having a sequence SEQ ID NO:1 (Vm23) and SEQ ID NO:2 (Vm24). Said peptides are capable of blocking with high affinity and specificity the potassium channel Kv1.3. Included are functional equivalent analogs of SEQ ID NO:1, SEQ ID NO:2 or SEQ ID NO:3, i.e. that share at least 83% pairwise sequence identity over the 36 aligned positions of SEQ ID NO:1, SEQ ID NO:2 and SEQ ID NO:3 (30 matches over 36 positions), they conserve the tertiary structure maintained by the four disulfide bridges and they display similar affinity and selectivity towards hKv1.3 as set forth SEQ ID NO:1 or SEQ ID NO:2.

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in REMINGTON'S PHARMACEUTICAL SCIENCES (Mack Publishing Co., Easton, 19th ed. 1995). Preferred pharmaceutical carriers depend upon the intended mode of administration of the active agent. Typical modes of administration are described below.

The term "pharmaceutically acceptable salt" refers to non-toxic acid addition salts, including salts formed with inorganic acids, such as hydrochloric acid, hydrobromic acid, phosphoric acid, sulfuric acid and perchloric acid, and salts formed with organic acids, such as acetic acid, oxalic acid, maleic acid, malic acid, tartaric acid, citric acid, succinic acid or malonic acid. Other pharmaceutically acceptable salts include inorganic nitrate, sulfate, acetate, malate, formate, lactate, tartrate, succinate, citrate, p-toluenesulfonate, and the like, including, but not limited to, cations based on the alkali and alkaline earth metals, such as sodium, lithium, potassium, calcium, magnesium and the like, as well as non-toxic ammonium, quaternary ammonium, and amine cations, including, but not limited to, ammonium, tetramethylammonium, tetraethylammonium, methylamine, dimethylamine, trimethylamine, triethylamine, ethylamine, and the like.

The term "pharmaceutical composition" means a composition suitable for pharmaceutical use in a subject, including a mammal subject or a human subject. A pharmaceutical composition generally comprises an effective amount of an active agent and a pharmaceutically acceptable carrier.

The term "effective amount" means a dosage of a particular active agent, in this case a peptide having a Kv1.3 potassium channel blocking activity, sufficient to produce a desired result, for instance suppressing an immune response in a mammal, treating an autoimmune disease in a subject in need thereof, suppressing T-cell activation processes in the immune system of a mammal, attenuating calcium signaling pathways in a T-lymphocyte. The desired result may comprise a subjective or objective improvement in the subject (including cells) which receives the dosage.

The term "subject" is intended to mean a mammal animal, including a human. Non-human mammals subject to treatment include, for example, cows, sheep, pigs, horses, dogs and cats.

The term "autoimmune disease" generally means a pathological condition driven by immune cells of an organism that affects the homeostasis of said organism.

The term "autoimmune disease associated to lymphocytes $T_{EM}$" means any autoimmune disease where the cell that attacks the organism is a lymphocyte $T_{EM}$ cell. Among these diseases are included, but not restricted to: multiple sclerosis, rheumatoid arthritis, type I diabetes, autoimmune psoriasis, lupus erythematosus, ulcerative colitis, sympathetic ophtalmia and bone resorption periodontal disease.

A "prophylactic treatment" is a treatment administered to a subject who does not exhibit signs of a disease or exhibits only early signs of a disease, wherein treatment is administered for the purpose of decreasing the risk of developing a pathologic situation, particularly an autoimmune disease, more specifically an autoimmune disease associated to lymphocytes $T_{EM}$.

A "therapeutic treatment" is a treatment administered to a subject who exhibits signs of pathology, wherein treatment is administered for the purpose of diminishing or eliminating those pathological signs, particularly an autoimmune disease, more specifically an autoimmune disease associated to lymphocytes $T_{EM}$.

The term "organ" means body systems such as the heart, liver, lung, kidney, brain, adrenal, vascular-endothelial system, immune system, and the like.

The term "molecular probe" generally means any chemical or biological substance that can be used specifically for identification of target cells, cellular structures, receptors or any molecule to which the probe can bind with high affinity and specificity.

The term "nonessential amino acid" generally means any amino acid within the SEQ ID NO:1, SEQ ID NO:2 or SEQ ID NO:3 that could be changed for any other amino acid without substantially changing the affinity or specificity of the resulting analog towards Kv1.3 channels.

Main Findings

The main subject of this invention refers to two novel peptides (Vm23 and Vm24), their amino acid sequences (SEQ ID NO:1 and SEQ ID NO:2), as well as possible functional equivalent analogs, and their potential use as specific immunosuppressant agents. Vm23 and Vm24 are highly selective blockers of potassium ion channels of sub-type Kv1.3, particularly of human lymphocytes (hKv1.3), and were shown in vivo to decrease the inflammatory response to delayed-type hypersensitivity reactions in rats, hence these two peptides and their functional equivalent analogs are lead compounds to be used for treatment of some immunological diseases related to abnormal T-cell responses. Before entering into the details of these immunosuppressant agents and their effect on hKv1.3 channels it is important to revise some basic knowledge in this field.

Regulation of membrane potential of all cells is mainly maintained by the presence of ion-channels permeable to potassium ions, simply called K channels. Individual cells may express several distinct K channels, which can open or close in response to changes in voltage, intracellular calcium levels or specific ligands, although voltage-gated channels are the most common [Gutman et al., 2005]. Among the natural ligands that can modulate the function of K channels are toxins from venoms of bees, scorpions, snakes and sea anemone [Castle et al., 1989; Jouirou et al., 2004; Rodriguez de la Vega and Possani, 2004]. Examples of such toxins are noxiustoxin from the scorpion *Centruroides noxius* [Carbone et al., 1982], charybdotoxin from the scorpion *Leiurus quinquestriatus* [Miller et al., 1985], Anuroctoxin from the scorpion *Anuroctonus phayodactilus* [Bagdany et al., 2005], BgK from the anemona *Bundosoma granulifera* [Aneiros et al., 1993] and ShK from *Stichodactyla helianthus* [Castaneda et al., 1995]. These toxins have been shown to block a variety of different types and sub-types of $K^+$ channels, including Kv1.3, with different affinities and specificities [reviewed by Panyi et al. 2006]. Kv1.3 channel has been implicated in T lymphocyte proliferation and lymphokine production, and blockers of Kv1.3 are of interest as potential immunosuppressants [Panyi et al. 2006].

Several of these K channel specific toxins have had their three-dimensional structure determined (reviewed in [Mouhat et al., 2004]. Thanks to the solution of the three-dimensional structure of a couple of voltage-dependent K channels that contain six-transmembrane segments [Lee et al., 2005: Long et al., 2005] and the experiments conducted with double mutants (toxins and channels) by several groups [Goldstein et al., 1994; Stampe et al., 1994; Aiyar et al., 1995; Hidalgo and Mackinnon, 1995] the contact surface of several of these ligands with K channels were identified. Concerning the scorpion toxins known to date, more than 125 different peptides were studied, whose amino acid sequences were reported [Rodriguez de la Vega and Possani, 2004]. These peptides were grouped into 20 different sub-families, based mainly on three criteria: primary sequence similarity, position of the disulfide bridges and specificity of function. For the purpose of the present invention both peptides (Vm23 and Vm24) were isolated, purified, sequenced and assayed. The important originality and proprietary information obtained is the uniqueness of their primary structure and the highly specific function, which is not evident by simple observation of their structural characteristics, but needs experimental evidence of function, both in vitro and in vivo, as shown and claimed in this invention.

This work started by the collection of scorpions of the species *V. mexicanus* in the field and the extraction of their venom by electrical stimulation. The scorpions were collected in the State of Morelos, Mexico. The authors have the official authorization for this purpose (document number SGPA/DGVS/02483 of Mar. 18, 2005, given by the *Secretaria de Medio Ambiente y Recursos Naturales* of Mexican Government). Usually 30 scorpions were milked after anesthesia with carbon dioxide ($CO_2$). The crude venom was either processed immediately or kept frozen at −20° C. until used.

The soluble venom was subsequently separated by HPLC. The purified peptide, object of this invention, were further assayed in vivo using mice as model animals for possible toxic effects (lethality tests), and have had their primary structure determined by Edman degradation and mass spectrometry analysis. The details of these experiments are described in example 1, below.

Due to the fact that the amount of these peptides is relatively small in the venom, in order to further characterize their functionality and specificity of action on hKv1.3 channels, a substantial amount of Vm24 was chemically synthesized.

Chemical Synthesis of Vm24

Synthesis of a peptide via solid-phase methods includes the use of a solid-phase resin such as but not limited to polystyrene, polyacrylamide, certain fibers or other stable polymers. Derivatization of the solid-phase resin can be produced with a suitable handle such as chlorotrityl chloride, 2-chlorotrityl chloride, hydroxymethylphenil, Sasrin as a mean to produce the C-terminal acid functionally or may be prepared by means of proteolytic stabilization via a resin linker such as but not limited to a 4-(2',4'-dimethoxyphenyl-Fmoc-aminomethyl)-phenoxymethyl group.

Chain assembly usually includes any of the protecting group strategies where the amino acid protecting group is either t-butyloxycarbonyl (Boc) or 9-fluorenyl-methyloxycarbonyl (fmoc). The reactive side chains of the various amino acids used for synthesis of the peptide are normally protected. Commonly used protecting groups include: t-butyl, benzyl, trityl, methyltrityl, benzyl-methylbenzyl, tosyl, benzyloxymethyl, t-butyloxycarbonyl, 2-chlorobenzyl, 2-bromobenzyl, methoxybenzyl, formyl, acetomidomethyl, pentamethylchroman sulfonyl, pentamethyldihydrobenzofuran-sulfonyl, nitro for side chain amines, guanidines, phenols, alcohols, acids, imidazoles, thiols, and indoles. Other protecting groups could be invented that accomplish the same goal of eliminating undesirable side reactions during primary chain assembly.

Synthesis of the amide bond during addition of novel amino acids to the growing peptide may be accomplished by using any of the acid activation methods including but not limited to symmetrical anhydrides (carbodiimide), HOBT esters, acyl fluorides, uronium activators such as but not limited to TBTU, HATU or HBTU, phosphonium activators such as but not limited to BP, PyBOP, PyBrOP. These are all methods of activation of the carboxyl group which those practicing the art of peptide synthesis would be expected to know.

Synthesis of analog structures which include substitution of unnatural amino acids into the sequences SEQ ID NO:1 (Vm23), SEQ ID NO:2 (Vm24) or SEQ ID NO:3 (Vm23 and Vm24 consensus sequence) may also be useful for certain embodiments of the invention. The use of convergent methods whereby fragments of the peptide are assembled in a fashion whereby the ultimate product is Vm23, Vm24 or their analogs is also known and can be used by experts in the field. The methods for the cleavage of the synthetic peptide out of the solid support at the end of the synthetic procedure and the correct folding of the disulfide bridges to obtain the sequences SEQ NO.1 and 2 or their analogs are also known and can be reproduced by experts on the state of the art of the subject. Final cleavage and deprotection and folding of the toxin may be but not limited to either HF or TFA depending on the strategy employed for synthesis. Disulfide bond formation includes any orthogonal approach where differential Cys protection could be used to position the disulfide bonds in the correct form: C6-C26, C12-C31, C16-C33, and C21-C36 linkage for Vm24. However the disulfide bridge formation can also be obtained by air oxidation, or shuffling reactions assisted by the presence of reduced and oxidized glutathione in various proportions.

Following this basic methodology various naturally-occurring toxins from snake, scorpion and sea anemone were produced synthetically, radiolabeled with $I^{125}$ and used as molecular probes for investigating potassium channel structure and function [Strong, 1990; Moczydlowski et al., 1998; Garcia et al, 2001, Kem et al., U.S. Pat. No. 6,077,680]. Many of these toxins are selective for particular K channel subtypes [Auguste et al., 1990; Galvez et al., 1990; Crest et al., 1992; Garcia-Calvo et al., 1993; Garcia et al, 1994, Kem et al., U.S. Pat. No. 6,077,680]. Among the most often used examples are dendrotoxin from the venom of the snake *Dendroaspis polylepsis* [Harvey, 1997], BgK from the sea anemone *Bunodosoma granulifera* [Aneiros et al., 1993; Alessandri Haber et al., 1999] and ShK from the anemone *Stichodactyla helianthus* [Castaneda et al., 1995; Pennington et al., 1995] and several scorpion toxins such as noxiustoxin from *Centruroides noxius* [Drakopoulou et al., 1995] and charybdotoxin from *Leiurus quinquestratus* [Sugg et al., 1990], to mention just a few. Some of these toxins, such as ShK blocks Kv1.3 type K channels in Jurkat T lymphocytes at very low concentrations (<1 nM). However, many of them suffer from the lack of specificity. That is, at concentrations in the order of 10 to 100 nM they are also able to block other sub-types of channels. Since, as it will be demonstrated in the examples to be described below, Vm23 and Vm24 are exquisitely specific for hKv1.3 channels and have a distinct primary structure from the other peptides described so far in the literature, we decided to prepare Vm24 synthetically.

The covalent structure of Vm24 was obtained by chemical synthesis according to the solid phase system of Merrifield [Merrifield, 1964], using fmoc-amino acids, as earlier described by our group [Drakopoulou et al., 1995].

The possibility of substitution of some of the amino acids of the primary structure of SEQ ID NO:1, SEQ ID NO:2 or SEQ ID NO:3, by other modified amino acids in order to obtain an analog peptide with a higher half life in vivo, thus reducing protease susceptibility of the native peptides is within the scope of the present invention. This may include replacement or substitution of nonessential residues with conservative isosteric replacements; for example: lysine for glutamine or acetyl-lysine, or a neutral amino acid such as alanine, or Na-methylated amino acid substitution in certain positions to reduce proteolytic degradation of the biologically active peptides. Also truncation of the primary sequence, by deletion of certain amino acids nonessential for the function, or addition of extra residues can provide the analog structure with a higher stability in vivo. Some nonessential residues of the peptides of the present invention identified by the alignment of SEQ ID NO:1 and SEQ ID NO:2 include but are not restricted to: those residues in positions No. 10, 13, 17, 23, 29 and 35 of aligned SEQ ID NO:1 and SEQ ID NO:2 or aligned SEQ ID NO:1, SEQ ID NO:2 and SEQ ID NO:3.

A functional equivalent analog peptide can be produced by inclusion of selected D-amino acids or by chemical synthesis of a retro-inverse analog, where all residues are D-amino acids and the amino acid sequence is reversed [Jameson et al., 1994; Juvvadi et al., 1996]. These modifications could increase the stability of the product.

Another major approach is the development of low molecular weight compounds based on the structural determinants of affinity and specificity of SEQ ID NO:1, SEQ ID NO:2 or SEQ ID NO:3 in order to generate non-peptidic (peptidomimetic). In these studies, non-peptidic scaffolds are designed and synthesized, which contain key functional groups from the potassium channel binding surface of the parent polypeptide. There are many examples where naturally occurring low molecular weight, non-peptidic compounds, have been shown to mimic or to antagonize the effect of a polypeptide or protein ligand. Peptidomimetic compounds have been designed and synthesized for a number of therapeutically relevant peptides. A loop present on the CD4 receptor which binds to HIV gp120 protein was designed and synthetically obtained [Chen et al., 1992] and shown to be an effective blocker of gp120 binding to the CD4 receptor at low micromolar concentrations. FTI-276 is another example of a mimetic of the C-terminal region of Ras protein which is a potent blocker of oncogenic Ras signaling [Lerner et al., 1995].

As it can be deduced from the above described, there are many ways of preparing functional equivalent analogs of these two peptides Vm23 and Vm24 that can be used as leading drugs to control abnormal functions of T lymphocytes. Improper activation of T lymphocytes are known to cause autoimmune diseases (such as multiple sclerosis, rheumatoid arthritis, type I diabetes, autoimmune psoriasis, lupus erythematosus, ulcerative colitis, sympathetic ophtalmia and bone resorption periodontal disease.), and transplant rejection among others.

In order to test the efficiency of possible new immunosuppressant drugs there are many animal models, which provide adequate in vivo assays for testing the efficiency and possible side-effects of a novel unknown compound, as it is the case of the reaction known as delayed type hypersensitivity (DTH-response) in rats, which has been used in the present invention. As it will be shown and discussed below, to assess the protective effect of the peptides of the present invention, small doses of Vm24 was tested to control the inflammatory reaction that occurs in the ear of rats previously sensitized with dinitrofluorobenzene (DNFB). This assay has been widely used and is accepted as adequate model for the purposes of the present invention [Phanuphak et al., 1974].

Immunosuppressant

Immunosuppressants such as cyclosporin and FK506 exhibit severe side effects which limit their therapeutic use. Research conducted with these two compounds was able to identify at least some of the molecular mechanisms being responsible for undesirable side-effects upon the administration of these drugs. Cyclosporin interacts with the protein cyclophilin which is present in many different tissues, whereas FK506 causes toxicity because it targets the FK-binding protein, also found in many different tissues. There has therefore been a major effort to identify novel immunosuppressants without serious side-effects. One of the main goals is to identify novel targets expressed principally in T-lymphocytes, such as the Kv1.3 ion-channel. The Kv1.3 potassium channels expressed in T-lymphocytes are very important for certain cellular functions, although RNA coding for this protein is also found in other cells (B-lymphocytes, microglia, macrophages, osteoclasts, platelets and some brain cells). However, only in T-lymphocytes, Kv1.3 dominates the membrane potential and has its blockade significant functional consequences. Due to the distinct mechanism of action of Kv1.3 blockers and the relatively restricted tissue distribution of Kv1.3 channels, a specific and high affinity blocker of Kv1.3 is expected to display less toxic side-effects than cyclosporin and FK-506, hence, it may prove useful for treatment of autoimmune diseases as well as for transplantation therapy.

Scientists from Merck Sharpe and Dohme have shown that margatoxin (another scorpion toxin peptide) has a potent effect as blocker of the Kv1.3 channel and it is capable of suppressing the immune response in an animal model (pig). However, margatoxin is not specific for Kv1.3 channels, but also affects the Kv1.2 channel with similar potency. Since the heart and brain tissues also express Kv1.2 channels, its blockage might have serious deleterious effects. Another peptide isolated from sea-anemone, ShK is a potent blocker of Kv1.3 (see Kem et al., 2000, U.S. Pat. No. 6,077,680), that also affects other related Kv1 channels but more than one hundred fold higher concentration is needed for a similar blockade. It means that the related channels are >100-fold less sensitive to its application, when compared to Kv1.3. Peptides Vm23 and Vm24, object of this invention, are from a different biological source, have a distinctly different primary structure from that of ShK and are more specific for hKv1.3 channels than ShK. Vm23 and Vm24 blocks ≦50% of a couple of other K channels when applied at a concentration more than 3000 times higher than what is needed to block the same fraction of hKv1.3 channels, as it will be shown and discussed in detail in the examples below (examples 7 to 10).

This invention also comprises the production of Vm23, Vm24 and their functional equivalent analogs by the solid-phase method. The procedures used for chemical synthesis include a series of well known protocols to experts in the field, as detailed within the description of example 3.

Electrophysiological Characterization

The development of an efficient immune response against foreign or autoantigens requires the activation and proliferation of lymphocytes specific for a given antigen. This requires a well-coordinated interplay between different cellular components of the immune system. The first step in this process is the presentation of the processed antigens to lymphocytes by professional antigen presenting cells [Janeway et al., 2001]. Within the subject of the present invention is the regulation of T-lymphocyte mediated immune responses (e.g. delayed-type hypersensitivity) by blockers specific for the voltage-gated K channel, Kv1.3. Thus we restrict the elaboration of the involvement of K channels in lymphocyte activation to T cells. However, we should mention that proliferation of certain subsets of B lymphocytes also depend on the activity of Kv1.3 channels [Wulff et al., 2004].

Recognition of the presented antigen by the antigen receptor of T cells leads to the activation, proliferation and terminal differentiation of the cells [Sallusto et al., 2004]. Transmembrane signaling pathways triggered by antigen recognition include the activation of several protein kinases and consequently that of phospholypase C-γ (PLC-γ). Generation of inositol 1,4,5-trisphosphate (IP3) by PLC-γ-mediated hydrolysis of the membrane phospholipid phosphatidylinositol 4,5-biphosphate (PiP2) initiates the biphasic $Ca^{2+}$ signal required for commitment to proliferation in T cells [Lewis, 2001]. IP3 diffuses and binds to its receptors in the endoplasmic reticulum (ER), which results in the release of $Ca^{2+}$ into the cytosol and a significant rise in the cytosolic free calcium concentration ($[Ca^{2+}]i$). The transient rise in $[Ca^{2+}]i$ following the release from the ER is not sufficient for the execution of the signal transduction cascade, a sustained $Ca^{2+}$ signal is necessary. This is realized by $Ca^{2+}$ influx from extracellular space through $Ca^{2+}$ channels in the plasma membrane through calcium-release activated $Ca^{2+}$ channels (CRAC channels) [Zweifach and Lewis, 1993].

Although CRAC channels are inherently voltage-independent, the $Ca^{2+}$ current is sensitive to the electrochemical gradient for $Ca^{2+}$, which is influenced by the membrane potential of the cells [Panyi et al., 2004]. The depolarizing $Ca^{2+}$ influx has to be counter-balanced by the activation of K channels to clamp the membrane potential at negative values and thus, to provide a sufficient driving force for further $Ca^{2+}$ entry [Fanger et al., 2001]. Selective, regulated $K^+$ efflux is one of the major determinants of the membrane potential of human T lymphocytes, which is around −50 to −60 mV. Two types of K channels conduct outward $K^+$ fluxes under physiological conditions in these cells. The dominant voltage-gated K channel in human T lymphocytes, Kv1.3, opens upon membrane depolarization with an activation threshold close to the resting potential of the cells [Matteson and Deutsch, 1984]. The $Ca^{2+}$-activated potassium channel of human T cells, IKCa1 (or $K_{Ca}3.1$), is activated solely by the rise of the cytosolic free calcium concentration over ~200 nM, independently of the membrane potential [Grissmer et al., 1993].

The contribution of Kv1.3 and IKCa1 channels to the membrane potential control of T cells depends on the activation status of the cells (resting vs. activated) and their functional role in the immune system determined by the degree of terminal differentiation of the T cells [Wulff et al., 2003], as described in details in the section of Background of the Invention. From the point of therapeutic applicability of Kv1.3 blockers in autoimmune diseases it is important to emphasize that selectivity for Kv1.3 channels over IKCa1 channels is of utmost importance [Wulff et al., 2003]. Effector memory T cells ($T_{EM}$), which mediate tissue damage in e.g. multiple sclerosis, rheumatoid arthritis, type I diabetes, autoimmune psoriasis, lupus erythematosus, ulcerative colitis, sympathetic ophtalmia and bone resorption periodontal disease, selectively upregulate Kv1.3 channels upon activation, and thus, the membrane potential control of these cells is governed solely by Kv1.3 channels [Beeton et al., 2006]. Consequently, the proliferation of these cells can be suppressed effectively and persistently by selective Kv1.3 inhibitors [Wulff et al., 2003; Vennekamp et al., 2004; Beeton et al., 2005]. On the contrary naïve and central memory T cells ($T_{CM}$) escape from Kv1.3 block-mediated inhibition of proliferation [Wulff et al., 2003] by transcriptional up-regulation of IKCa1 [Ghanshani et al., 2000]. The proliferation of these pre-activated cells becomes sensitive to IKCa1 inhibitors, but not to Kv1.3 inhibitors. Thus, a Kv1.3-based therapy that suppresses the activation of $T_{EM}$ cells without significant impairment of the proliferation of naïve and $T_{CM}$ cells might have use in the management of autoimmune diseases, particularly autoimmune diseases associated to lymphocyte $T_{EM}$, such as type I diabetes mellitus [Viglietta et al., 2002; Beeton et al., 2006], rheumatoid arthritis [Beeton et al., 2006], multiple sclerosis, inflammatory bone resorption in experimental periodontal disease [Valverde et al., 2004] and conditions associated to organ rejection, such as chronic graft rejection and graft-versus-host disease which are proposed to be sustained by chronically activated $T_{EM}$ cells [Yamashita et al., 2004].

Assessing Selectivity

Several high affinity peptide blockers of Kv1.3 are selective for Kv1.3 over IKCa1, similarly to Vm24. These include scorpion toxins, e.g. Mrgatoxin (MgTx), Noxiustoxin (Ntx), Kaliotoxin, Anuroctoxin and ShK toxin isolated from sea anemone. However, ion channels important in neuronal and muscle excitability are also inhibited by these toxins with nanomolar-picomolar affinities, e.g. Kv1.1 by ShK [Kalman et al., 1998] and Kaliotoxin [Grissmer et al., 1994], whereas Kv1.2 is blocked by MgTx [Koch et al., 1997], Ntx [Grissmer et al., 1994] and Anuroctoxin [Bagdany et al, 2005].

The lack of specificity of the toxins imposes the possibility of significant biological effects. Ion channels of the Kv family are widely distributed in classically excitable and non-excitable cells (see [Gutman et al., 2005] for a comprehensive review). In neurons, skeletal and cardiac muscle cells these channels are critical determinants of electrical excitability. They contribute to the maintenance of the resting membrane potential, the shaping of the action potentials by influencing the rate of repolarization, and determine the spike frequency and neuronal after hyperpolarization (see [Gutman et al., 2005] for a comprehensive review). Ion channels expressed in the central nervous system are more protected against systematically applied toxins due to the blood-brain barrier, however, in multiple sclerosis, which is a potential application area of Kv1.3 inhibitors, this barrier is compromised which leads to neural toxicity in animal models of MS [Beeton et al., 2005]. Due to the direct contact of the cells with the blood stream cardiac myocytes are more susceptible to the potential side-effect of a non-selective Kv1.3 inhibitor. In human atrial myocytes Kv1.5 [Feng et al., 1997] and in ventricular myocytes Kv1.4 [Patel and Campbell, 2005] and hERG (reviewed in [Sanguinetti and Tristani-Firouzi, 2006]) channels determine critically the repolarization phase of the action potential, whereas $Na_V1.5$ is responsible for the depolarization phase [Rogart et al., 1989]. BK $Ca^{2+}$-activated K channels are ubiquitous in the human body (brain, skeletal muscle, smooth muscle, pancreatic islet cells, etc, reviewed in [Wei et al., 2005]) and regulate a variety of physiological functions including electrical excitability of neurons and skeletal muscle cells and Ca transients in smooth muscle. The BK channels are blocked by toxins in the $\alpha$-KTx1.x family (e.g. charybdoxin [Miller et al., 1985]).

The availability of the X-ray crystallographic structure of a bacterial [Doyle et al., 1998] and a human voltage-gated K channel [Long et al., 2005] significantly expanded our understanding of the molecular basis of $\alpha$-KTx specificity for different ion channels over the last decade [Giangiacomo et al., 2004], however, to date, prediction for the selectivity profile of a given peptide toxin based on its primary structure is not possible. This substantiates the experimental determination of the selectivity of Vm 24 against ion channels having biological significance and known susceptibility to block by animal toxins.

The advancement of molecular biology and the cloning of ion channel genes allow the pharmacological studies to be conducted on recombinant ion channels. The expression of recombinant channels in suitable cell lines provides several advantages for pharmacological experiments, e.g. the magnitude of contaminating currents is negligible and the amplitude of the currents is suitable for pharmacological assays. Furthermore, the expressed recombinant channels maintain the pharmacological characteristics of the channels expressed in native cells.

Pharmaceutical Compositions

The invention provides pharmaceutical compositions comprising the peptides of the present invention. As already mentioned, these peptides are useful for suppressing an immune response in a mammal where a specific subset of T-cells is activated. In particular, pharmaceutical compositions comprising the peptides of the present invention are useful for treating or preventing a condition wherein the immune response is the result of heterologous organ rejection (by instance a heart, a lung, a liver, a kidney or a pancreas) or the result of an autoimmune disease associated to lymphocytes $T_{EM}$.

In a preferred aspect of the invention, the pharmaceutical compositions comprise the peptides of the present invention or a pharmaceutically acceptable salt thereof, and a pharmaceutically acceptable carrier. The preferred form of these pharmaceutical compositions and the selection of the pharmaceutically acceptable carrier depend on the intended mode of administration and therapeutic application. The pharmaceutical compositions include (depending on the formulation desired) pharmaceutically acceptable, non-toxic carriers or diluents, which are defined as vehicles commonly used to formulate pharmaceutical compositions for animal or human administration. Additionally and optionally, the pharmaceutical compositions may also comprise at least one additional immunosuppressive agent, which may have a complementary effect in the treatment. Some illustrative immunosuppressive agents are cyclosporine, rapamycin, azathioprine, prednisone, ShK toxin, ShK derivatives and deoxyspergualin, their derivatives, or a salt thereof. The pharmaceutical compositions of the present invention can be administered as mentioned below.

Therapeutic and Prophylactic Methods

This invention provides methods for therapeutical or prophylactic treatment of conditions where the suppression of an immune response in a mammal is required, especially when T-cells are activated in subjects in need of such treatment, wherein said conditions include heterologous organ rejection (for instance a heart, a lung, a liver, a kidney or a pancreas) or autoimmune diseases (for instance multiple sclerosis, rheumatoid arthritis, type I diabetes, autoimmune psoriasis, lupus erythematosus, ulcerative colitis, sympathetic ophtalmia and bone resorption periodontal disease.). These subjects may include humans and other mammals, such as dogs, cats, goats, cows, horses, pigs, sheeps, to mention a few of them. In one aspect, the present invention provides methods for the prophylactic or therapeutic treatment of conditions that are treatable by, responsive to, or sensitive to the inhibition of Kv1.3 potassium channels in cell membranes of T-cells of subjects in need of such treatment. These methods comprise administering to a subject in need thereof, including a human, an effective amount of a peptide of the present invention as described above. Generally, this peptide may comprise peptides Vm24 with a SEQ ID NO: 1, Vm23 with a SEQ ID NO: 1 or a peptide having a sequence SEQ ID NO: 3, or functional equivalent analogs thereof or a pharmaceutically acceptable salt thereof.

In a preferred embodiment, the present invention provides methods specifically directed to treating and preventing autoimmune diseases associated with T-cell activation or responsive to the Kv1.3 potassium channels inhibition. Such autoimmune diseases include but are not limited to multiple sclerosis, rheumatoid arthritis, type I diabetes, autoimmune psoriasis, lupus erythematosus, ulcerative colitis, sympathetic ophtalmia and bone resorption periodontal disease. These methods comprise administering to a subject in need thereof, including a human subject, an effective amount of a peptide of the present invention as described above.

In another preferred embodiment, the present invention provides methods specifically directed to treating and preventing the rejection of a heterologous organ (by instance a heart, a lung, a liver, a kidney or a pancreas). These methods comprise administering to a subject in need thereof (i.e. a subject who will receive or has receipt an organ transplantation), including a human, an effective amount of a peptide of the present invention as described above.

Dosages and Methods of Administration

In therapeutic applications, a peptide of the invention may be administered to a subject already suffering from a disease or an undesirable condition (e.g., autoimmune disease or heterologous organ rejection, respectively), in an amount sufficient to treat, cure, partially arrest, or detectably slow the progression of the disease and its complications. An amount of a peptide of the invention effective for use in therapeutic applications will depend upon the severity of the condition, the general state of the subject, and the route of administration. The effective amount of the peptide in therapeutic applications will generally be within a range from about 0.1 microgram per kilogram to about 10 microgram per kilogram of the peptide (or a pharmaceutically acceptable salt thereof) per dose.

In prophylactic applications, the subject peptides or pharmaceutical compositions thereof are administered to subjects at risk of, but not already suffering a disease or an undesired condition. The effective amount of peptide to be administered will depend upon the subject's state of health and general status of the immune system. The effective amount of the peptide in prophylactic applications will generally be within a range from about 0.1 microgram per kilogram to about 10 microgram per kilogram of the peptide per dose.

The route of delivery of the peptides and pharmaceutical compositions of the present invention is determined by the disease or clinical indication and the site where treatment is required. For a certain type of disease, limited to a restricted area of the body, it may be desirable to apply the peptide or composition thereof at the local site (topical application). Alternatively, with the progression of the disease or simultaneously to the topical application it might be desirable to administer the peptide or composition systemically.

For other indications, peptides and pharmaceutical compositions of the invention may be delivered by intravenous, intraperitoneal, intramuscular, subcutaneous, intranasal, and intradermal injection, as well as by intrabronchial instillation (e.g., by using a nebuliser), and transmucosal, systemic, transdermal (e.g., with a lipid-soluble carrier in a skin patch), oral, and gastrointestinal delivery (e.g., with a capsule or tablet).

One or more peptides of the invention may be administered in combination therapy. For example, one or more subject peptides may be administered in combination with another immunosuppressant agent (such as those above mentioned) to a subject in need of such treatment. There are some idiopathic autoimmune diseases, such as immune thrombocytopaenic purpura [Cooper and Bussel, 2006] or autoimmune lymphoproliferative syndrome [Oren et al., 2002], where the treatment could require a multitarget approach, therefore more than one immunosuppressant substance is needed.

The peptides of the invention may be administered alone or in combination with a pharmaceutically acceptable carrier as described above in the "Pharmaceutical compositions" section. The peptides may be administered in single or multiple doses. Suitable pharmaceutical carriers include inert solid diluents or fillers, sterile aqueous solutions, and various nontoxic organic solvents. The pharmaceutical compositions formed by combining a subject peptide with a pharmaceutically acceptable carrier may be readily administered in a variety of dosage forms such as tablets, lozenges, syrups, injectable solutions, and the like. If desired, the pharmaceutical carriers may contain additional ingredients, such as flavorings, binders, excipients, and the like.

For oral administration, tablets containing various excipients, such as sodium citrate, calcium carbonate, and calcium phosphate, may be employed along with various disintegrants, such as starch, and preferably potato or tapioca starch, alginic acid, and certain complex silicates, together with binding agents, such as polyvinylpyrrolidone, sucrose, gelatin, and acacia. Lubricating agents, such as magnesium stearate, sodium lauryl sulfate, and talc are also added for tableting purposes. Solid compositions of a similar type may also be employed as fillers in salt and hard-filled gelatin capsules. Preferred materials for this purpose include lactose or milk sugar and high molecular weight polyethylene glycols. When aqueous suspensions of elixirs are desired for oral administration, the essential active peptide ingredient therein may be combined with various sweetening or flavoring agents, colored matter or dyes, and, if desired, emulsifying or suspending agents, together with diluents such as water, ethanol, propylene glycol, glycerin, and combinations thereof.

For parenteral administration, solutions of the peptides of the present invention in sesame or peanut oil or in aqueous polypropylene glycol may be employed, as well as sterile aqueous saline solutions of the corresponding water soluble pharmaceutically acceptable metal salts previously described. Such an aqueous solution should be suitably buffered if necessary, and the liquid diluent first rendered isotonic with sufficient saline or glucose. These particular aqueous solutions are especially suitable for intravenous, intramuscular, subcutaneous, and intraperitoneal injection. The sterile aqueous media employed are all readily obtainable by standard techniques well known to those skilled in the art. Additionally, the aforesaid compounds may be administered topically (for example, through a placed catheter) by using an appropriate solution suitable for the particular purpose.

Vm23, Vm24 and Functional Equivalent Analogs as Molecular Probes

Beside the therapeutic use of the peptides of the present invention, these peptides could be used to detect and characterize the level of Kv1.3 channels expression in a broad variety of cells, either obtained from animal tissues or stable cultures. The importance of characterizing Kv1.3 expression in T cells has already been highlighted in this document, therefore this invention also relates to the use of the peptides of the present invention as molecular probes to physiologically characterize Kv1.3 channel-expressing cells. The detection and characterization of Kv1.3 expression can be done by several detection techniques using conveniently labeled peptides of the present invention, including but not restricted to: flow cytometry, confocal and conventional fluorescence microscopy, total fluorescence emission, radioactive binding and displacement techniques and immunological pull-down assays. Quantitative determination of Kv1.3 channels expressed in a given cell can be performed by quantitative detection techniques, including but not restricted to: channel counting by confocal laser scanning microscopy, immunogold detection and radioactive binding and displacement techniques. Moreover, chemical modifications of the polypeptide chain or side-chains of several nonessential amino acids could provide labeled functional equivalent analogs that could be used for Kv1.3 channel detection and quantification. In turn, these functional equivalent analogs could be used as molecular probes to search for specific ligands, providing these new ligands share the same binding site on Kv1.3 as Vm23, Vm24 and their functional equivalent analogs. Any such chemical modification should leave unmodified the structural determinants of Vm23, Vm24 and their functional equivalent analogs which confer them with high affinity and specificity towards Kv1.3. Chemical modification of polypeptide chains is a common procedure for obtaining useful molecular probes; it can be achieved by several widely available methods and is regularly used by experts in this field. The label provided by the modification could include, but is not restricted to, radioactive isotope, fluorescent, chemiluminescent or chromogenic moieties and crosslinking or fusion with tag proteins (antibodies, biotin, green fluorescent protein or its derivatives).

In the following examples it is described in detail how these new peptides of the present invention, were isolated, purified and chemically characterized. The synthesis of an exemplary peptide, Vm24, is described, and the selective action of two exemplary peptides of the present invention (Vm23 and Vm24) on Kv1.3 channels of human T-lymphocytes is thoroughly described. Finally, the protective action of Vm24, at low concentration in the in vivo assay for DTH-response in rats is also described.

EXAMPLES

The following examples are included to demonstrate typical preferred embodiments of the invention. Many changes can be made in the specific embodiments of the reported examples and still obtain a like or similar result without departing from the spirit and scope of this invention, by those skilled in the art. If the final products comprise the sequences shown here (SEQ ID NO:1, SEQ ID NO:2, SEQ ID NO:3) or their functional equivalent analogs, they are bound to reproduce the same results as those described here and thus are expected to function well in the practice of the invention claimed here Example 1

Isolation, Lethality Test in Mice and Primary Structure Determination of Vm23 and Vm24

All solvents and chemicals used were analytical grade and double-distilled water was used throughout the procedure as earlier described [Batista et al., 2007].
Isolation Procedures The procedures used for isolation of the various natural ligands mentioned above make use of chromatographic techniques. The venom was solubilized in water and centrifuged at 10,000×g for 5 min. The supernatant was recovered and separated by high performance liquid chromatography (HPLC). One hundred microliter containing 1.0 milligram of the soluble venom protein was applied to an analytical C18 reverse-phase column (dimensions 10×250 mm, catalog number 238TP) obtained from Vydac (Hisperia, Calif., USA), of a HPLC system (Millenium Millipore, Milford, Mass.). Components were purified using a linear gradient from solution A (0.12% trifluoroacetic acid—TFA in water) to 60% solution B (0.10% TFA in acetonitrile), run for 60 min. The detection was monitored by absorbance at 230 nm and eluted at 1 ml/min flow-rate. Fractions were collected manually and dried using a Savant Speed-Vac drier. As shown in FIG. 1 more than 80 distinct fractions were collected from this HPLC separation. Fractions that elute from 20 to 35 min retention times usually correspond to the elution time of most K channel scorpion specific toxins of other scorpion venoms studied [Batista et al., 2007]. For this reason special attention was dedicated to the venom components eluting at those times. Specifically, two fractions: one eluting at 23 and another at 24 minutes were further analyzed, because mass spectrometry determination of peptides from this elution times were closely related to the values found for other known K channel specific toxins, v.g., they had molecular masses around 4,000 Daltons. Since these components were still not homogeneous, a second chromatographic separation was conducted using the same HPLC system but eluted with a distinct gradient (solvent A to 40% solvent B for 60 min, using a C18 column, catalog number 218TP54 from Vydac, Hisperia Calif.). As shown in the inserts of FIG. 1, a major component was isolated from each one of these initial fractions (labeled with asterisk). The insert of the left side corresponds to the fraction eluting at 23 min and that on the right to the fraction eluting at 24 min. Under analysis by mass spectrometry determination and sequencing by automatic Edman degradation both peptides were found to be homogeneous. The one eluting at 24 min in our experimental conditions was analyzed first. It was pure and showed a molecular mass of 3864 atomic mass units (a.m.u.). In this document we will use interchangeably a.m.u. or Daltons (abbreviated Da) for designating one unit of molecular mass. For this reason the peptide was named Vm24, which stands for peptide of the venom from V. mexicanus that elutes at 24 min in our experimental conditions. The chromatogram shown in the insert of the left side (FIG. 1) corresponds to the separation of the peptide named Vm23. It stands for peptide of the venom from V. mexicanus that elutes at 23 min. The experimental molecular mass for this component was determined to be 3665 Da.
In vivo Determination of Toxicity of Whole Venom from V. mexicanus and Lethality Tests of Purified Vm23 and Vm24

The effect of venoms and pure peptides is usually conducted in the laboratory using at least three biological models: mammals, crickets and crustaceans, since it is known that scorpion venom contains toxins species specific. There are toxins specific for mammals or for different types of arthropods (reviewed in [Possani et al., 1999]). For the purpose of this invention we conducted experiments using mice as the animal model, because the results would be a reliable indication of what could happen with humans in contact with the venom or purified toxins. Mice injected with various amounts of soluble venom (from 50 to 200 microgram protein per mouse of 20 gram body weight) of V. mexicanus showed no symptoms of intoxication. Usually if the venom contains toxins to humans with these amounts of material a clear symptom of intoxication would have been seen, such as excitability, salivation, respiratory distress (dyspnea) paralysis of rear limbs, diarrhea, convultions, or even death [Possani et al., 1985]. The peptide is said to be "toxic" if the injected animal presents any of the above symptoms, but recovers within 24 hours following the administration of the peptide, whereas if the mouse died it is called "lethal". Non-toxic components are those that induce no symptoms of intoxication and produce similar behavior as mice injected with PBS-saline solution, pH 7.2 [Possani et al., 1985]. Eventually the whole venom at relatively low dosage is not toxic, but purified peptides at similar doses can induce symptoms of intoxication, because during purification the sample is enriched in that particular component. For this reason and taken into consideration that the soluble venom of V. mexicanus was not toxic at 200 microgram/20 gram mouse weight, the pure peptide Vm24 was injected into mice at various concentrations. The highest dose used was 200 microgram/20 grams, that is: 10,000 milligram/kilogram mouse weight and no symptoms of intoxication were observed.

This is certainly in contrast with lethal components, such as toxin Cn2, purified from another Mexican scorpion Centruroides noxius. The fifty percent lethal dose ($LD_{50}$, meaning the dose that causes 50% mortality in a group of animals assayed) for Cn2 in mice is 0.25 microgram/20 gram mouse weight [Zamudio et al., 1992]. It means that Vm24 at an 800-fold higher protein concentration is not toxic to mice, whereas Cn2 kills half the population.
Determination of the Amino Acid Sequence of Vm23 and Vm24

Two techniques were used: automatic Edman degradation and mass spectrometry (MS) analysis. Direct amino acid sequence determination of pure toxin was performed using a Beckman LF 3000 Protein Sequencer (Palo Alto, Calif., USA) with chemicals and procedures provided by the company. A reduced and alkylated sample of the pure peptide was enzymatically cleaved with Arg-C endopeptidase (Roche Diagnostics, Basel, Switzerland), using similar procedures as earlier described for other scorpion components [Valdez et al., 2004; Batista et al., 2007; Diego-Garcia et al., 2007]. The corresponding peptides were purified by HPLC and sequenced. For mass spectrometry the samples were directly applied into a Finnigan $LCQ^{DUO}$ ion trap mass spectrometer (San Jose, Calif.) using a Surveyor MS syringe pump delivery system. The eluate at 10 microliter/min was split in order to allow only 5% of the sample to enter the nanospray source (0.5 microliter/min). The spray voltage was set at 1.7 kV and the capillary temperature at 130° C. For MS/MS experiments, the fragmentation source was operated with 25 V of collision energy, 35-45% (arbitrary units) of normalized collision energy and the scan with wide band activated. All spectra were obtained in the positive-ion mode. The data acquisition and the deconvolution of data were performed with the Xcalibur software on a Windows NT PC system. The MS/MS spectra from peptides enzymatically generated were analyzed manually and by the Sequest software [Batista et al., 2007].

The primary structures of both Vm23 and Vm24 (see FIG. 2) were determined, and the peptides were used for electrophysiological experiments as described below (see accompanying examples 7 to 10 of this invention). The native peptide re-purified from the fraction eluting at 23 min (see inset left in FIG. 1) was fully characterized. Its experimental molecular mass was found to be 3665 Da. One nanomole of this peptide was loaded into the sequencer and the first 34 amino acids were directly identified by Edman degradation (underlined Direct). Cysteine residues were confirmed by reduction and alkylation, using the methodology given by the company (Beckman). The last residue of Vm23 in position 35 was determined by mass spectrometry. The expected theoretical average molecular mass based on the sequence determined was 3665.51 Da, thus confirming the unequivocal determination of the full sequence. Both the experimentally determined and the expected theoretical molecular masses were the same, within the error of the apparatus used (Finnigan ion trap $LCQ^{Duo}$ mass spectrometer).

Figure 2:
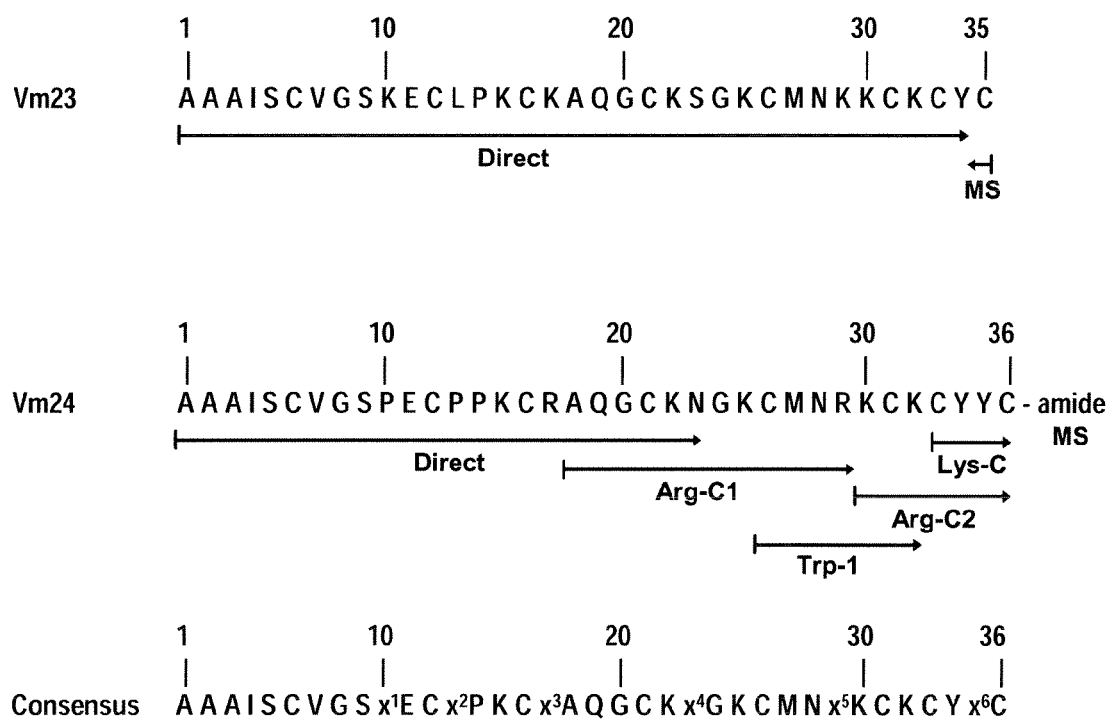

Similarly, one nanomole of the homogeneous peptide Vm24 (re-purified as shown in the inset to the right of FIG. 1) was submitted to automatic Edman degradation, which allowed the identification of the first 28 amino acid residues (FIG. 2, labeled Vm24). Analysis conducted with various aliquots of the reduced and alkylated peptide was used for confirmation of the cysteine residues and for digestion with endopeptidases. The digestion of Vm24 with ArgC-endopeptidase produced three sub-peptides, one that confirmed the sequence from residues Ala1 to Arg17 (not indicated in the figure because it comprises the same N-terminal sequence already determined when analyzing the native peptide—underlabeled "direct"); another from Ala18 to Arg29 indicated by the underlabeled "Arg-C1", and the last one from Lys30 to Cys36 (underlined Arg-C2). These sequences were obtained by Edman degradation in combination with MS/MS fragmentation (see FIG. 2, Vm24). Since the last residues were identified by CID (collision induced fragmentation), the amino acids in positions 30 and 32 could have been either lysine or glutamine (same molecular masses). In order to solve the ambiguity an additional enzymatic cleavage of this last sub-peptide with trypsin was conducted. Three small peptides were separated by HPLC, whose amino acid sequences determined by CID were identified to be from positions Cys26 to Lys30 (underlined Trp1), Cys26 to Lys32 (not indicated, for simplification of notation) and Cys33 to Cys36 (also not indicated). Since trypsin cleaves the peptide bonds at the C-terminal of lysines, these two positions were assigned to be lysine residues, solving unambiguously the full sequence. The last four amino acids at the most C-terminal were also identified by MS/MS fragmentation of a peptide isolated after hydrolysis with Lys-C endoprotease (underlabeled Lys-C). The theoretical average molecular mass of the expected peptide, assuming an amidated C-terminal amino acid was 3863.64 Da and the value found experimentally was 3864.0 Da, confirming the full sequence. Since the accuracy of the three-dimensional ion-traps is in the range of 100 ppm for peptides under 1,000 Da, the small difference of 0.36 units is within the expected value (for reference on the accuracy of the equipment see [Aebersold and Goodlett, 2001]).

Relevant for this invention is important to highlight five characteristics of Vm23 and Vm24:

1) Their primary structures compared with all the other scorpion toxins known to date have more than 50% difference (see example 6 below). This fact justifies the existence of a new sub-family (unknown until today), here proposed to be the number α-KTx 21; examples α-KTx21.1 and α-KTx21.2. It is an original disclosure and definitively shows that both peptides are structurally different from any other such ligands, including those from sea anemone, bees and snake venoms peptides.

2) The N-terminal segments of both sequences up to amino acid in position 10 are identical and 7 of the 8 positions of cysteines that maintain the disulfide bridges are in identical locations of the primary structure. The eighth cysteine (C8) of Vm23 is located in position 35, at the extreme of the C-terminal side, one amino acid earlier compared to Vm24. For this reason Vm24 has 36 residues, whereas Vm23 has 35 amino acid residues. The last cysteine of Vm23 is not amidated, but we assumed that the structural folding is the same as that of Vm24. Since the physiological effects of both Vm23 and Vm24 are comparable it is expected that the amino acid sequence at the N-terminal region is crucial for activity. When comparing the primary structures of Vm23 and Vm24 five differences were found in positions: 10, 13, 17, 23 and 29, and one indel between the last amino acid and the previous one (Y34 in Vm23 and Y35 in Vm24). The most variable region is at the central part of both peptides (residues 10 to 30, in which five out of six differences are located), suggesting that possibly these residues are not so critical for the function of either of the peptides. It is worth mentioning that the substitutions in positions 17 (R/K), 23 (N/S) and 29 (R/K) are conservative modifications, because both arginine (R) and lysine (K) are charged basic amino acids, whereas asparagines (N) and serine (S) are non-charged hydrophilic amino acid residues. The lack of tyrosine in position 35 (substituted for cysteine in Vm23) compared to Vm24, suggests that just one tyrosine is sufficient for the same folding and function of both peptides.

3) The most variable region is thus located at the central part, allowing for conservative substitutions. This can be easily designed by an expert in the field, and modifications or substitutions by amino acid with similar physicochemical properties in aligned positions that shares at least 83% pairwise sequence identity (as shown here for the case of Vm23 and Vm24) are expected to generate a functional equivalent analog with similar properties, and thus should fall within the scope of the present invention.

4) The most important feature, however, as shown and discussed in examples 7 to 10 below is the high affinity that both Vm23 and Vm24 have towards hKv1.3 channels, when compared to other sub-types of potassium channels. Vm23 and Vm24 have higher affinity towards hKv1.3 than the other known blockers, such as Charybdotoxin, Anuroctoxin, BgK, ShK, etc. [Panyi et al., 2006]. The other blockers mentioned above have highly distinct amino acid sequences and/or disulfide pairings, or display a distinct specificity of action and affinity of binding toward Kv1.3 channels. From the simple analysis of the primary structures of Vm23 and Vm24 it is not obvious that they should affect Kv1.3 channels in similar manners as those shown for the other scorpion or sea anemone toxins. In this way, the sequences for which a proprietary information and use is claimed here for Vm23 and Vm24 could not be evident from the knowledge of the other peptides that affect Kv1.3 channels. This invention reports completely distinct and novel amino acid sequences (see SEQ ID NO: 1 and SEQ ID NO:2). Further evidence showing that the determined sequence is correct comes from the results obtained with a synthetically prepared Vm24. Both the native Vm24 and the synthetically prepared have exactly the same physiological actions, as shown below (example 9).

5) Finally another important fact found with these two peptides is that they are not toxic when injected into experimental animals at relatively high concentration (up to 10,000 microgram per 20 gram mouse weight). This is more significant when we compare with other known scorpion venom toxins, e.g. Cn2 from *Centruroides noxius*, as mentioned earlier [Zamudio et al., 1992]. Cn2 injected into mice at about 800-fold lower dose than Vm24 causes 50% mortality.

Example 2

Mass Finger Print Analysis of the Components Present in the Venom of *V. mexicanus*

Scorpion venoms are highly complex mixtures of components, comprising short and long-chain peptides active on ion-channels (reviewed in [Possani and Rodriguez de la Vega, 2006]), free amines, nucleotides, carbohydrates, lipids (reviewed in Possani et al., 1999), enzymes such as phospholipases [Zamudio et al., 1997: Valdez et al., 2004], hyaluronidases and lysozymes [Batista et al., 2007] and many other protein components of unknown function [Diego-Garcia et al., 2007]. Additionally, scorpions are very ancient creatures with more than three hundred million years of evolution on the surface of the Earth and have had time to select specific tools for hunting their preys or for defending themselves from predators. For these reasons it is appealing and wise to search for the presence of biologically active components in their venoms. Thanks to the recent advancement on mass spectrometry methodologies and equipments it is now possible to obtain a mass finger print analysis of the whole venom. For these reasons one of the first studies conducted with the soluble venom of *V. mexicanus* was the identification of the molecular masses of all components, that could be identified by using a Finnigan LCQ$^{DUO}$ (San Jose, Calif.) ion trap mass spectrometer (EIS/MS) and a matrix-assisted laser desorption time of flight (MALDI-TOF), model Ettan MALDI-TOF/Pro apparatus from Amersham Biosciences (Uppsala, Sweden). The strategy used was to pre-select by HPLC separation pure peptides or families of related components eluting as mixtures in the C18 reverse column (FIG. 1) and then analyze their molecular mass by mass spectrometry. In Table 1, the retention time of the fractions collected from the HPLC system is listed followed by the molecular masses of components found in each fraction. Over 340 distinct molecular mass components were determined. It is worth mentioning that some components appear in two contiguous sub-fractions of the HPLC separation system, and in such cases only one was counted. Also some fractions were not identified (labeled ND).

TABLE 1

| RT | Average mass |
|---|---|
| 2.92 | 222.334, 260.168, 372.815 |
| 5.06 | 272.055 |
| B 5.06 | 429.1 |
| 7.40 | ND |
| 9.84 | 1235.349 |
| 10.78 | 994.899, 1047.829, 1234.056 |
| 11.28 | 117.063, 1234.349 |

TABLE 1-continued

| RT | Average mass |
|---|---|
| B 11.28 | ND |
| 13.07 | 300.703 |
| 14 | 1466.168, 1960.937, 2363.969, 2441.293, 3091.036 |
| 14.96 | ND |
| 15 | 272.091, 334.602, 427.197, 1086.902, *1689.2* |
| 16.22 | ND |
| 16.70 | 324.238, 418.72, *501.4*, *834.6*, 1049.296, 1877.397 |
| 17.34 | 261.344, 1205.752, 1274.737, 1876.767, 1886.725 |
| 17.66 | 261.283, 1243.892 |
| 18.35 | 208.909, 223.509, 373.827, 1436.27, 1652.505 |
| 19.10 | 1148.738, 2096.296, 2297.193, 2318.577, 2353.524 |
| B 19.10 | 2377.208, 2593.419, 2610.334 |
| 20.14. | 2593.88 |
| 20.14.2 | 1464.42, 2098.654, 2594.163, 2610.477 |
| 20.23 | ND |
| 20.96 | 1866.081, 3777.92 |
| 21.98 | *431.4*, *714.7*, 1259.696, 3777.049 |
| 22.40 | *533.5*, *788.5*, 2286.744, 4024.456, 4980.605 |
| 23.39 | 1014.47, *1129.8*, 1390.042, 1527.099, 1902.299, 2111.018, 2228.143, 2311.791, 3665, 4025.1 |
| S 24.11 | 1048.604, 1657.949, 2310.809 |
| S 24.11 | 1048.604, 1657.949, 2310.809 |
| 24.11 | 1952.328, 2166.86, 3864, 5338.229 |
| B 24.11 | 253.04, 875.42, 1398.661, 1948.124, 2436.139, 2679.346, 5336.308 |
| 25.10 | *1489.6*, 1511.315, *1617.7*, 2529.512, 3864.577 |
| 25.10.2 | 253.073, *590.4*, 1194.739, 1511.312, 1985.92, 2075.691 |
| 25.52 | 1485.399, 1728.229, 2258.489, 2387.001 |
| 26.10 | *422.3*, *462.4*, 1327.008, 1495.436, 2258.772, 2620.03, 3870.226, 3917.489 |
| 26.51 | 1234.369, 2621.099, 3871.574 |
| 27.12 | 1340.203, 1642.177, 2620.029 |
| 28.24 | 2084.938, 2883.506, 3770.697 |
| 28.72 | 222.295, 373.089, 4037.264, 4062.469, 4860.475 |
| 29.12 | 2028.249, 4044.625, 4743.102 |
| S 29.82 | 1989.272, 2117.962, 3770.356, 3828.061, 4048.342, 5125.488 |
| 29.82 | 2368.289, 2514.764, 3772.141, 4131.437, 4196.231, 5612.061, 5684.0 |
| 30.62 | *1219.7*, 2029.978, 2756.56, 4051.043, 5487.234 |
| 31.20 | 1894.409, 2288.761, *3544*, 3695.567, *3873*, 4053.615, 4623.314, 5309.113, 5468.43, 8340.499 |
| 31.71 | 2526.804, 4053.34, 4256.777, 4623.389, 8184.727 |
| 32.22 | 2610.12, 3068.716, 4050.544, 4251.603, 4616.633, 8157.368 |
| 32.78 | 1727.988, 3115.418, 3838.78, 6231.008 |
| 33.47 | 1288.661, 1630.123, 1856.102, 2076.866, 2116.85, 2306.616, 3302.189, 4160.467, 4322.925, 5434.357, 6514.206, 7937.084, 8364.316, 9125.702, 15373.608 |
| 34.11 | 1811.589, 2792.828, 2890.806, 3272.21, 4008.728, 4044.677 |

TABLE 1-continued

| RT | Average mass |
|---|---|
| S1 35.79 | 3032.485, 3862.668, 7469.49 |
| S2 35.72 | 2558.149, 3032.024, 3987.629, 4232.375, 8260.244 |
| S3 35.79 | 3037.876, 3058.507, 3738.686, 4027.624 |
| 35.79 | 3038.075, 3738.649, 4027.696, 8269.386 |
| 36.19 | 2814.497, 3038.868, 3564.677, 3721.56, 3807.978, 3878.666, 4027.936, 8267.094, 13944.696 |
| 36.72 | 3588.529, 3610.297, 3625.895, 3983.521, 4020.726, 4223.762 |
| 46.53 | 3915.145, 4051.546, 4319.845, 4710.326, 4782.406, 4868.122, 5107.706, 7067.905, 13435.689 |
| 46.86 | 3920.472, 4236.709, 5044.021, 5182.747, 8246.293, 11459.022, 13358.3, 16209.23 |
| 47.82 | 4298.5, 4700.818, 5272.777, 12469.982 |
| 48.70 | 2166.644, 2304.621, 2569.271, 2768.228, 3278.62, 3424.448, 3819.497, 3916.217, 4265.672, 4292.422 |
| 49 | 5953.928, 11315.991 |
| 49.6 | ND |
| 50.75 | ND |
| 51.66 | ND |
| 52.34 | ND |
| 53.31 | 3460.978, 3807.741, 5673.486, 10978.726, 16185.602, 24611.234 |
| 53.84 | 3548.378, 3591.69, 3899.344 |
| 54.27 | ND |
| 55.20 | ND |
| 56.27 | 1603.661, 1640.656 |
| 58.92 | ND |

Components labeled with bold figures mean that they were present in higher concentration in the venom, whereas those in italic figures mean the component was identified only on the EIS/MS spectrometer. When the time of retention is preceded by the letter S means that the chromatographic peak was not symmetrical, and the fraction collected corresponds to the ascending segment of the curve, whereas if the letter is B it means the descending segment of the curve. Italic figures mean that the corresponding molecular mass was obtained only by EIS/MS. Some values were not determined (ND).

The various components registered in Table 1 were analyzed and arbitrarily grouped according to molecular weight in increments of one thousand, starting with those that had less than 500 Da, then from 500-1000, 1000-2000 and so forth up to 9000-10000 Da (by 1000 difference each group). More than 90% of the components identified have molecular masses under 10,000 Da of molecular weight. Three groups had at least 60 different components. They fall within the range of 1000-2000; 2000-3000 and 3000 to 4000 Da. More than 40 components had from 4000 to 5000 Da molecular masses.

These results were important for choosing the appropriate peptides for functional analysis. The rationale used is discussed and published in a recent paper by our group using *Tityus stigmurus* scorpion [Batista et al., 2007], in which a comparative analysis was conducted taken into consideration various mass finger print analyses of different species of scorpions (not included *V. mexicanus*). It is common to find that peptides with molecular weights in the order of 4,000 Da are specific for the recognition of ion-channels permeable to $K^+$ ions. For this reason we have selected peptides in this range of molecular masses for the physiological studies, described below. By following this strategy the two peptides: Vm23 and Vm24 were selected for primary structure determination (FIG. 2) and further physiological assays (see below, examples 7-10).

Example 3

Characterization of the C-Terminal Amino Acid Sequence of Vm23 and Vm24

Concerning the last residue at the C-terminal amino acid sequence of Vm23 the results are clear. The sequence analysis described in example 1 of this disclosure, whose sequence is shown in FIG. 2, leaves little doubt that the last residue is not amidated and terminates the primary structure with a free carboxyl cysteine residue.

Figure 3:
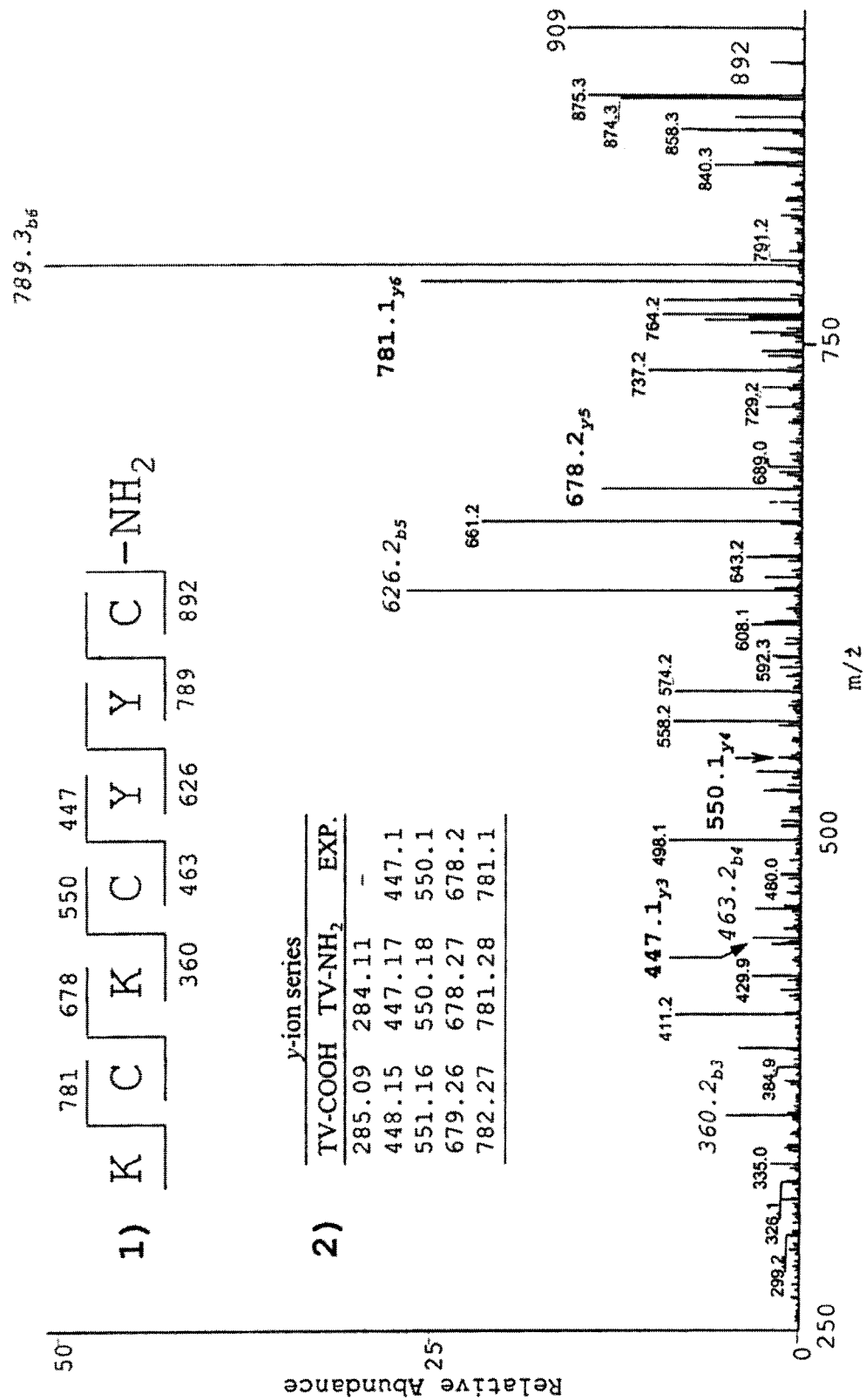

However, for Vm24 the mass spectrometry results suggest that the C-terminal residue could be amidated. The literature reports examples where the amidation of the last amino acid of a given peptide is important for defining its biological function. One such example is the case found for toxin HsTx1 of the scorpion *Heterometrus spinnifer* [Lebrun et al., 1997]. Electrophysiological experiments have demonstrated that the amidated form of this toxin is 5-fold more potent than the free-carboxyl-terminal form and it is up to 300-fold more active in binding experiments to rat brain synaptosomes [Lebrun et al., 1997]. For this reason it was very important to be sure of the chemical form of the last residue of Vm24. As mentioned in the discussion of example 1, the experimental molecular mass found for Vm24 was 3864 Da, and the theoretical molecular weight expected from the amino acid sequence shown in FIG. 2 was 3864.6 Da. The two values are different by 0.6 a.m.u which could be attributed to the presence of an amidated C-terminal residue of Vm24. Collision induced dissociation (CID) experiments performed with the C-terminal peptide (909.4 a.m.u.-monoisotopic mass) produced by Arg-C cleavage show all y ion series values 1.0 a.m.u. lower than those theoretically expected for a free carboxy-terminal peptide and exact values for the b ion series, confirming that the C-terminal of the toxin is amidated (FIG. 3).

For this experiment an aliquot of 25 micrograms protein of Vm24 was enzymatically cleaved with the enzyme Arg-C, using the same procedure described in example 1 above [Valdez et al., 2004; Batista et al., 2007]. The product of enzymatic hydrolysis was separated by HPLC in the same system as described in FIG. 1. All peptides in homogeneous form were systematically analyzed by MS and the peptide with molecular mass of 909.5 a.m.u. was submitted to MS/MS analysis. The experimental protocol set for the nano spray ionization source of the mass spectrometer was 130° C. for the heating capillary and 1.65 kV as spray voltage. Surveyor solvent delivery system was operated with 0.6 microliter/min using 50% acetonitrile (AcCN) in the linear mode. The MS/MS scans were defined with 200 scans/milliseconds of injection time, wideband activated, 25 V collision energy, 1.0 (m/z) isolation width and 40% normalized collision energy. The data were analyzed manually and automatically using MS-product tool of the Protein Prospector (http://prospector.ucsf.edu/) developed by the University of California—San Francisco Mass Spectrometry Facility. The MS-product tool allowed the estimation of the possible ion fragments produced for the peptide KCKCYYC using monoisotopic mass, unmodified cysteines, and unblocked N-terminal residue. The calculation was performed for both the free carboxylic acid terminal and the amidated C-terminal peptide. An ESI Ion Trap instrument was chosen for this evaluation. The theoretical fragmentation of the amidated C-terminal peptide was performed using the Protein Prospector, which showed the exact same values for those obtained experimentally for b (232.11, 360.21, 463.22, 626.28 and 789.34) and for the y ions (782.27, 679.26, 551.16, 448.15, 285.09 and 122.03). Therefore, the Vm24 peptide possesses the C-terminal amidated, that is, a cysteinamide residue.

Example 4

Determination of the Disulfide Bridges of Vm24

Due to its small size Vm24 toxin is an ideal molecule for studying structure-function relationships. The peptide contains eight cysteine residues, located at positions 6, 12, 16, 21, 26, 31, 33 and 36, which form four intramolecular disulfide bonds. This example describes the determination of the disulfide bonding pattern of Vm24 using Edman degradation and mass spectrometry determination of peptides purified by RP-HPLC columns, after cleavage with proteolytic enzymes.

The disulfide pairing was determined by mass spectrometry analysis of peptide fragments obtained after endopeptidase cleavage of pure toxin and their separation by HPLC. A sample of toxin containing 25 micrograms of protein was incubated with an equal mixture (0.5 microgram each) of chymotrypsin and trypsin (Boehring Manheim, Germany) in 150 mM Tris-HCl, pH 6.8, for 12 h at 37° C. The peptides generated were separated by HPLC using a C18 reverse phase column (catalog number 218TP54, from Vydac, Hisperia, Calif.). A linear gradient from solvent A (0.12% TFA in water) to 60% solvent B (0.10% TFA in acetonitrile) was applied to the column and run for 60 minutes. The effluent peaks were collected and immediately freeze-dried. Individual peptides were analyzed by mass spectrometry fragmentation (MS/MS) from which the amino acid sequence was obtained. Since the primary structure was known, the assignment of the disulfide bridges could be inferred.

Figure 4:
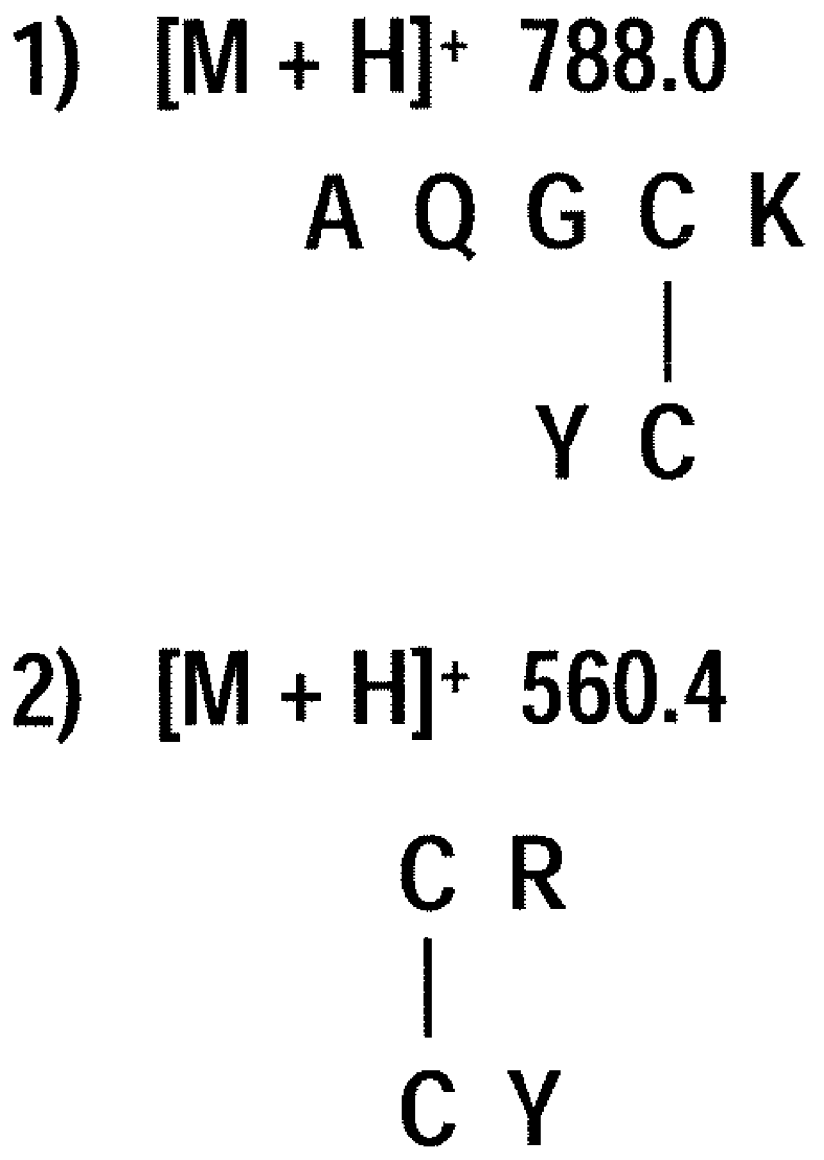
Figure 5:
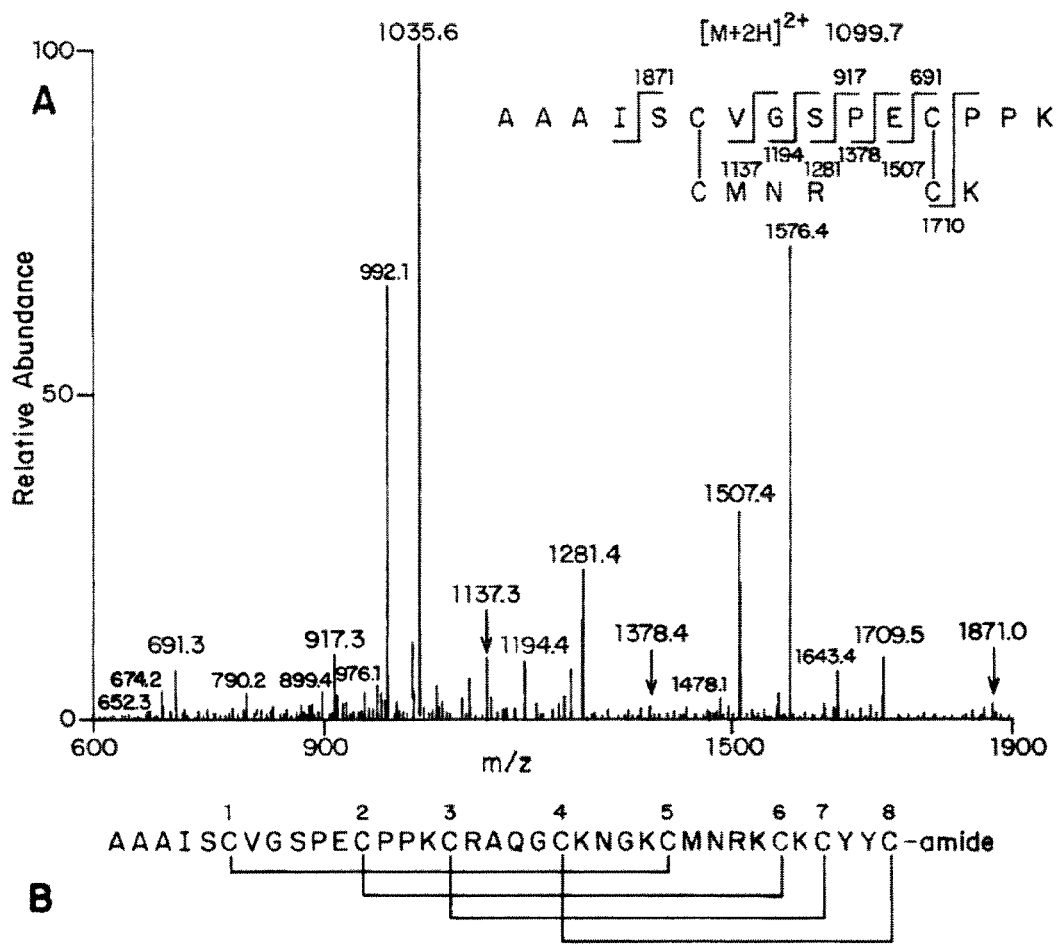

Molecular mass comparison of reduced and oxidized forms of Vm24 show exactly 8 a.m.u. difference; the experimental molecular mass found for the native peptide was 3864.0 a.m.u. and for the completed reduced peptide was 3872 a.m.u, confirming that all cysteines are involved in disulfide bridge formation. Three main peptide fragments were obtained from simultaneous chymotrypsin and trypsin digestion at pH 6.8 (slightly acidic pH in order to prevent mix disulfide rearrangements), showing mono-isotopic molecular masses of $[M+H]^+$ 788.0, $[M+H]^+$ 560.4 and $[M+2H]^{2+}$ 1099.7 a.m.u. (FIGS. 4-1, 4-2 and 5A). The peptide with $[M+H]^+$ 788.0 corresponds exactly to the expected molecular weight of the cystine-pairs (C4-C8), of the heterodimer amino acid sequence AQGCK-CY (FIG. 4-1). The second disulfide bridge determined was C3-C6 that has equal theoretical and experimental values of 560.4 a.m.u. (FIG. 4-2). Both peptides were further characterized by CID experiments showing the expected amino acid sequences. The signal at m/z $[M+H]^{2+}$ 1099.7 a.m.u. (2197.4 deconvoluted mass) comes from the heterodymer core containing the last two cystine half-pairs (FIG. 5A). This fragment was directly analyzed. The CID ions series from the signal at m/z $[M+H]^{2+}$ 1099.7 shows two ion values that satisfy the condition for the complete determination of the last two cystine pairs. The b ion at 1507.4 and the y-ion at 691.3 that are products from the same amide cleavage bond between the glutamic acid (E11) and Cysteine (C12) clearly assign the C1-C5 and C2-C7 half-pairs. Furthermore, the in tandem fragmentation values from the b-ion 1710.5 to b-ion 1137.3 characterize the internal tag (GSPEC-C) with unequivocal mass values confirming the disulfide bridge arrangement schematically represented in the FIG. 5B).

Example 5

Chemical Synthesis of Vm24

In this example and before describing the chemical synthesis of Vm24 it is important to cover some basic concepts in the subject of peptide chemistry and the rationale for the production of ligands by chemical synthesis, rather than by natural extraction of the existing products.

Many toxic polypeptides have been purified from venom sources and were shown to be valuable tools to study cellular communication, because they affect the ion distribution across the biological membrane by binding to receptors (mostly ion-channels for the case of scorpion toxins) and they cause cell depolarization or modulation of the electrical potentials across the membranes, in this way controlling cellular function. For these reasons, finding specific toxic peptides that can discriminate distinct types or sub-types of ion-channels are valuable therapeutic leads in the treatment of a range of physiological or abnormal conditions of experimental animals, and eventually for treatment of human pathologies. Most of the known peptides are short, well folded and packed structures presenting a series of advantages over other organic compounds, such as high potency, good target specificity, high solubility and rapid onset of action. Furthermore they are often small proteins cross-linked by several disulfide bridges. These structural characteristics confer to these peptides a high degree of stability, although the correct folding of a synthetically prepared derivative poses some additional problems for proper synthesis. However, the amounts of these polypeptides present in venom sources usually are quite small. Actually, since they are so specific and efficient in their physiological actions, the animal that produces these peptides does not need to produce great quantities in order to use them in an effective manner, either for capturing their preys or defending themselves from predators. Although the amounts of these various peptides directly isolated from the sources usually are enough to characterize the general mechanism of action and have allowed, in the past, the conduction of structural characterization of the peptide, mainly by nuclear magnetic resonance techniques, usually it is necessary to produce the same peptide or their derivatives synthetically, depending on the scope pursued by the investigation or clinical applications. The determination of the three-dimensional structure of the peptides and the identification of the surface implicated in the recognition of the receptor sides (ion-channels) are fundamental for the design of modified versions of the initial model or for the synthesis of peptidomimetics.

Here we describe the chemical synthesis of Vm24. Historically Vm24 was identified earlier than Vm23. For this reason most of the detailed work, subject of this invention, was done and described here for the case of Vm24, and then was confirmed to be true for both peptides.

A linear analog of Vm24 was synthesized by solid-phase methodology on Rink Amide MBHA resin, (Calbiochem-Novabiochem Corp). Fmoc-amino acids (Calbiochem-Novabiochem Corp) were used with the following side chain protection Arg(Pbf), Asn(Trt), Cys(Trt), Gln(Trt), Glu(OtBu), Lys(Boc), Ser(tBu), and Tyr(tBu).

The Fmoc group was removed by treatment with 20% piperidine in dimethylormamide (DMF) for 20 min followed by wash with DMF. Fmoc-amino acids (0.5 mmol) were coupled as active esters preformed in DMF with HBTU (2-(1-H-benzotriazol-1-yl)-1,1,3,3-tetramethyl-uronium hexafluorophosphate)/DIEA (diisopropylethylamine) (0.45 mmol/0.75 mmol, 2 min activation) as activating agents. Coupling times were 30 min. Unreacted or deblocked free amines were monitored through the ninhydrin test, (Sarin et al 1981) in every cycle of the peptide synthesis. During the entire synthesis, before coupling the next amino acid, the undesirable residual free amines were blocked by acetylation. All the operations were performed manually in a 50 ml glass reaction vessel with a Teflon-lined screw cap. The peptide-resin was agitated by gentle inversion during the Nα-deprotection and coupling steps.

Following final removal of the Fmoc-group, the peptide resin (1.7 grams) was cleaved from the resin and simultaneously deprotected using reagent K [Drakopoulou et al 1995] for two hours at room temperature. Following cleavage, the crude peptide was precipitated and washed with ice-cold t-butyl ether, then dissolved in 20% aqueous acetic acid. The product was lyophilized and kept desiccated at −20° C. until used.

Figure 6:
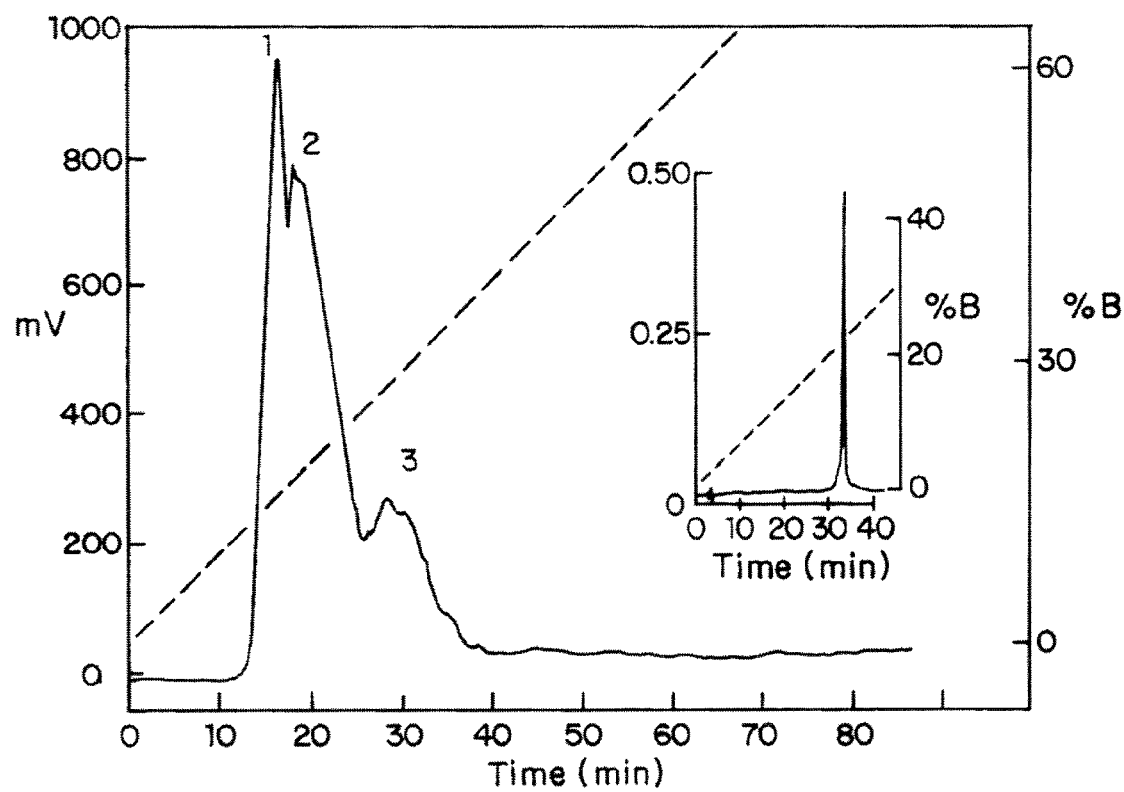

The cyclization reaction to make the corresponding disulfide bridges of the molecule was carried out in 0.1 M NaCl, 5 mM reduced glutathione, 0.5 mM oxidized glutathione, 20 mM $Na_2HPO_4$ (pH 7.8) and 30 µM of unfolded synthetic Vm24. The crude cyclized product was purified in two steps by HPLC. The first used a $C_{18}$ preparative column (238TP1022 Vydac), with a linear gradient of solution A (0.12% TFA in water) to solution B (0.1% TFA in acetonitrile) run up to 60% B in 60 min. The profile of the chromatogram obtained is shown in FIG. 6. The main component (labeled number 1 in the FIG. 6, was finally purified using a $C_{18}$ analytical column (218TP54 Vydac) run with linear gradient from solvent A to 40% B in 60 min. (inset of FIG. 6) The structure and the purity of the synthetic toxin were confirmed by analytical HPLC, amino acid sequence and mass spectrometry determination. Amino acid sequence was carried out in a Beckman LF3000 Protein Sequencer (Fullerton, Calif.) and mass spectrometry analysis was done in a Finnigan-$LCQ^{Duo}$ spectrometer (San Jose, Calif. USA). The correctness of the amino acid sequence was verified by direct Edman degradation up to residue number 30. The elution time from the HPLC column coincided exactly with the time where the native peptide elutes from the same column in identical conditions. Examples of the elution pattern obtained with native Vm24 (FIG. 7A), synthetic Vm24 as described here (FIG. 7B) and an equimolar mixture of native and synthetic Vm24 (FIG. 7c) are shown in FIG. 7. The molecular mass determined by mass spectrometry was 3864 Da, showing that it corresponds exactly to that of the expected sequence. It is worth noting that the resin used is designed for the production of a C-terminal amidated peptide, exactly as it is the case for Vm24.

From about 1.7 grams of resin containing the synthetically prepared peptide with the expected primary sequence of Vm24, about 300 milligrams of corrected folded peptide was obtained, representing a yield of 30% of theoretical expected value (from the starting resin)

Example 6

Amino Acid Sequence Comparison

The sequences of SEQ NO: 1 and SEQ NO: 2 show some resemblance with other short chain scorpion toxins classified within the α-KTx family [Tytgat et al., 1999], such as short peptide chain, rich in basic amino acid residues and similar cysteine pattern. All the members of this family are structurally related and perform similar functions as potassium channel blockers; nonetheless, they display variable selectivity for certain types and subtypes of potassium channels [Rodríguez de la Vega and Possani, 2004; Panyi et al., 2006]. The rationale followed by the international panel of experts which proposed the classification was that a given subfamily could be identified by a high percentage of similarity amongst its members and a low identity with members of other subfamilies [Tytgat et al., 1999]. Later, it was demonstrated that this distinction mirrored, to some extent, the pharmacological spectrum of most subfamilies [Rodríguez de la Vega et al., 2003; Zhu et al., 2004]. Hence, taken into consideration the relatively restricted variability of the family—due to its reduced size—, it is important to identify the molecular and structural characteristics that confers a given functional spectrum. This kind of analysis is usually performed by sequence comparison and phylogenetic inference. The idea underlying these comparisons relays on the assumption that those proteins belonging to the same lineage should be related by events of speciation followed or concomitant to duplication and divergence of the ancestral gene(s), making possible the reconstruction of their evolutionary history by bioinformatic analyses and helping to depurate the fitness landscape within a given sequence space [Thornton and DeSalle, 2000; Orengo and Thornton, 2005].

Using programs that perform heuristic searches within local alignments (BLAST [Altschul et al., 1990] and FASTA 3 [Pearson and Lipman, 1988]) for the identification of sequence similarities of Vm24 and Vm23, few relatives were identified with quite low expectance values (E-value >10-5). Closer inspection against all short chain toxins reported to date suggests that Vm24 and Vm23 are possibly novel members of α-KTx subfamily 6 (following the proposal of [Tytgat et al., 1999]). Pairwise comparison, however, reveals low identity with other members of the subfamily (FIG. 8). The extensive sequence diversification of the α-KTx family makes very difficult to resolve whether or not Vm24 and Vm23 belong to any of the 20 previously characterized α-KTx subfamilies. In order to clarify the relationship with the α-KTx family, Bayesian phylogenetic inference analysis was performed as described previously [Bagdany et al., 2005] with MrBayes 3.04b [Huelsenbeck and Ronquist, 2001; Ronquist and Huelsenbeck, 2003], using the multiple sequence alignment of 92 sequences belonging to the α-KTx family Bayesian phylogenetic inference estimates the posterior probability of a given tree topology by a Markov chain Monte Carlo (MCMC)-based sampling procedure over n−1 stochastically generated trees. One Markov chain remains heuristically searching within the tree topology with best posterior probability at a given step of the sampling procedure; evaluated under a specified amino acid substitution model (the overall process is called Metropolis coupling Markov chain Monte Carlo or $MC^3$). For this analysis, four chains with 250,000 trees each were generated under the JTT amino acid substitution model and sampled every 250th iterations. Coalescence was obtained approximately at 175,000 iteration and the remaining 250 trees with best posterior probabilities were merged to calculate a 50% majority rule consensus tree. This tree clearly shows that α-KTx subfamily 6 segregates, in 92% of the final tree set, as a monophyletic group including all of its members and two closely related toxins from subfamily 7. The analysis also places Vm24 and Vm23 as a sister group of this clade (the specific partition prevail in 81% of the final trees, see FIG. 8); which strongly supports that Vm24 and Vm23 constitute a novel α-KTx subfamily. Based on these analyses and taking into considerations the guidelines proposed by the international panel of experts that classified the scorpion toxins specific for K channels [Tytgat et al., 1999] it is certain that Vm23 and Vm24 constitute a novel sub-family of scorpion toxin that recognize K channels. The highest sequence identity between these toxins is located at the C-terminal portion, like other K channel blocker sub-families. The N-terminal segment is the most variable region of this sub-family and only Vm24 and Vm23 present an uncommon continuous triple Alanine segment at the beginning of the sequence.

Example 7

Vm24 Blocks Selectively the Voltage Gated hKv1.3 Channel Over the $Ca^{2+}$ Activated K Channel hIKCa1 of T Cells High Affinity Block of hKv1.3 Channels by Vm24

The block of hKv1.3 channels by Vm24 was characterized in channels expressed endogenously in human peripheral blood T cells [Peter et al., 2001; Bagdany et al., 2005]. The brief description of the procedure for obtaining T cells for electrophysiological experiments is as follows. Heparinized human peripheral venous blood was obtained from healthy volunteers. Mononuclear cells were separated by Ficoll-Hypaque density gradient centrifugation. Collected cells were washed twice with $Ca^{2+}$ and $Mg^{2+}$ free Hank's solution containing 25 mM HEPES buffer (pH 7.4). Cells were cultured in a 5% $CO_2$ incubator at 37° C. in 24 well culture plates in RPMI-1640 supplemented with 10% FCS/Hyclone, Logan, Utah, USA), 100 microgram/ml penicillin, 100 microgram/ml streptomycin and 2 mM L-glutamine at $0.5\times10^6$/ml density for 3-4 days. The culture medium also contained 6 or 8 microgram/ml of phytohemagglutinin A (PHA-P, Sigma-Aldrich Kft, Hungary) to increase K channel expression [Deutsch et al., 1986]. T lymphocytes were selected for current recording by incubation with mouse anti-human CD2 (Becton-Dickinson, San Jose, Calif., USA) followed by selective adhesion to Petri dishes coated with goat anti-mouse IgG antibodies (Biosource, Camarilo, Calif., USA), as described by Matteson and Deutsch (Matteson et al., 1984). Dishes were washed gently five times with 1 ml of normal extracellular bath medium (see below) for the patch-clamp experiments.

Whole-cell currents were measured in voltage-clamped T cells using an Axopatch 200A or Multiclamp 700B amplifiers connected to personal computers using Axon Digidata 1200 or Digidata 1322A data acquisition hardware. Series resistance compensation up to 85% was used to minimize voltage errors and achieve good voltage-clamp conditions. For data acquisition and analysis the pClamp8 or pClamp9 software package (Molecular Devices Inc., Sunnyvale, Calif.) was used. Prior to analysis whole-cell current traces were corrected for ohmic leak and digitally filtered (3 point boxcar smoothing). Determination of the peak currents at high degree of current block was done by fitting a rising fourth power exponential function to the data traces [Hodgkin-Huxley model] with time constants fixed to the ones determined in the absence of the toxin to isolate the amplitude of the rising component.

Pipettes were pulled from Clark GC 150 F-15 borosilicate glass capillaries in five stages and fire polished resulting in electrodes having 2-3 mega Ohms resistance in the bath. The bath solution consisted of (in mM): 145 NaCl, 5 KCl, 1 $MgCl_2$, 2.5 $CaCl_2$, 5.5 glucose, 10 HEPES (pH 7.35) supplemented with 0.1 mg/ml bovine serum albumin (Sigma). The measured osmolarity of the external solution was between 302 and 308 milliosmols (mOsm). The pipette-filling solution (internal solution) consisted of (mM): 140 KF, 2 $MgCl_2$, 1 $CaCl_2$, 10 HEPES, 11 EGTA (pH 7.22). The measured osmolarity of the internal solutions was approximately 295 mOsm. Bath perfusion around the measured cell with different test solutions was achieved using a gravity-flow perfusion setup with 6 input lines and PE10 polyethylene tube output tip with flanged aperture to reduce the turbulence of the flow. Excess fluid was removed continuously.

Figure 9A:
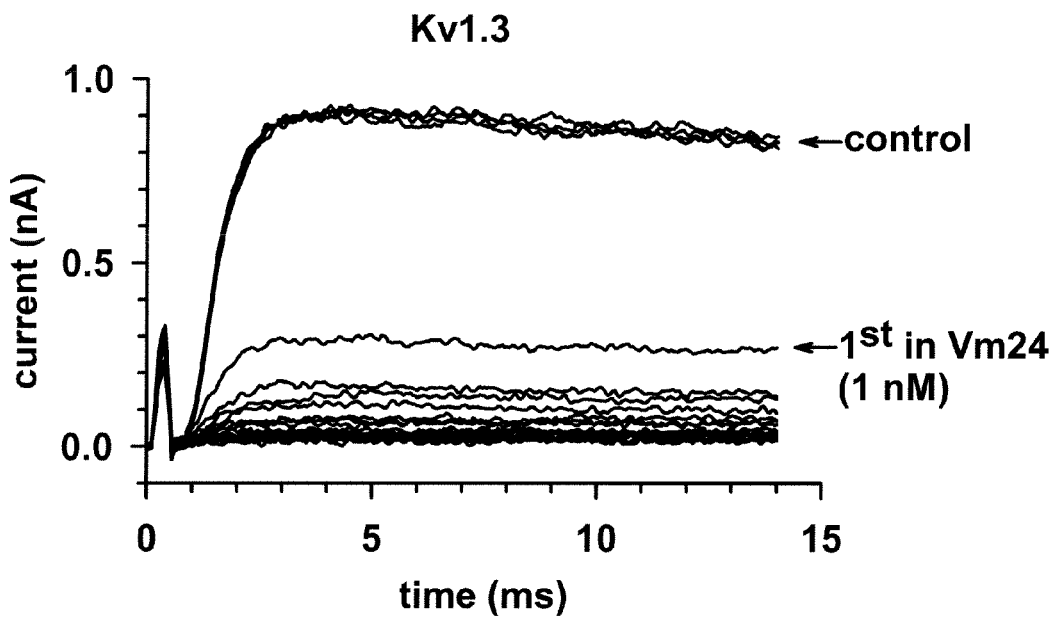

The standard voltage protocol to evoke voltage $K^+$ currents in T cells consisted of a series of 14-ms-long depolarizations to +50 mV from a holding potential of –120 mV. The time between voltage pulses was set to 15 s in order to avoid cumulative inactivation of hKv1.3 channels. Representative current traces in normal bath solution are shown in FIG. 9A (control). Under the experimental conditions applied (the lack of $Ca^{2+}$ in the pipette-filling solution and the nature of the voltage protocol) the whole-cell currents were conducted exclusively by hKv1.3 channels [Peter et al., 2001]. FIG. 9A displays macroscopic $K^+$ currents through hKv1.3 channels recorded sequentially in the same cell, before (control traces) and following the addition of 1 nM Vm24 to the external solution by perfusion. The Kv1.3 current completely disappeared by the $12^{th}$ pulse (corresponding to 3 min) in the presence of 1 nM Vm24.

Figure 9B:
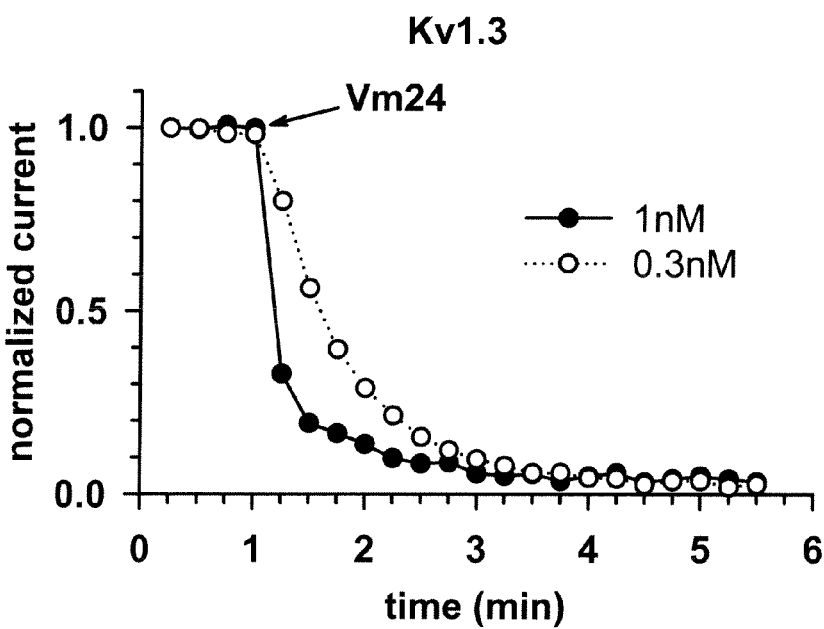
Figure 9C:
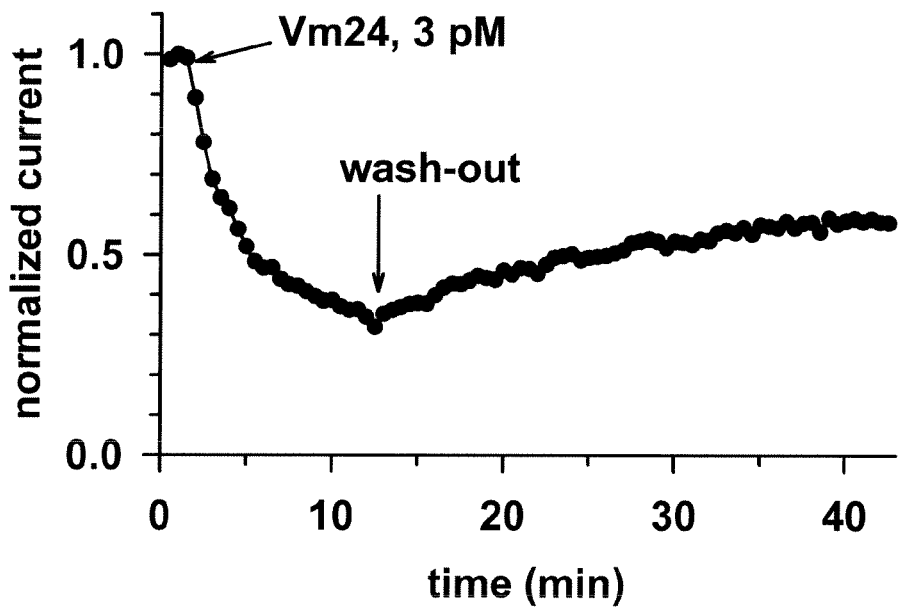

The kinetics of the development of the block at 1 nM (filled circles) and 0.3 nM (empty circles) Vm24 concentrations are shown in FIG. 9B. Following the $4^{th}$ pulse in control solution the extracellular perfusion was switched to a toxin-containing solution and the depolarizing pulses continued every 15 s. Peak currents were determined and normalized to the peak current in control solution and plotted as a function of time. The figure shows that at higher toxin concentration, the kinetics of the development of the block is faster as expected from a pseudo-first order reaction between the toxin and the channels, however, at both toxin concentrations a full block of the whole-cell Kv1.3 current is achieved. Data for 1 nM Vm24 concentration are from the experiment shown in FIG. 9A. Perfusing the recording chamber with toxin-free control solution resulted in a very small relief of the block within the first 8 minutes (not shown). During a 10.5-minute-period of the application of the toxin at 3 pM concentration (FIG. 9C) the loss of the current seems to saturate at ~36% of the peak recorded in control solution. This period was followed by a 30 minute washout period (arrow indicates the start of the perfusion with toxin-free solution) during which one third of the blocked current recovers with an extremely slow kinetics (estimated time constant for washout is ~3800 s corresponding to an off rate of $~2.6\times10^{-4}$ $s^{-1}$).

The general mechanism by which scorpion toxins block K channels is the plugging of the ion conduction pathway upon their binding to the extracellular vestibule of the channel [Goldstein and Miller, 1993]. The slow and incomplete reversibility of the reduction of the currents in the presence of Vm24, however, might indicate a non-specific effect of the peptide on the membrane rather than block of hKv1.3. We argue against this scenario as follows: 1) the rate for the development of the current loss (at high toxin concentrations) depended on the concentration of Vm24, being faster at higher toxin concentrations (FIG. 9B); 2) the leak current did not increase in the presence of the toxin, indicating the lack of the general damage of the membrane by Vm2; 3) Vm24 did not inhibit several other $K^+$ currents or inhibited them quickly and reversibly (see later in the selectivity profile of the toxin) which argues very strongly against a non-specific action of the toxin on the structure of the plasma membrane or a toxin-induced loss of the function of membrane proteins in general; 4) simultaneous application of ChTx, a well-known pore blocker of Kv1.3, and Vm24 showed competition between the two toxins for the same binding site that was evident from the slowing of Vm24 blocking kinetics with increasing concentrations of ChTx (data not shown).

The very slow on and off rates of the toxin imposed limitations on the generation of the dose-response relationship are presented in panel D of FIG. 9. In general, for equilibrium block of the channels at different peptide concentrations the remaining current fraction (RCF) is calculated as $I/I_0$ where I and $I_0$ are the peak currents recorded in the presence and absence of the toxin, respectively. Due to the very slow on rate at low peptide concentrations the determination of I was problematic since the drop in the peak current from episode-to-episode was so small that an apparent saturation was observed during data collection, although the block might not have reached its equilibrium value yet. The use of longer toxin applications was limited by the stability of the peak currents in a whole-cell patch clamp record. Furthermore, rundown of the peaks could not be determined independently due to the extremely long wash-out time of the peptide. Thus, data presented in FIG. 9D represent upper limits for $I/I_0$ values at different toxin concentrations, therefore, the $K_d$ estimated from the dose-response relationship is also an overestimate of the real $K_d$. The dose-response relationship in FIG. 9D was fit with the RCF=$K_d^n/(K_d^n+[Tx]^n)$ function, where [Tx] indicates the toxin concentration, $K_d$ is the dissociation constant, and n is the Hill coefficient. The superimposed solid line shows the best fit with parameters $K_d$=2.9 pM and a Hill coefficient ~1. Error bars indicate SEM (n=3-6). The n~1 value for the Hill coefficient indicates that a single toxin molecule interacts with the channel (1:1 stoichiometry). To the best of our knowledge Vm24 has the highest affinity as a blocker of hKv1.3 in electrophysiological assays.

Vm24 is a Low Affinity Blocker of hIKCa1 Channels

As outlined in the introduction to example 7 one of the most important requirements for a peptide to be a selective immunosuppressant is its selectivity for Kv1.3 over IKCa1. IKCa1 channels are also expressed endogenously in T cells [Grissmer et al., 1993]. The current carried by IKCa1 channels can be measured using a pipette filling solution having 1 μM free $Ca^{2+}$ concentration, which is sufficient to fully activate these channels [Grissmer et al., 1993]. However, the simultaneous presence of Kv1.3 channels in the same cells makes the pharmacological characterization of IKCa1 channels difficult and restricts the study to membrane potentials where Kv1.3 channels are not activated [Grissmer et al., 1993; Bagdany et al., 2005]. This and the relatively small number of IKCa1 channels even in stimulated T cells motivated us to study IKCa1 pharmacology using recombinant channels.

The EGFP-tagged human IKCa1 gene (AF033021) was transfected into Cos-7 cells using Lipofectamine 2000 reagent according to the manufacturer's protocol (Invitrogen, Carlsbad, Calif., USA). The EGFP-tagged hIKCa1 clone was shown previously to have identical biophysical and pharmacological properties to the native IKCa1 in T cells, and thus, has been used widely in pharmacological studies [Wulff et al., 2001]. Cos-7 cells were maintained in standard cell culturing conditions [Bagdany at al, 2005]. Currents were recorded 2-3 days after transfection. GFP positive transfectants were identified in a Nikon TE2000U fluorescence microscope and used for current recordings. The normal extracellular solution is the same as described above. The composition of the pipette filling solution was (in mM) 150 K-aspartate, 5 HEPES, 10 EGTA, 8.7 $CaCl_2$, 2 $MgCl_2$, (pH 7.2). This solution contained 1 μM free $Ca^{2+}$ concentration to fully activate the hIKCa1 current. All other recording conditions (data acquisition, perfusion etc.) were identical to the description above for Kv1.3 channels.

Figure 9D:
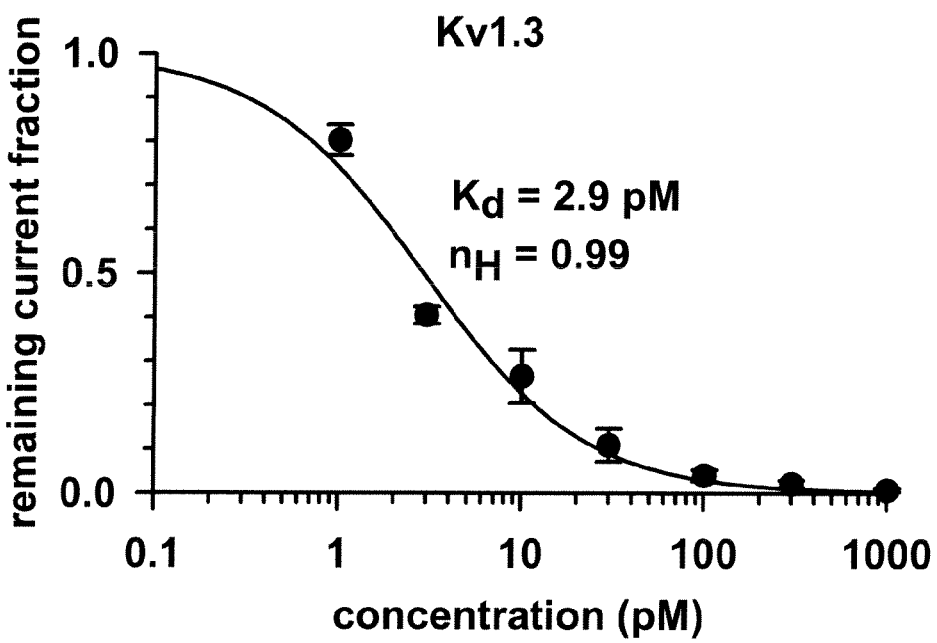
Figure 9E:
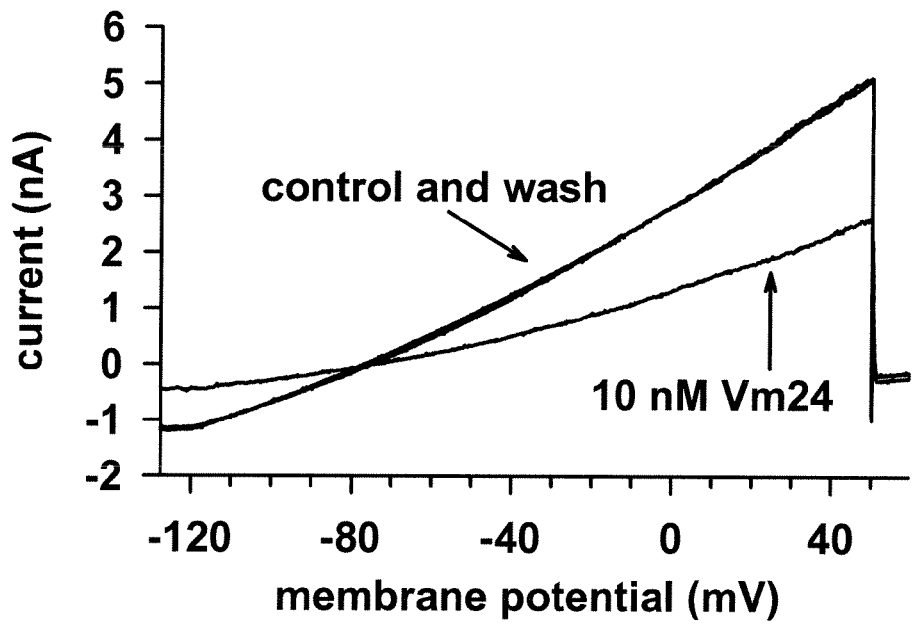
Figure 9F:
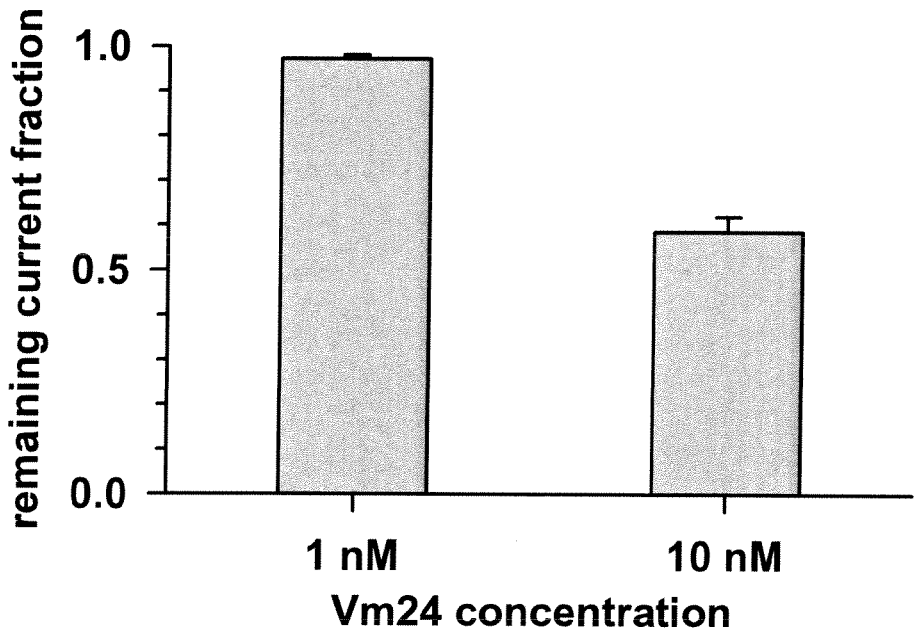
Figure 10A:
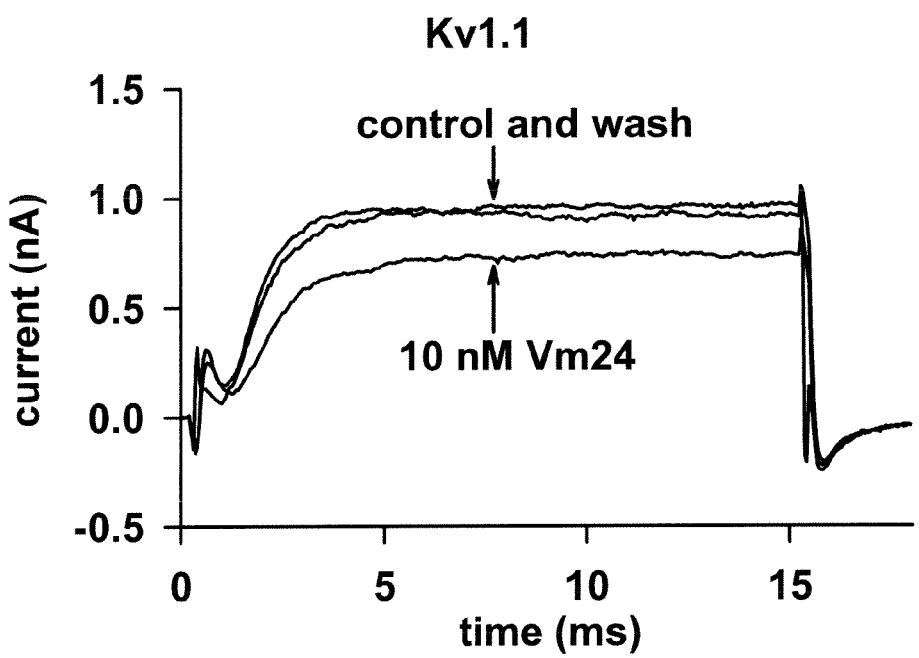
Figure 10B:
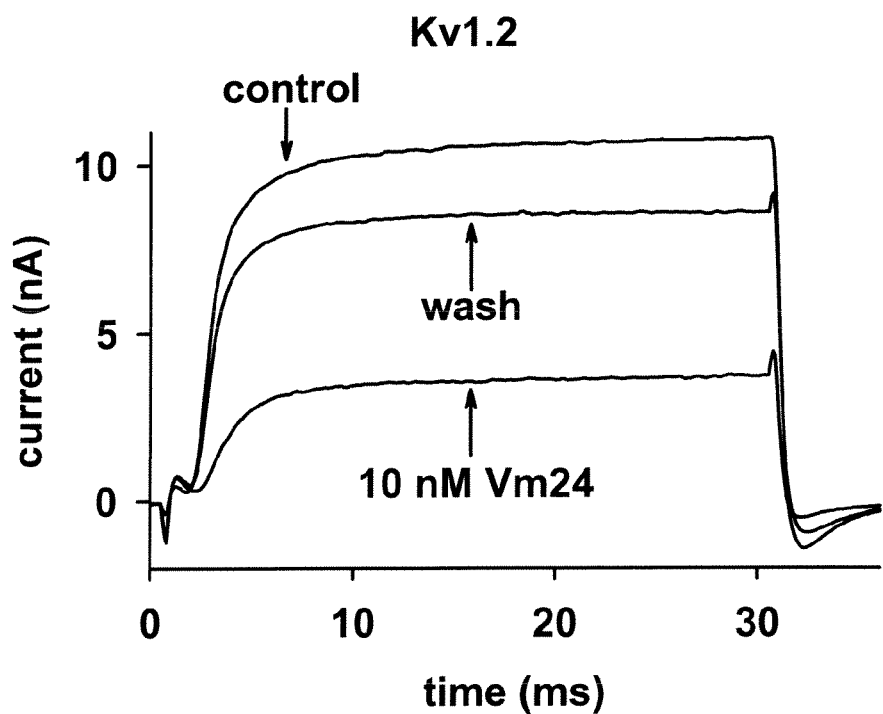
Figure 10C:
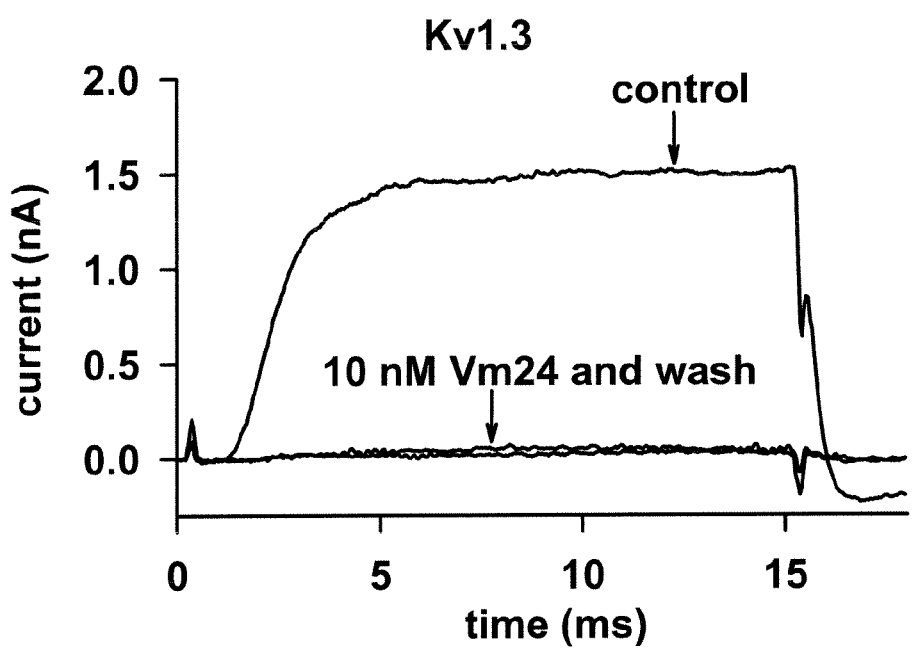
Figure 10D:
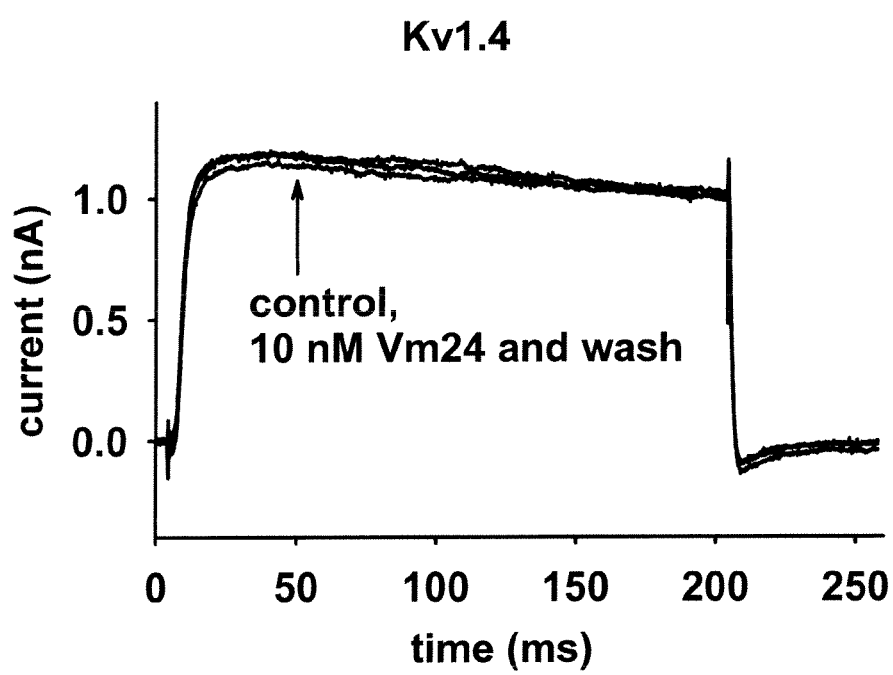

Two hundred millisecond-long voltage ramps from −120 mV to +50 mV from a holding potential of −120 mV were used to elicit hIKCa1 currents in Cos-7 cells (ramp speed 0.85 mV/ms). Voltage ramps were run every 10 s. The current trace recorded in the absence of Vm24 (control) in FIG. 9E shows that pure, non-voltage-gated hIKCa1 currents were evoked by the applied voltage protocol. The reversal potential of the current is −75 mV, which is characteristic to a $K^+$ conductance based on the ionic composition of the recording solutions. For IKCa1 currents the slope (s) of the linear current-voltage relationship can be used to characterize the current block [Grissmer et al., 1993]. The value of s is reduced to ~52% of the control in the presence of 10 nM Vm24 during the experiments shown in FIG. 9E, the equilibrium block is reached in 4.5 min (27 episodes). The current block fully reversed in 2.5 min upon switching the perfusion to toxin-free extracellular solution (FIG. 9 E, wash). The remaining current fractions at 1 nM and 10 nM Vm24 concentrations were calculated as $s/s_0$ where s and $s_0$ are the slopes of the I-V relationships evoked by voltage ramps in the presence and absence of Vm24, respectively, and presented in FIG. 9F. Error bars indicate SEM for n=3 independent experiments. At 1 nM concentration Vm24 practically does not blocks hIKCa1 channels (FIG. 9F) whereas at the same concentration the peptide blocks hKv1.3 channels completely (FIG. 9D). The $K_d$ of Vm24 for hIKCa1 can be estimated from a model where 1 toxin molecule interacts with 1 channel to give a $K_d$ of ~14 nM. Considering the $K_d$ determined for hKv1.3 (2.9 pM) the selectivity of Vm24 for hKv1.3 over hIKCa1 is at least ~4500-fold.

Example 8

Selectivity Profile of Vm24

All channel constructs used in this study are routinely used in pharmacological and biophysical assays and their applicability is confirmed in the listed references.

Transient transfections: Cos-7 cells were used to express rat Kv2.1 (rKv2.1, kind gift from Dr. S. Korn, U. of Connecticut) [Immke et al., 1999]; human Kv1.2 (hKv1.2, pcDNA3/Hygro vector containing the full coding sequence for Kv1.2, kind gift from Dr. S. Grissmer, U. of Ulm, Germany) [Visan et al., 2004]; human Kv1.4 (hKv1.4ΔN: the inactivation ball deletion mutant of Kv1.4, a kind gift from D. Fedida, University of British Columbia, Vancouver, Canada) [Kurata et al., 2004]; and human $Na_V1.5$ (a kind gift from R. Horn, Thomas Jefferson University, Philadelphia, Pa., USA) [O'Leary et al., 1995; Ahern et al., 2005] channels. tsA-201 cells were used to express hBK channels (hSlo1 gene (U11058), in pCI-neo plasmid, gift from Toshinori Hoshi, University of Pennsylvania, Philadelphia, Pa.) [Avdonin et al., 2003]. All these channel clones were transiently co-transfected with a plasmid encoding the green fluorescence protein (GFP) at molar ratios of 1:5 using Lipofectamine 2000 reagent according to the manufacturer's protocol (Invitrogen, Carlsbad, Calif., USA), and cultured under standard conditions. Currents were recorded 2-3 days after transfection. GFP positive transfectants were identified in a Nikon TE2000U fluorescence microscope and used for current recordings (>70% success rate for co-transfection).

Stable cell lines: L929 cells stably expressing mKv1.1 and MEL cells stably expressing hKv1.5 channels have been described earlier [Grissmer et al., 1994] and were kind gifts of Dr. Heike Wulff (UC Davis, Calif., USA). hERG channels were expressed in a stable manner in a HEK-293 cell line.

Whole cell currents were recorded as described in example 7. In all cases standard extracellular and pipette filling solutions were used (see example 7) except for recording hBK currents where the composition of the pipette filling solution was (in mM) 140 KCl, 10 EGTA, 9.69 $CaCl_2$, 5 HEPES (pH 7.2). The free $Ca^{2+}$ concentration of this latter solution is $[Ca^{2+}]_{int}$=5 micromolar, which allows the recording of BK currents at moderate depolarizing potentials [Avdonin et al., 2003]. All other experimental conditions (data acquisition, principles of analysis, perfusion) were the same as described in example 7.

Current traces obtained for members of the Kv1 family (mKv1.1, hKv1.2, hKv1.3, hKv1.4ΔN, hKv1.5) in standard extracellular solution (control) are shown in FIG. 10A through 10E. In all cases cells were held at −120 mV holding potential and repeatedly depolarized to +50 mV to elicit the currents. The duration of the depolarizing pulses (indicated separately in each panel of FIG. 10) was set to allow full activation of the currents and minimize inactivation. In all cases sufficient time was allowed between pulses at the holding potential (−120 mV) for the complete recovery of the channels from any residual inactivation (interpulse intervals ranged from 15 to 30 seconds). The fast (N-type) inactivation removed version of hKv1.4 was used in this study (hKv1.4ΔN, the N-terminal 147 amino acids are deleted). In the absence of N-type inactivation the determination of the current block is easier and more accurate since the peak currents in this clone are not influenced by the very rapid inactivation process (time constant: 15-20 ms, [Kurata et al., 2004]). In the wild type channel due to the competition between time-dependent current activation and inactivation the peak currents are underestimated which complicates the analysis of current block.

Figure 12A:
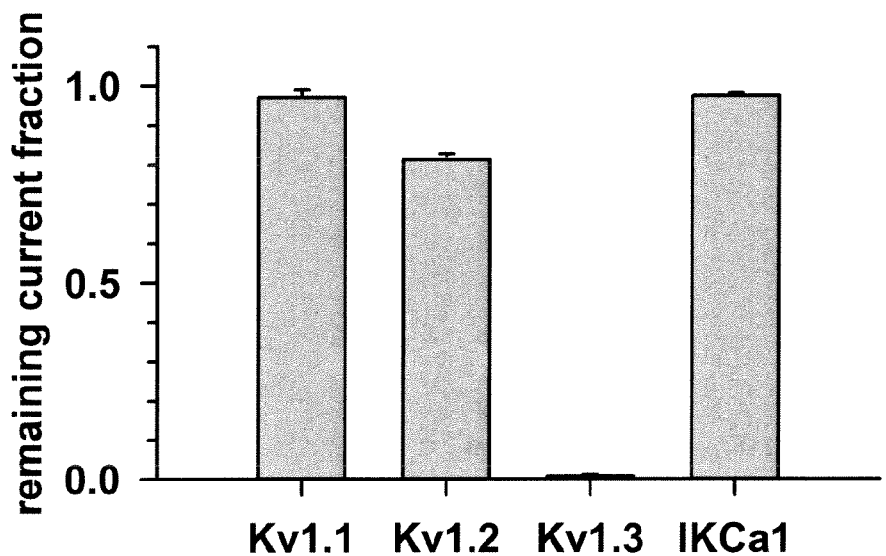

FIG. 10 shows current traces recorded before the application of the toxin (control), following the equilibration of block by 10 nM Vm24 and following wash-out (wash) of the toxin. The analysis of the panels indicates that hKv1.4 and hKv1.5 channels are practically insensitive to Vm24 (see also the bar graph in FIG. 12B). However, Vm24 in 10 nM concentration, which is ~3500 times the $K_d$ for hKv1.3, blocks mKv1.1 channels (RCF=0.80±0.02, n=3) and hKv1.2 channels (RCF=0.54±0.08, n=3) significantly. Moreover, the blockade of hKv1.2 is not fully reversible. The blockade of hKv1.3 current at 10 nM Vm24 concentration (recorded in human T cells) is shown in FIG. 10C for easier comparison of the potency of Vm24 as a blocker of Kv1 channels (RCF=0.01±0.01, n=3). Due to the significant blockade of mKv1.1 and hKv1.2 currents, Vm24 was also tested in lower (1 nM) concentration (FIG. 12A). At 1 nM concentration the RCF values were 0.97±0.02 (n=3) and 0.81±0.015 (n=3) for mKv1.1 and hKv1.2 currents, respectively. From the RCF values the affinity of Vm24 for these channels can be estimated from a model where 1 toxin molecule interacts with 1 channel to give $K_d$ values between 30-40 nM for mKv1.1 and between 5-10 nM for hKv1.2. Considering the $K_d$ determined for hKv1.3 (2.9 pM) the selectivity of Vm24 for hKv1.3 over mKv1.1 and hKv1.2 are at least ~10000-fold and 1500-fold, respectively.

Figure 11A:
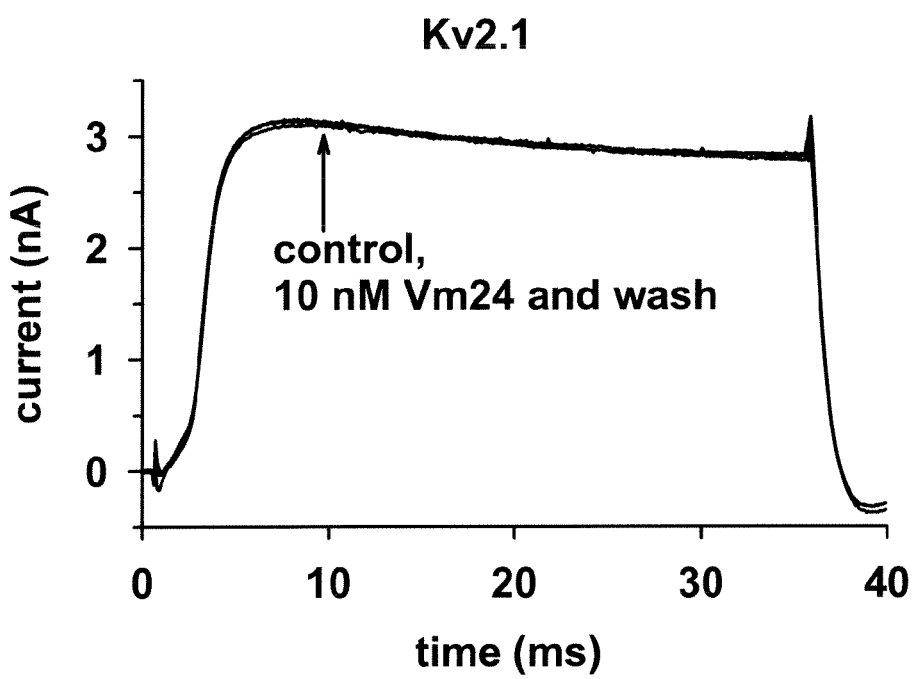
Figure 11B:
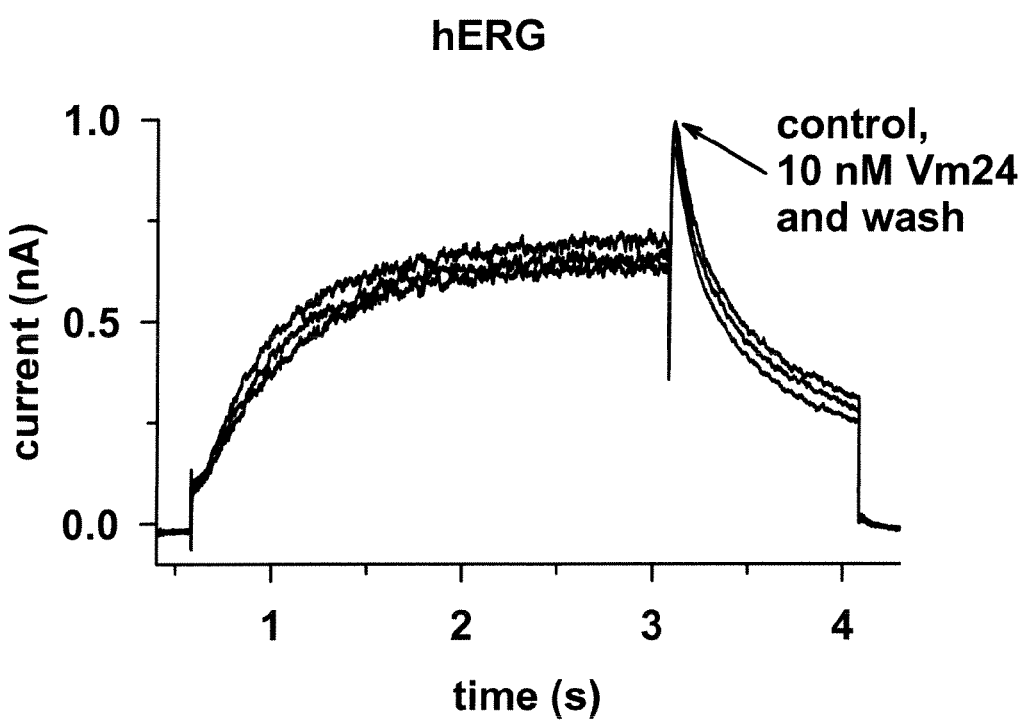
Figure 11C:
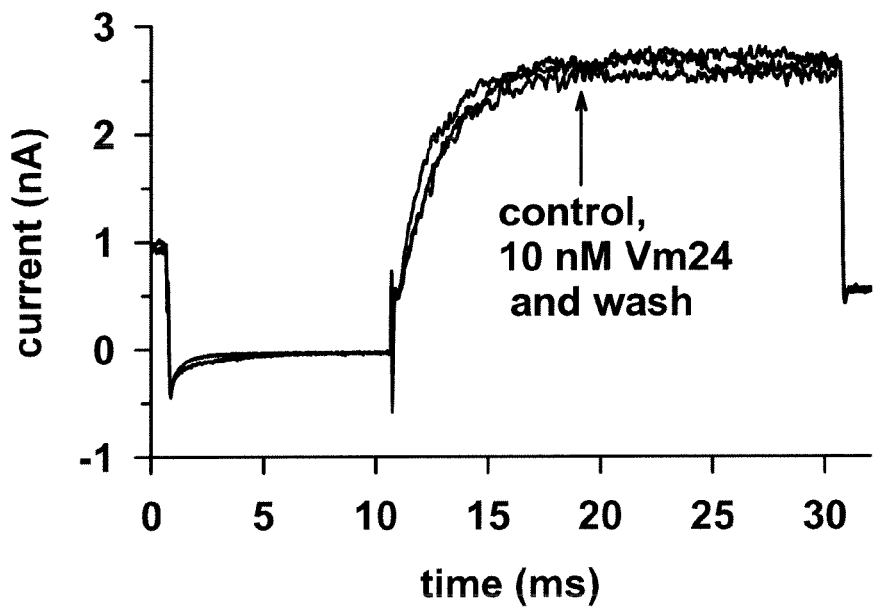
Figure 11D:
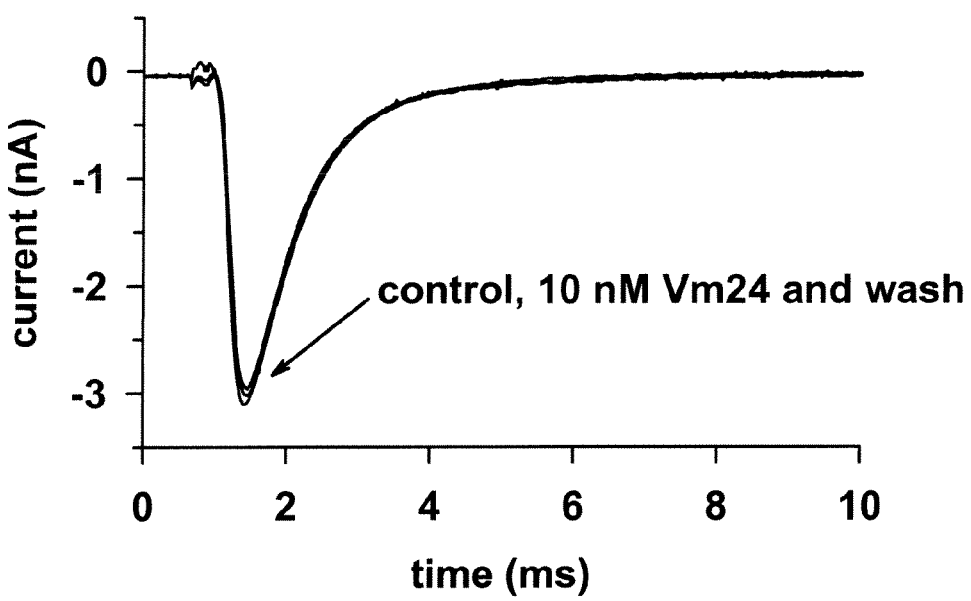
Figure 12B:
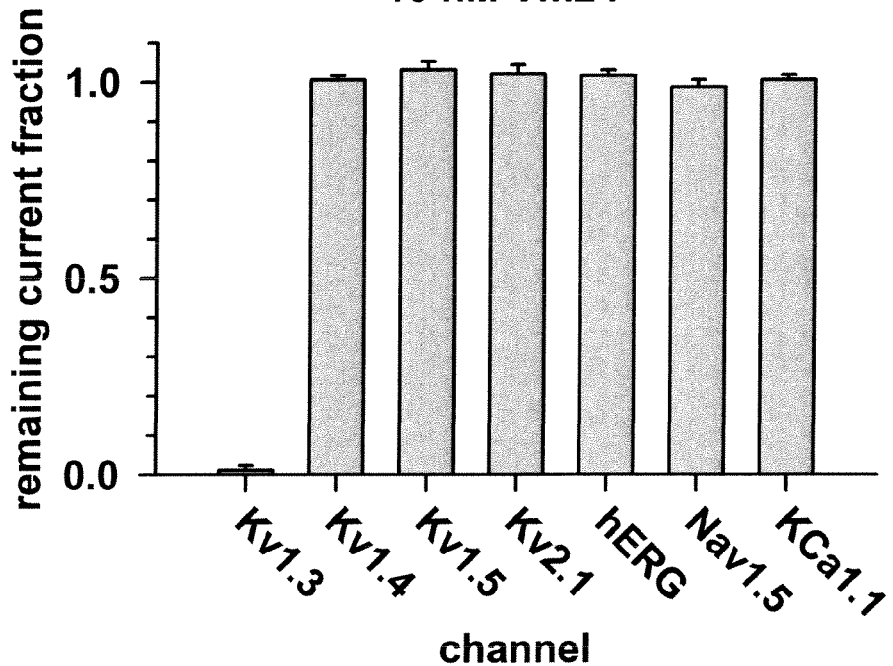

The potency of Vm24 inhibiting the activity of other ion channels having significant biological effect and susceptibility to block by animal toxins was also determined. These included the rKv2.1 and hERG (Kv11.1) voltage-gated K channels, the $Ca^{2+}$-activated K channel hBK (KCa1.1) and the cardiac voltage-gated sodium channel $Na_V1.5$. FIG. 11 shows representative whole-cell currents elicited with voltage protocols appropriate for a given channel in standard extracellular solution (control). Peak Kv2.1 and $Na_V1.5$ currents were determined from records obtained in response to depolarizations to +50 mV and 0 mV, respectively, from a holding potential of −120 mV (FIGS. 11A and 11D). HEK293 cells expressing hERG channels were held at −80 mV, depolarized to +20 mV for 2.5 s to activate and inactivate the channels (FIG. 11B). This was followed by a step to −40 mV at which inactivated channels quickly recover and the peak hERG current can be determined. This complicated voltage protocol is standard for recording hERG currents. BK channels are activated by the depolarization of the membrane (FIG. 11B), however, the voltage dependence of the open probability depends on the intracellular free $Ca^{2+}$ concentration. At a concentration of 5 micromolar free $[Ca^{2+}]$ applied in this study more than 50% of the channels are activated at +50 mV, thus, the comparison of the effects of Vm24 at membrane potentials identical to the ones used for other Kv channels is possible. Full activation of BK channels at +50 mV would require $[Ca^{2+}]$ incompatible with stable whole-cell recording, conversely, full activation of BK channels at 5 micromolar free $[Ca^{2+}]$ would require depolarizations to >+100 mV. Thus, the combination of 5 micromolar $[Ca^{2+}]$ and +50 mV test potential was a reasonable compromise to study the effect of Vm24. The pulse to −120 mV preceding the test pulse was used for the assessment of the nonspecific leak. The holding potential between the pulse protocols was 0 mV at which all Kv channels fully inactivate thereby reducing the possibility of the contamination of the records by endogenous Kv currents sporadically found in tsA-201 cells. At this membrane potential BK channels are already active as it is demonstrated by the significant holding current at the beginning of the pulse.

To assay the effects of Vm24 on different channels shown in FIG. 11 cells were repeatedly depolarized to elicit currents in different extracellular solutions. FIG. 11 shows representative current traces recorded before the application of the toxin (control), following the application of 10 nM Vm24 for 4-7 min., and following wash-out (wash) of the toxin. All panels of FIG. 11 show that the currents recorded in the presence of Vm24 are indistinguishable from the ones recorded in control solution and after washout, indicating the lack of blockade of these channels. The statistical analysis is presented in FIG. 12B where the mean and the SEM of the remaining current fractions are shown in the presence of 10 nM Vm24 (n≧3).

Data presented in FIG. 12 indicate that the order of the blocking potency of Vm24 for various K channels is hKv1.3>>>hKv1.2>hIKCa1>mKv1.1>>>hKv1.4≈hKv1.5≈rKv2.1≈hERG≈hBK≈hNa$_V$1.5. Based on the $K_d$ value obtained for hKv1.3 from the dose-response relationship and the single-point estimates of the $K_d$ values for the other channels (i.e., calculated from data at 10 nM Vm24 and the remaining fraction of the current assuming 1:1 toxin-channel stoichiometry) the selectivity of Vm24 for hKv1.3 over other channels assayed in this study is >1500-fold. This value is well over the commonly accepted criteria for selectivity [Giangiacomo et al., 2004], which is defined as 100-fold difference in the equilibrium dissociation constant or a difference in binding free energy for an α-KTx binding to two different potassium channels, Ch1 and Ch2 of $\Delta\Delta G_{Ch1;Ch2}$>2.72 kcal/mol.

Example 9

Synthetic Vm24 is an Equally Potent Blocker of hKv1.3 as the Natural Toxin

As described in Example 5, theoretical and practical considerations led to the chemical synthesis of Vm24. As described, the structure and the purity of the synthetic toxin were confirmed by analytical HPLC, amino acid sequence and mass spectrometry determination. All these approaches indicated that primary sequence of synthetic Vm24 (sVm24) is identical to that of the natural peptide. Moreover, the protocol for the generation of sVm24 used distinct protecting groups for the thiol groups designed to ensure that folding is restricted to the same disulfide pairing as in the native peptide. These data, however, do not guarantee that the biological activity of the peptide is maintained. The complementary surfaces of the channel and the peptide that mediate high affinity block are very complicated and minimal deviations from the structure of the native peptide might compromise the efficacy of sVm24 in blocking Kv1.3 [Giangiacomo et al., 2004].

Figure 13A:
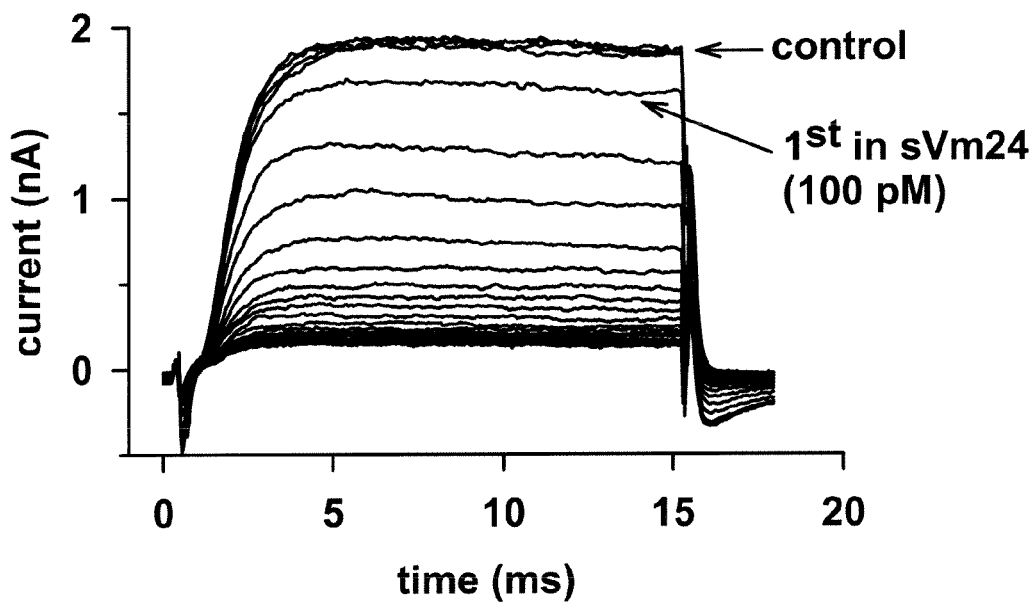
Figure 13B:
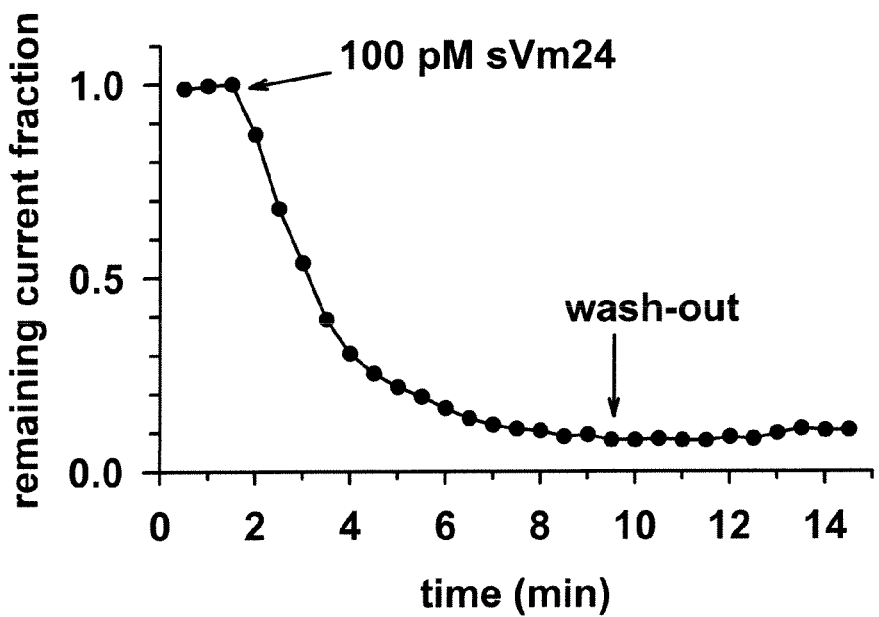

The biological activity of sVm24 was assayed on Kv1.3 channels of human T cells. The experimental conditions for this study were exactly the same as described in Example 7. A whole-cell patch clamped T lymphocyte was depolarized repeatedly to +50 mV from a holding potential of −120 mV every 30 s in the presence of different solutions (FIG. 13A). The hKv1.3 current measured in the absence of sVm24 (control) gradually, and almost completely disappeared upon the administration of 100 pM sVm24 via the perfusion apparatus. After the 16$^{th}$ pulse the recording chamber was perfused with toxin-free extracellular solution. The removal of the toxin from the perfusion solution did not result in a significant relief of hKv1.3 block within 5 minutes. This is demonstrated more clearly in FIG. 13B where the peak currents, normalized to the ones recorded in control solution before sVm24 application (normalized peak), are shown as a function of time. Arrows indicate the start of the perfusion with sVm24 (100 pM sVm24) and the switching of the perfusion to toxin-free solution (wash-out). The remaining current fractions (RCF) measured after equilibration of the block with 100 pM of sVm24 or Vm24 are compared in FIG. 13B (n=6 and n=4, respectively, bars indicate SEM). The statistical comparison (t-test) indicated that the RCFs are statistically not different between the two groups (p=0.57). Our conclusion is that sVm24 is as potent as the natural toxin in blocking hKv1.3 channels.

Example 10

Analysis of the Biological Activity of Vm23 on Different Ion Channels

Scorpion venoms contain a plethora of biologically active peptides. The venom of a given species often contains peptides with high degree of sequence identity, as in case of Vm23 and Vm24 of *V. mexicanus* (see example 1). A high degree of sequence identity of the peptides usually confers identical biological activity to the individual molecules. This originates from the fact that interaction of peptide toxins with the toxin receptor located in the outer vestibule of ion channels is determined by multiple mechanisms, including long-range electrostatic, short-range electrostatic and close-contact interactions, and the net effect of these factors determine the binding affinity and selectivity [Park and Miller, 1992; Peter et al., 2001; Giangiacomo et al., 2004]. It has been shown previously that two peptides of the same scorpion (Pi2 and Pi3 of *P. imperator*), differing in a single amino acid only, both block Kv1.3 in sub-nanomolar concentrations [Peter et al., 2001]. From the pioneering work of Miller and co-workers [Goldstein et al., 1994] it is also evident that even non-conservative amino acid substitutions in several positions of charybdotoxin are well tolerated and the toxin retains its affinity for the Shaker potassium channel (e.g. T9K and N22K). In order to verify that the differences among Vm23 and Vm24 were not significant for changing their affinity and specificity towards Kv1.3 the pharmacological profile of Vm23, was also examined in detail as shown below.

The ion channel blocking potency of Vm23 was assayed for Kv1.3 channels of human T cells, and for mKv1.1, hKv1.2 and hIKCa1 channels. These channels were included in the study based on the low affinity (mKv1.1, hKv1.2 and hIKCa1) or high affinity block (hKv1.3) of these channels by the related peptide, Vm24, which shares 83% sequence identity with Vm23. The experimental conditions were exactly the same as described for the corresponding channels in Example 7 and Example 8.

Figure 14A:
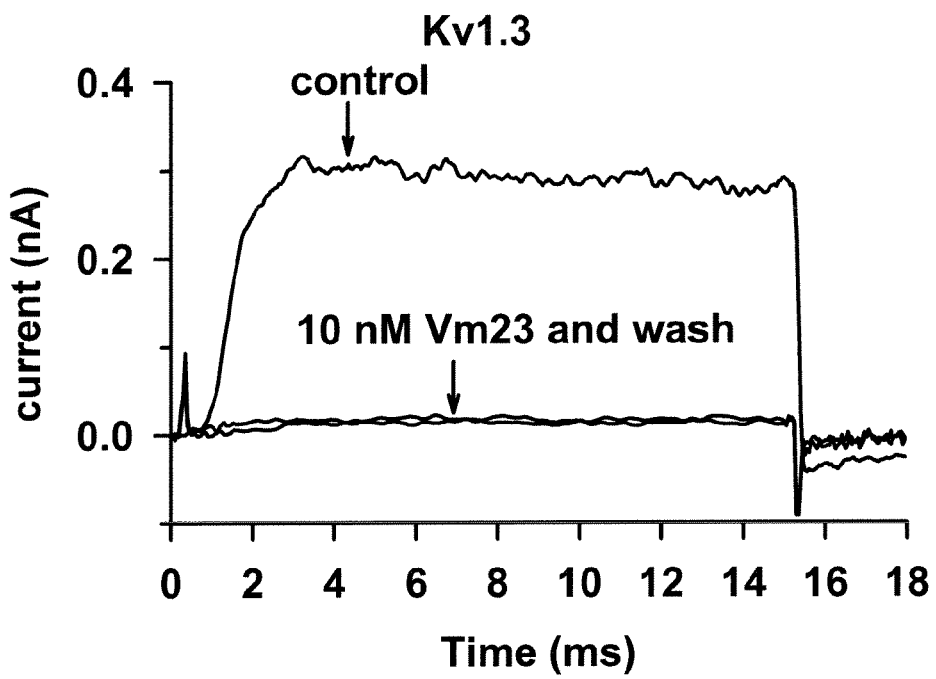
Figure 14B:
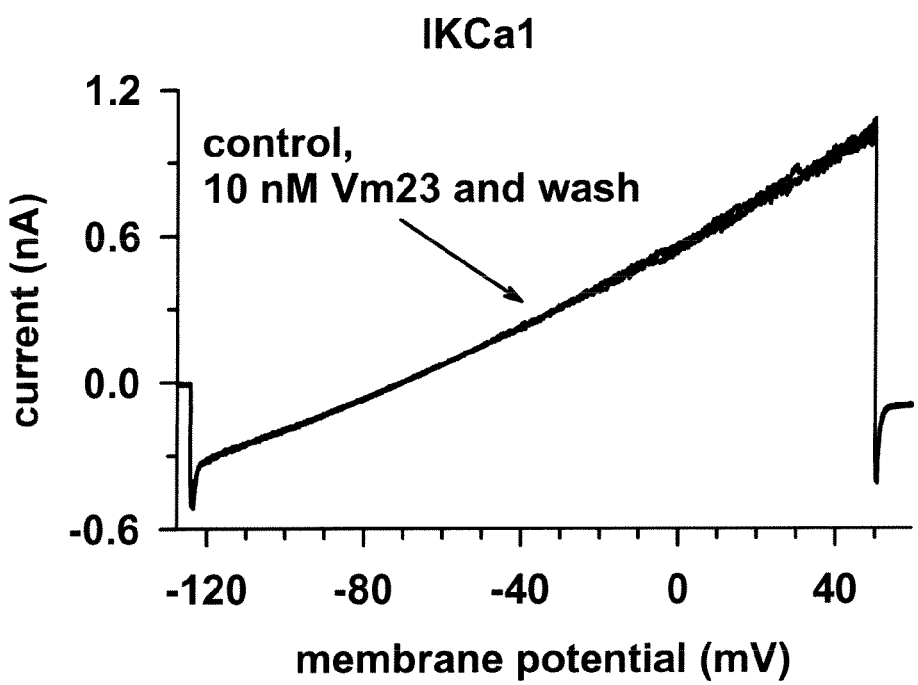
Figure 14C:
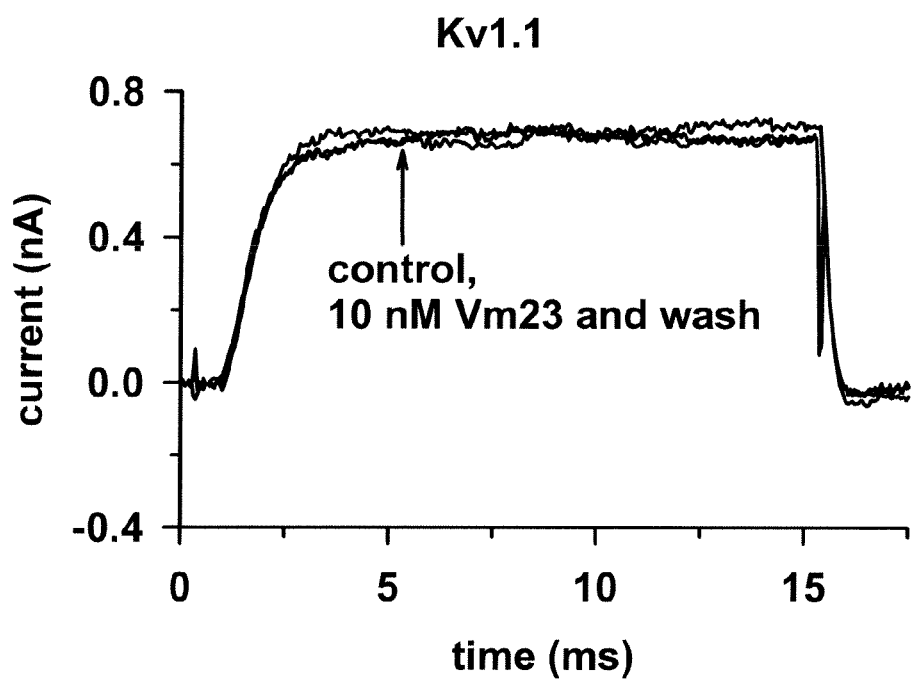
Figure 14D:
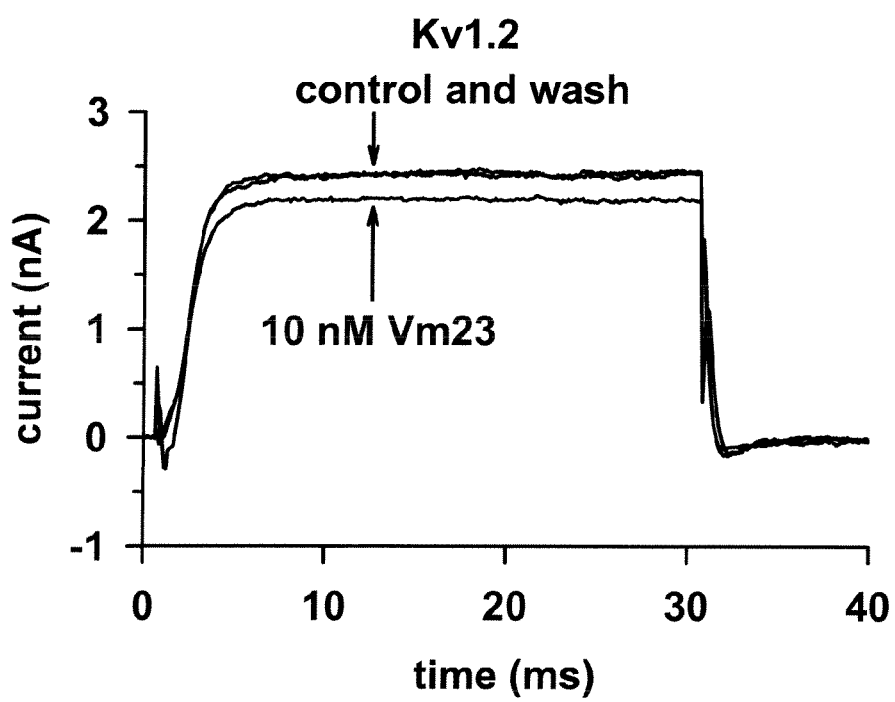

A whole-cell patch clamped T lymphocyte was depolarized repeatedly to +50 mV from a holding potential of −120 mV every 15 s in the presence of different solutions (FIG. 14A). The hKv1.3 current measured in the absence of Vm23 (control) almost completely disappeared within 3.5 min upon the administration of 10 nM Vm23 via the perfusion apparatus. The trace indicated as "10 nM Vm23" was recorded after the equilibration of the block. After the 19$^{th}$ pulse the recording chamber was perfused with toxin-free extracellular solution (wash-out). The removal of the toxin from the perfusion solution did not result in a significant relief of hKv1.3 block within 2 minutes. The remaining current fractions (RCF) measured after equilibration of the block with 10 nM Vm23 are shown in FIG. 15 (n=3, bars indicate SEM). These results indicate that the characteristics of Vm23-mediated block of hKv1.3 channels are very similar to those of the Vm24-mediated block: the block is high affinity and the off rate of the toxin is extremely slow, beyond the time limits used in this assay. The limited amount of Vm23 (less than 0.5% of the venom is Vm23) precluded the determination of the dose-response relationship of hKv1.3 blockade and the proper statistical comparison of the dissociation constant with that of Vm24.

The comparison of the currents recorded before (control), 3.5 minutes after the addition of 10 nM Vm23, and following the wash-out of the toxin (2 min) show that 10 nM Vm23 practically does not block either hIKCa1 channels (FIG. 14B) or mKv1.1 channels (FIG. 14C) (see experimental details in the corresponding sections of Example 7 and Example 8). The complete lack of hIKCa1 blockade by Vm23 is different from the effect of Vm24, which blocked ~40% of the cannels in the same concentration (see FIG. 9F). On the other hand, hKv1.2 channels were slightly blocked by 10 nM Vm23 (FIG. 14D) to give an RCF value of 0.91±0.02 (n=3, SEM, FIG. 15), and the block was not readily reversible within 2 min. The same concentration of Vm24 blocked ~46% of the channels (see Example 8).

Comparison of the remaining current fractions for hKv1.3, hIKCa1, mKv1.1 and hKv1.2 in the presence of 10 nM Vm23 (FIG. 15) with the data obtained for Vm24 (FIGS. 12A and B) indicate that the selectivity profile of Vm 23 for hKv1.3 is slightly better for the tested channels. It can also be concluded from the comparison that despite the differences in the primary structure of Vm23 and Vm24, the high affinity block of hKv1.3 with remarkable selectivity is maintained.

Example 11

In Vivo Immunological Effects of Vm24

Millions of people worldwide are affected by autoimmune diseases, such as but not limited to multiple sclerosis, rheumatoid arthritis, type I diabetes, autoimmune psoriasis, lupus erythematosus, ulcerative colitis, sympathetic ophtalmia, bone resorption periodontal disease, immune thrombocytopaenic purpura and autoimmune lymphoproliferative syndrome, among others. It is currently thought that the onset of these diseases involves the activation of dormant disease specific autoreactive T cells, which are transformed into effector memory T cells ($T_{EM}$). The autoreactive T cells might differentiate from a naïve state into continuously activated memory T cells due to repeated autoantigen stimulation and contribute to inflammatory damage by migrating into tissues, secreting inflammatory cytokines, and exhibiting immediate effector function [Sallusto et al., 1999]. The mechanism involved in delayed type hypersensitivity (DTH) is another example of skin lesion caused by $T_{EM}$ cells [Soler et al., 2003]. The pathogenesis of many autoimmune diseases might also be due to memory B cells, especially those belonging to the class-switched $CD27^+IgD^-$ subset [Iglesias et al., 2001; O'Connor et al, 2001; Corcione et al., 2004]. For these reasons it is desirable to develop therapeutic agents that could target selectively $T_{EM}$ and class-switched memory B cells without impairing the activity of other lymphocyte subsets of cells, avoiding in this manner the compromise of acute immune responses. As mentioned earlier in examples 7 to 10 of this invention, voltage-gated Kv1.3 channels are new therapeutic targets for immunomodulation of $T_{EM}$ and class-switched memory B cells. $T_{EM}$ cells up-regulate Kv1.3 upon activation and their antigen-driven proliferation is quite sensitive to known substances that block Kv1.3 channels [Wulff et al., 2003]. On the contrary, naïve and $T_{CM}$ are much less sensitive to Kv1.3 blockers and rapidly become resistant to Kv1.3 blockade by up-regulating the calcium-activated K channel $K_{Ca}$ 3.1 [Wulff et al., 2003; Chandy et al., 2004]. During the process of differentiation B cells and T cells change their potassium channel dependence from $K_{Ca}$ 3.1 to Kv1.3 [Wulff et al., 2004]. Due to this fact Kv1.3 channel blockers inhibit the proliferation of these cells, without affecting naïve and $CD27^+IgD^+$ memory cells. Thus the use of blockers specific for Kv1.3 channels would affect preferentially $T_{EM}$ and class-switched memory B cells, without compromising the bulk of the immune response, but improving the health conditions developed as a consequence of the autoimmune diseases. Blockade of Kv1.3 channels ameliorates experimental autoimmune encephalomyelitis (EAE), bone resorption in periodontal diseases, and DTH response in animal models without causing obvious side effects [Koo et al., 1997; Beeton et al., 2001; Valverde et al., 2004]. Since blockage of Kv1.3 channels by peptides is promptly reversible it allows controlling the course of the treatment, which is not the case when chemotherapeutic agents or monoclonal antibodies are used, which takes months to subside. Obviously a major problem is to find highly selective peptides for this therapeutic treatment [Chandy et al., 2004].

As shown in examples 7-10 described earlier, both peptides (Vm23 and Vm24), subject of this invention, are potent and very specific blockers of Kv1.3 channels in vitro. The experiments were conducted directly on human T-lymphocytes in culture as well as using other cells expressing several voltage dependent K channels, in order to verify selectivity of action. For the purpose of "proof-of-concept", experiments in vivo were conducted with rats sensitized with dinitrofluorobenzeze (DNFB) as an agent capable of eliciting an important DTH-response.

In order to perform this kind of experiment we set up a protocol to study DTH response in rats. The system used is basically that described by Phanuphak et al., 1974. In brief, two groups of rats (3 or 5 animals each) were sensitized by applications of 40 microliters of 0.7% DNFB in 4:1 proportion of acetone: olive oil solution, in two consecutive days (days one and two), after gentle shaving of the dorsal-back region of the animals. After 7 days of the second application of the sensitizing solution, the animals were challenged by a single application of 20 microliter of 0.4% DNFB dissolved in the acetone: olive oil solution described above. This solution was spread over the dorsal surface of the right-side ears and allowed to dry, whereas the left-side ears were spread with only the vehicle solution (acetone:olive oil). On day eight of the protocol, a subcutaneous injection of 100 microliter of phosphate saline buffer pH 7.8 (PBS) was applied to each one of the animals used as control, whereas to the experimental group of rats, an amount of 10 micrograms pure Vm24 in 100 microliters PBS was subcutaneously applied. The thickness of both ears of all animals was measured 24 hours after of the application of Vm24.

The results of the experiments are shown in FIG. 16. It can be clearly seen that the control animals, not receiving Vm24 injection, had a mean value of inflammation of the ear in the order of 0.32 mm (labeled control) whereas those rats that were treated with one dose of 10 micrograms Vm24 had a reduced inflammation, no more than 0.10 mm thickness. These values correspond to real inflammation processes, since the thickness of the unchallenged ears (left-side ears) were subtracted. This represents a net decrement over 60% of the inflammation process. In conclusion, these results support the idea that Vm24 is an important immunosuppressant agent for the DTH-response in rats. Thus it is certainly a leading component that deserves being assayed as an inhibitor of immunological diseases dependent of the activation of T and B lymphocytes, where the contribution of Kv1.3 channels is important for eliciting or maintaining the disease.

References

Aebersold R, Goodlett D R (2001). Mass Spectrometry in Proteomics. Chem. Rev. 101:269-95.

Ahern C A, Zhang, J F, Wookalis M J, Horn R (2005). Modulation of the cardiac sodium channel NaV1 5 by Fyn, a Src family tyrosine kinase. Circ Res 96:991-8

Aiyar J, Withka J M, Rizzi J P, Singleton D H, Andrews G C, Lin W, Boyd J, Hanson D C, Simon M, Dethlefs B, Lee C-L, Hell J E, Gutman G A, Chandy K G (1995). Topology of the pore-region of a K+ channel revealed by the NMR-derived structures of scorpion toxins. Neuron 15:1169-81.

Alessandri-Haber N, Lecoq A, Gasparini S, Grangier-Macmath G, Jacquet G, Harvey A L, de Medeiros C, Rowan E G, Gola M, Menez A, Crest M (1999). Mapping the functional anatomy of BgK on Kv1.1, Kv1.2, and Kv1.3. Clues to design analogs with enhanced selectivity. J Biol Chem 274:35653-61.

Altschul S F, Gish W, Miller W, Myers E W, Lipman D J (1990). Basic local alignment search tool. J Mol Biol 215:403-10.

Aneiros A, Garcia I, Martinez J R, Harvey A L, Anderson A J, Marshall D L, Engstrom A, Hellman U, Karlsson E (1993). A potassium channel toxin from the secretion of the sea anemone *Bunodosoma granulifera*. Isolation, amino acid sequence and biological activity. Biochim Biophys Acta 1157:86-92.

Auguste P, Hugues M, Grave B, Gesquiere J C, Maes P, Tartar A, Romey G, Schweitz H, Lazdunski M (1990). Leiurotoxin I (scyllatoxin), a peptide ligand for Ca2(+)-activated K+ channels. Chemical synthesis, radiolabeling, and receptor characterization. J Biol Chem 265:4753-9.

Avdonin V, Tang X D, Hoshi T (2003). Stimulatory action of internal protons on Slo1 BK channels. Biophys J 84:2969-80

Bagdany M, Batista C V, Valdez-Cruz N A, Somodi S, Rodríguez de la Vega R C, Licea A F, Varga Z, Gaspar R, Possani L D, Panyi G (2005). Anuroctoxin, a new scorpion toxin of the α-KTx 6 subfamily, is highly selective for Kv1 3 over IKCa1 ion channels of human T lymphocytes. Mol Pharmacol 67:1034-44

Batista C V, Roman-Gonzalez S A, Salas-Castillo S P, Zamudio F Z, Gomez-Lagunas F, Possani L D (2007). Proteomic analysis of the venom from the scorpion *Tityus stigmurus*: Biochemical and physiological comparison with other *Tityus* species. Comp Biochem Physiol C Toxicol Phainiacol (doi: 10.1016/j.cbpc.2006.12.004).

Beeton C, Wulff H, Barbaria J, Clot-Faybesse O, Pennington M, Bernard D, Cahalan M D, Chandy K G, Beraud E (2001). Selective blockade of T lymphocyte K(+) channels ameliorates experimental autoimmune encephalomyelitis, a model for multiple sclerosis. Proc Natl Acad Sci USA 98:13942-7.

Beeton C, Chandy K G (2005). Potassium channels, memory T cells, and multiple sclerosis. Neuroscientist 11:550-62.

Beeton C, Pennington M W, Wulff H, Singh S, Nugent D, Crossley G, Khaytin I, Calabresi P A, Chen C Y, Gutman G A, Chandy K G (2005). Targeting effector memory T cells with a selective peptide inhibitor of Kv1.3 channels for therapy of autoimmune diseases. Mol Pharmacol 67:1369-81.

Beeton C, Wulff H, Standifer N E, Azam P, Mullen K M, Pennington M W, Kolski-Andreaco A, Wei E, Grino A, Counts D R, Wang P H, Leehealey C J, Andrews S, Sankaranarayanan A. Homerick D, Roeck W W, Tehranzadeh J, Stanhope K L, Zimin P, Havel P J, Griffey S, Knaus H G, Nepom G T, Gutman G A, Calabresi P A, Chandy K G (2006). Kv1 3 channels are a therapeutic target for T cell-mediated autoimmune diseases. Proc Natl Acad Sci USA 103:17414-9

Carbone E, Wanke E, Prestipino G, Possani L D, Maelicke A (1982). Selective blockage of voltage-dependent K+ channels by a novel scorpion toxin. Nature 296:90-1.

Castaneda O, Sotolongo V, Amor A M, Stocklin R, Anderson A J, Harvey A L, Engstrom A, Wernstedt C, Karlsson E (1995). Characterization of a potassium channel toxin from the Caribbean Sea anemone *Stichodactyla helianthus*. Toxicon 33:603-13.

Castle N A, Haylett D G, Jenkinson D H (1989). Toxins in the characterization of potassium channels. Trends Neurosci 12:59-65.

Chandy K G, Wulff H, Beeton C, Pennington M, Gutman G A, Cahalan M D (2004). K+ channels as targets for specific immunomodulation. Trends Pharmacol Sci 25:280-9.

Cooper N, Bussel J (2006). The pathogenesis of immune thrombocytopaenic purpura. Br J Haematol 133:364-74.

Corcione A, Casazza S, Ferretti E, Giunti D, Zappia E, Pistorio A, Gambini C, Mancardi G L, Uccelli A, Pistoia V. Recapitulation of B cell differentiation in the central nervous system of patients with multiple sclerosis. Proc Natl Acad Sci USA 101:11064-9.

Crest M, Jacquet G, Gola M, Zerrouk H, Benslimane A, Rochat H, Mansuelle P, Martin-Eauclaire M F (1992). Kaliotoxin, a novel peptidyl inhibitor of neuronal BK-type Ca(2+)-activated K+ channels characterized from *Androctonus mauretanicus mauretanicus* venom. J Biol Chem 267:1640-7.

Deutsch C, D Krause, S C Lee (1986). Voltage-gated potassium conductance in human T lymphocytes stimulated with phorbol ester. J Physiol (Lond) 372:405-23

Diego-Garcia E, Schwartz E F, D'Suze G, Gonzalez S A, Batista C V, Garcia B I, Rodríguez de la Vega R C, Possani L D (2007). Wide phylogenetic distribution of Scorpine and long-chain beta-KTx-like peptides in scorpion venoms: identification of "orphan" components. Peptides 28:31-7.

Doyle D A, C J Morais, R A Pfuetzner, A Kuo, M Gulbis, S L Cohen, B T Chait, R MacKinnon (1998). The structure of the potassium channel: molecular basis of K+ conduction and selectivity. Science 280:69-77

Drakopoulou E. Cotton J, Virelizier H, Bernardi E, Schoofs A R, Partiseti M, Choquet D, Gurrola G, Possani L D, Vita C (1995). Chemical synthesis, structural and functional characterisation of noxiustoxin, a powerful blocker of lymphocyte voltage-dependent K+ channels. Biochem Biophys Res Commun 213:901-7.

Fanger C M, H Rauer, Neben A L, Miller M J, Wulff H, Rosa J C, Ganellin C R, Chandy K G, Cahalan M D (2001). Calcium-activated potassium channels sustain calcium signaling in T lymphocytes. Selective blockers and manipulated channel expression levels. J Biol Chem 276: 12249-56

Feng J, Wible B, Li G R, Wang Z, Nattel S (1997). Antisense oligodeoxynucleotides directed against Kv1 5 mRNA specifically inhibit ultrarapid delayed rectifier K+ current in cultured adult human atrial myocytes. Circ Res 80:572-79

Galvez A, Gimenez-Gallego G, Reuben J P, Roy-Contancin L, Feigenbaum P, Kaczorowski G J, Garcia M L (1990). Purification and characterization of a unique, potent, peptidyl probe for the high conductance calcium-activated potassium channel from venom of the scorpion *Buthus tamulus*. J Biol Chem 265:11083-90.

Garcia M L, Garcia-Calvo M, Hidalgo P, Lee A, MacKinnon R (1994). Purification and characterization of three inhibitors of voltage-dependent K+ channels from *Leiurus quinquestriatus* var. *hebraeus* venom. Biochemistry 33:6834-9.

Garcia M L, Gao Y, McManus O B, Kaczorowski G J (2001). Potassium channels: from scorpion venoms to high-resolution structure. Toxicon 39:739-48.

Garcia-Calvo M, Leonard R J, Novick J, Stevens S P, Schmalhofer W, Kaczorowski G J, Garcia ML (1993). Purification, characterization, and biosynthesis of margatoxin, a component of *Centruroides margaritatus* venom that selectively inhibits voltage-dependent potassium channels. J Biol Chem 268:18866-74.

Giangiacomo K M, Ceralde Y, Mullmann T J (2004). Molecular basis of alpha-KTx specificity. Toxicon 43:877-86.

Ghanshani S, Wulff H, Miller M J, Rohm H, Neben A, Gutman G A, Cahalan M D, Chandy K G (2000). Up-regulation of the IKCa1 potassium channel during T-cell activation. Molecular mechanism and functional consequences. J Biol Chem 275:37137-49

Giangiacomo K M, Ceralde Y, Mullmann T J (2004). Molecular basis of alpha-KTx specificity. Toxicon 43:877-86

Goldstein S A, Miller C (1993). Mechanism of Charybdotoxin block of a voltage-gated K+ channel Biophys J 65:1613-1619

Goldstein S A, Pheasant D J, Miller C (1994). The Charybdotoxin receptor of a Shaker K+ channel: peptide and channel residues mediating molecular recognition. Neuron 12:1377-88

Gutman G A, Chandy K G, Grissmer S, Lazdunski M, McKinnon D, Pardo L A, Robertson G A, Rudy B, Sanguinetti M C, Stuhmer W, Wang X (2005). International Union of Pharmacology. LIII. Nomenclature and molecular relationships of voltage-gated potassium channels. Pharmacol Rev 57:473-508.

Grissmer S, Dethlefs B, Wasmuth J J, Goldin A L, Gutman G A, Cahalan M D, Chandy K G (1990). Expression and chromosomal localization of a lymphocyte K+ channel gene. Proc Natl Acad Sci USA 87:9411-5.

Grissmer S, Nguyen A N, Aiyar J, Hanson D C, Mather R J, Gutman G A, Karmilowicz M J, Auperin D D, Chandy K G (1994). Pharmacological characterization of five cloned voltage-gated K$^+$ channels, types Kv1.1, 1.2, 1.3, 1.5, 3.1, stably expressed in mammalian cell lines. Mol Pharmacol 45:1227-34

Grissmer S, Nguyen A N, Cahalan M D (1993). Calcium-activated potassium channels in resting and activated human T lymphocytes. Expression levels, calcium dependence, ion selectivity, pharmacology. J Gen Physiol 102: 601-30

Gutman G A, Chandy K G, Grissmer S, Lazdunski M, McKinnon D, Pardo L A, Robertson G A, Rudy B, Sanguinetti M C, Stuhmer W, Wang X (2005). International Union of Pharmacology. LIII. Nomenclature and molecular relationships of voltage-gated potassium channels. Pharmacol Rev 57:473-508

Harvey A L (1997). Recent studies on dendrotoxins and potassium ion channels. Gen Pharmacol 28:7-12.

Hidalgo P, MacKinnon R (1995). Revealing the architecture of a K+ channel pore through mutant cycles with a peptide inhibitor. Science 268:307-10.

Huelsenbeck J P, Ronquist F (2001). MRBAYES: Bayesian inference of phylogenetic trees. Bioinformatics 17:754-5.

Iglesias A, Bauer J, Litzenburger T, Schubart A, Linington C (2001). T- and B-cell responses to myelin oligodendrocyte glycoprotein in experimental antoimmune encephalomyelitis and multiple sclerosis. Glia 36:220-34.

Immke D, Wood M, Kiss L, Korn S J (1999). Potassium-dependent changes in the conformation of the Kv2.1 potassium channel pore. J Gen Physiol 113:819-36

Jameson B A, McDonnell J M, Marini J C, Korngold R (1994). A rationally designed CD4 analogue inhibits experimental allergic encephalomyelitis. Nature 368:744-6.

Janeway C A, Travers P, Walport M, Shlomchik M J (2001). Immunobiology. 5 ed. Garland Publishing, New York. 187-220 pp Jouirou B, Mouhat S, Andreotti N, De Waard M, Sabatier J M (2004). Toxin determinants required for interaction with voltage-gated K+ channels. Toxicon 43:909-14.

Judge S I, Bever C T Jr (2006). Potassium channel blockers in multiple sclerosis: neuronal Kv channels and effects of symptomatic treatment. Pharmacol Ther 111:224-59.

Juvvadi P, Vunnam S, Merrifield R B (1996). Synthetic melittin, its enantio, retro, and retroenantio isomers, and selected chimeric analogs: their antibacterial, hemolytic, and lipid bilayer action. J Am Chem Soc 118:8989-97.

Kalman K, M W Pennington, Lanigan M D, Nguyen A, Rauer H, Mahnir V, Paschetto K, Kem W R, Grissmer S, Gutman G A, Christian E P, Cahalan M D, Norton R S, Chandy K G (1998). ShK-Dap22, a potent Kv1 3-specific immunosuppressive polypeptide. J Biol Chem 273:32697-707

Koch R O, Wanner S G, Koschak A, Hanner M, Schwarzer C, Kaczorowski G J, Slaughter R S, Garcia M L, Knaus H G (1997). Complex subunit assembly of neuronal voltage-gated K+ channels. Basis for high-affinity toxin interactions and pharmacology. J Biol Chem 272:27577-81

Koo G C, Blake J T, Talento A, Nguyen M, Lin S, Sirotina A, Shah K, Mulvany K, Hora D Jr, Cunningham P, Wunderler D L, McManus O B, Slaughter R, Bugianesi R, Felix J, Garcia M, Williamson J, Kaczorowski G, Sigal N H, Springer M S, Feeney W (1997). Blockade of the voltage-gated potassium channel Kv1.3 inhibits immune responses in vivo. J Immunol 158:5120-8.

Krezel A M, Kasibhatla C, Hidalgo P, MacKinnon R, Wagner G (1995). Solution structure of the potassium channel inhibitor agitoxin 2: caliper for probing channel geometry. Protein Sci 4:1478-89.

Kurata H T, Wang Z, Fedida D (2004). NH2-terminal inactivation peptide binding to C-type-inactivated Kv channels. J Gen Physiol 123:505-20

Lebrun B, Romi-Lebrun R, Martin-Eauclaire M F, Yasuda A, Ishiguro M, Oyama Y, Pongs O, Nakajima T (1997). A four-disulphide-bridged toxin, with high affinity towards voltage-gated K+ channels, isolated from *Heterometrus spinnifer* (Scorpionidae) venom. Biochem J 328:321-7.

Lee S Y, Lee A, Chen J, MacKinnon R (2005). Structure of the KvAP voltage-dependent K+ channel and its dependence on the lipid membrane. Proc Natl Acad Sci USA 102: 15441-6.

Lerner E C, Qian Y, Blaskovich M A, Fossum R D, Vogt A, Sun J, Cox A D, Der C J, Hamilton A D, Sebti S M (1995). Ras CAAX peptidomimetic FTI-277 selectively blocks oncogenic Ras signaling by inducing cytoplasmic accumulation of inactive Ras-Raf complexes. J Biol Chem 270: 26802-6.

Lewis R S, Cahalan M D (1995). Potassium and calcium channels in lymphocytes. Annu Rev Immunol 13:623-53.

Lewis R S (2001). Calcium signaling mechanisms in T lymphocytes. Annu Rev Immunol 19:497-521

Long S B, Campbell E B, Mackinnon R (2005). Crystal structure of a mammalian voltage-dependent Shaker family K+ channel Science 309):897-903.

Matteson D R, Deutsch C (1984). K channels in T lymphocytes: a patch clamp study using monoclonal antibody adhesion. Nature 307:468-71

Merrifield R B (1964). Solid-phase peptide synthesis. 2. An improved synthesis of bradykinin. Biochemistry 3:1385-90.

Miller C, Moczydlowski E, Latorre R, Phillips M (1985). Charybdotoxin, a protein inhibitor of single Ca2+-activated K+ channels from mammalian skeletal muscle. Nature 313:316-8.

Mouhat S, Jouirou B, Mosbah A, De Waard M, Sabatier J M (2004). Diversity of folds in animal toxins acting on ion channels. Biochem J 378:717-26.

Moczydlowski E (1985). Chemical basis for alkali cation selectivity in potassium-channel proteins. Chem Biol 5:R291-301.

O'Connor K, Bar-Or A, Hafler D A (2001). The neuroimmunology of multiple sclerosis: possible roles of T and B lymphocytes in immunopathogenesis. J Clin Immunol 21:81-92.

O'Leary M E, Chen L Q, Kallen R G, Horn R (1995). A molecular link between activation and inactivation of sodium channels. J Gen Physiol 106:641-58

Oren H, Ozkal S, Gulen H, Duman M, Ucar C, Atabay B, Yilmaz S, Kargi A, Irken G (2002). Autoimmune lymphoproliferative syndrome: report of two cases and review of the literature. Ann Hematol 81:651-3.

Orengo C A, Thornton J M (2005). Protein families and their evolution-a structural perspective. Annu Rev Biochem 74:867-900.

Panyi G, Varga Z, Gaspar R (2004). Ion channels and lymphocyte activation. Immunol Lett 92:55-66

Park C S, Miller C (1992). Mapping function to structure in a channel-blocking peptide: electrostatic mutants of charybdotoxin. Biochemistry 31:7749-55

Patel S P, Campbell D L (2005). Transient outward potassium current, 'Ito', phenotypes in the mammalian left ventricle: underlying molecular, cellular and biophysical mechanisms. J Physiol 569:7-39

Pearson W R, Lipman D J (1988). Improved tools for biological sequence comparison. Proc Natl Acad Sci USA 85:2444-8.

Pennington M W, Byrnes M E, Zaydenberg I, Khaytin I, de Chastonay J, Krafte D S, Hill R, Mahnir V M, Volberg W A, Gorczyca W, Kem W R (1995). Chemical synthesis and characterization of ShK toxin: a potent potassium channel inhibitor from a sea anemone. Int J Pept Protein Res 46:354-8.

Peter J, Varga Z, Hajdu P, Gaspar R J, Damjanovich S, Horjales E, Possani L D, Panyi G (2001). Effects of toxins Pi2 and Pi3 on human T lymphocyte Kv1 3 channels: the role of Glu7 and Lys24. J Membr Biol 179:13-25

Phanuphak P, Moorthead J W, Claman H N (1974) Tolerance and contact sensitivity to DNFB in mice. I. In vivo detection by ear swelling and correlation with in vitro cell stimulation. J. Immunol. 112:115-23.

Possani L D, Martin B M, Svendsen I, Rode G S, Erickson B W (1985). Scorpion toxins from *Centruroides noxius* and *Tityus serrulatus*. Primary structures and sequence comparison by metric analysis. Biochem J 229:739-50.

Possani L D, Becerril B, Delepierre M, Tytgat J (1999). Scorpion toxins specific for Na+-channels. Eur J Biochem 264:287-300.

Possani L D, Rodríguez de la Vega R C (2006). Scorpion venom peptides. In: Handbook of biologically active peptides p. 339-354 (Kastin, A. editor). Academic Press, San Diego Calif., USA.

Peter J, Varga Z, Hajdu P, Gaspar R J, Damjanovich S, Horjales E, Possani L D, Panyi G (2001). Effects of toxins Pit and Pi3 on human T lymphocyte Kv1 3 channels: the role of Glu7 and Lys24. J Membr Biol 179:13-25

Rogart R B, Cribbs L, Muglia L K, Kephart D D, Kaiser M W (1989). Molecular cloning of a putative tetrodotoxin-resistant rat heart Na+ channel isoform. Proc Natl Acad Sci USA 86:8170-4

Ronquist F, Huelsenbeck J P (2003). MrBayes 3: Bayesian phylogenetic inference under mixed models. Bioinformatics 19:1572-4.

Rauer H, Lanigan M D, Pennington M W, Aiyar J, Ghanshani S, Cahalan M D, Norton R S, Chandy K G (2000). Structure-guided transformation of charybdotoxin yields an analog that selectively targets Ca(2+)-activated over voltage-gated K(+) channels. J Biol Chem 275:1201-8.

Rodríguez de la Vega R C, Merino E, Becerril B, Possani L D (2003). Novel interactions between K+ channels and scorpion toxins. Trends Pharmacol Sci 24:222-7.

Rodríguez de la Vega R C, Possani L D (2004). Current views on scorpion toxins specific for K+-channels. Toxicon 43:865-75.

Sallusto F, Lenig D, Forster R, Lipp M, Lanzavecchia A (1999). Two subsets of memory T lymphocytes with distinct homing potentials and effector functions. Nature 401:708-12.

Sallusto F, Geginat J, Lanzavecchia A (2004). Central memory and effector memory T cell subsets: function, generation, maintenance. Annu Rev Immunol 22:745-63

Sanguinetti M C, Tristani-Firouzi M (2006). hERG potassium channels and cardiac arrhythmia. Nature 440:463-9

Sarin V K, Kent S B H, Tam J P, Merrifield B R (1981). Quantitative monitoring of solid-phase peptide synthesis by the ninhydrin reaction. Anal Biochem 117:147-57

Soler D, Humphreys T L, Spinola S M, Campbell J J (2003). CCR4 versus CCR10 in human cutaneous TH lymphocyte trafficking. Blood 101:1677-82.

Stampe P, Kolmakova-Partensky L, Miller C (1994). Intimations of K+ channel structure from a complete functional map of the molecular surface of charybdotoxin. Biochemistry 33:443-50.

Strong P N (1990). Potassium channel toxins. Pharmacol Ther 46:137-62.

Sugg E E, Garcia M L, Reuben J P, Patchett A A, Kaczorowski G J (1990). Synthesis and structural characterization of charybdotoxin, a potent peptidyl inhibitor of the high conductance Ca2(+)-activated K+ channel. J Biol Chem 265:18745-8.

Thompson J D, Gibson T J, Plewniak F, Jeanmougin F, Higgins D G (1997). The CLUSTAL_X windows interface: flexible strategies for multiple sequence alignment aided by quality analysis tools. Nucleic Acids Res 25:4876-82.

Thornton J W, DeSalle R (2000). Gene family evolution and homology: genomics meets phylogenetics. Annu Rev Genomics Hum Genet 1:41-73.

Tytgat J, Chandy K G, Garcia M L, Gutman G A, Martin-Eauclaire M F, van der Walt J J, Possani L D (1999). A unified nomenclature for short-chain peptides isolated from scorpion venoms: alpha-KTx molecular subfamilies. Trends Pharmacol Sci 20:444-7.

Valdez-Cruz N A, Batista C V, Possani L D (2004). Phaiodactylipin, a glycosylated heterodimeric phospholipase A from the venom of the scorpion *Anuroctonus phaiodactylus*. Eur J Biochem 271:1453-64.

Valverde P, Kawai T, Taubman M A (2004). Selective blockade of voltage-gated potassium channels reduces inflammatory bone resorption in experimental periodontal disease. J Bone Miner Res 19:155-64.

Vennekamp J, Wulff H, Beeton C, Calabresi P A, Grissmer S, Hansel W, Chandy K G (2004). Kv1 3-blocking 5-phenylalkoxypsoralens: a new class of immunomodulators. Mol Pharmacol 65:1364-1374

Viglietta V, Kent S C, Orban T, Hafler D A (2002). GAD65-reactive T cells are activated in patients with autoimmune type 1a diabetes. J Clin Invest 109:895-903

Visan V, Fajloun Z, Sabatier J M, Grissmer S (2004). Mapping of maurotoxin binding sites on hKv1 2, hKv1 3, hIKCa1 channels. Mol Pharmacol 66:1103-12

Wei A D, Gutman G A, Aldrich R, Chandy K G, Grissmer S, Wulff H (2005). International Union of Pharmacology. LII. Nomenclature and molecular relationships of calcium-activated potassium channels. Pharmacol Rev 57:463-472

Wulff H, Gutman G A, Cahalan M D, Chandy K G (2001). Delineation of the clotrimazole/TRAM-34 binding site on the intermediate conductance calcium-activated potassium channel, IKCa1. J Biol Chem 276:32040-5

Wulff H, Calabresi P A, Allie R, Yun S, Pennington M, Beeton C, Chandy K G (2003). The voltage-gated Kv1.3 K(+) channel in effector memory T cells as new target for MS. J Clin Invest 111:1703-13.

Wulff H, Knaus H G, Pennington M, Chandy K G (2004). K+ channel expression during B cell differentiation: implications for immunomodulation and autoimmunity. J Immunol 173:776-86.

Yamashita K, Choi U, Woltz P C, Foster S, Sneller M C, Hakim F T, Fowler D H (2004). Severe chronic graft-versus-host disease is characterized by a preponderance of CD4+ effector memory cells relative to central memory cells. Blood 103:3986-8

Zamudio F Z, Saavedra R, Martin B M, Gurrola-Briones G, Herion P, Possani L D (1992). Amino acid sequence an immunological characterization with monoclonal antibod ies of two toxins from the venom of the scorpion *Centruroides noxius* Hoffmann. Eur J Biochem 204:281-92.

Zamudio F Z, Conde R, Arevalo C, Becerril B, Martin B M, Valdivia H H, Possani L D (1997). The mechanism of inhibition of ryanodine receptor channels by imperatoxin I, a heterodimeric protein from the scorpion *Pandinus imperator*. J Biol Chem 272:11886-94.

Zhu S, Huys I, Dyason K, Verdonck F, Tytgat J (200). Evolutionary trace analysis of scorpion toxins specific for K-channels. Proteins 54:361-70.

Zweifach A, Lewis R S (1993). Mitogen-regulated Ca2+ current of T lymphocytes is activated by depletion of intracellular Ca2+ stores. Proc Natl Acad Sci USA 90:6295-99.

---

What is claimed is:

1. An isolated and purified peptide with an amino acid sequence selected from the group consisting of SEQ ID NO: 1 and SEQ ID NO: 2, wherein said peptide is capable of blocking with high affinity and specificity a potassium channel Kv1.3.

2. A method of inhibiting Kv1.3 potassium channel activity in a mammalian cell, comprising contacting said mammalian cell with an effective amount of a peptide to block said channel activity in said cell wherein said peptide has an amino acid sequence selected from the group consisting of SEQ ID No:1, SEQ ID No:2, and a pharmaceutically acceptable salt thereof.

3. The method of claim 2 wherein said mammalian cell is a human lymphocyte cell.

4. A method of attenuating calcium signaling pathway in a T-lymphocyte cell comprising contacting said T-lymphocyte cell with an effective amount of a peptide having a Kv1.3 potassium channel blocking activity, wherein said peptide has an amino acid sequence selected from the group consisting of SEQ ID NO: 1 and SEQ ID NO: 2.

5. A method of suppressing T-cell activation process in the immune system of a mammal, comprising contacting a population of said T-cells with an effective amount of a peptide having a Kv1.3 potassium channel blocking activity, wherein said peptide has an amino acid sequence selected from the group consisting of SEQ ID NO: 1, SEQ ID NO: 2, and a pharmaceutically acceptable salt thereof.

6. The method of claim 5, wherein said mammal is a human.

7. The method of claim 5, wherein said T-cell activation is caused by an immune response in said mammal.

8. The method of claim 7, wherein said immune response is the result of heterologous organ rejection.

9. The method of claim 7, wherein said immune response is the result of an autoimmune disease.

10. A method of suppressing an immune response in a mammal, comprising administering to said mammal a composition comprising a peptide having a Kv1.3 potassium channel blocking activity, in an effective amount to suppress said response in said mammal, wherein said peptide has an amino acid sequence selected from the group consisting of SEQ ID NO: 1, SEQ ID NO: 2, and a pharmaceutically acceptable salt thereof.

11. The method of claim 10, wherein said immune response is the result of heterologous organ rejection.

12. The method of claim 10, wherein said immune response is the result of an autoimmune disease.

13. A method for the prophylactic or therapeutic treatment of heterologous organ rejection in a subject in need thereof comprising administering to the subject an effective amount of a composition comprising a peptide having a Kv1.3 potassium channel blocking activity, wherein said peptide has an amino acid sequence selected from the group consisting of SEQ ID NO: 1, SEQ ID NO: 2, and a pharmaceutically acceptable salt thereof.

14. The method of claim 13, wherein said rejected organ is a heart, a lung, a liver, a kidney or a pancreas.

15. The method of claim 13, wherein the subject in need of said treatment is a human.

16. The method of claim 13, wherein the composition is administered topically, systemically, intravenously, intraperitoneally, intramuscularly, subcutaneously, intranasally, transdermally, orally, or by intradermal injection, intrabronchial instillation, gastrointestinal delivery, or transmucosal delivery.

17. A method for the prophylactic or therapeutic treatment of an autoimmune disease associated to lymphocyte $T_{EM}$ in a subject in need thereof comprising administering to the subject an effective amount of a composition comprising a peptide having a Kv1.3 potassium channel blocking activity, wherein said peptide have amino acid sequence selected from the group consisting of SEQ ID NO: 1, SEQ ID NO: 2, and a pharmaceutically acceptable salt thereof.

18. The method of claim 17, wherein the subject in need of said treatment is a human.

19. The method of claim 17, wherein said autoimmune disease associated to lymphocyte $T_{EM}$ is selected from the group consisting of multiple sclerosis, rheumatoid arthritis, type I diabetes, autoimmune psoriasis, lupus erythematosus, ulcerative colitis, sympathetic ophtalmia, bone resorption periodontal disease, immune thrombocytopaenic purpura and autoimmune lymphoproliferative syndrome.

20. The method of claim 17, further comprising administering to said subject at least one additional immunosuppressive agent.

21. The method of claim 20, wherein the additional immunosuppressive agent is selected form the group consisting of cyclosporine, rapamycin, azathioprine, prednisone, ShK toxin, ShK derivatives and deoxyspergualin, their derivatives, or a salt thereof.

22. The method of claim 17, wherein the composition is administered topically, systemically, intravenously, intraperitoneally, intramuscularly, subcutaneously, intranasally, transdermally, orally, or by intradermal injection, intrabronchial instillation, gastrointestinal delivery, or transmucosal delivery.

23. A pharmaceutical composition comprising (1) at least one peptide having a Kv1.3 potassium channel blocking activity, wherein said peptide has an amino acid sequence selected from the group consisting of SEQ ID NO: 1, SEQ ID NO: 2, and a pharmaceutically acceptable salt thereof, and (2) a pharmaceutically acceptable carrier, and (3) optionally at least one additional immunosuppressive agent.

24. The pharmaceutical composition of claim 23 wherein the optional additional immunosuppressive agent is selected form the group consisting of cyclosporine, rapamycin, azathioprine, prednisone, ShK toxin, ShK derivatives and deoxyspergualin, their derivatives, or a salt thereof.

* * * * *